United States Patent
Schuch et al.

(10) Patent No.: US 12,121,568 B2
(45) Date of Patent: Oct. 22, 2024

(54) **IDENTIFICATION OF LYSINS AND DERIVATIVES THEREOF WITH BACTERICIDAL ACTIVITY AGAINST *PSEUDOMONAS AERUGINOSA***

(71) Applicant: CONTRAFECT CORPORATION, Yonkers, NY (US)

(72) Inventors: Raymond Schuch, Mountain Lakes, NJ (US); Chiara Indiani, Metuchen, NJ (US)

(73) Assignee: AUROBAC THERAPEUTICS SAS, Lyons (FR)

( * ) Notice: Subject to any disclaimer, the term of this patent is extended or adjusted under 35 U.S.C. 154(b) by 185 days.

(21) Appl. No.: 16/772,001

(22) PCT Filed: Dec. 12, 2018

(86) PCT No.: PCT/US2018/065265
§ 371 (c)(1),
(2) Date: Jun. 11, 2020

(87) PCT Pub. No.: WO2019/118632
PCT Pub. Date: Jun. 20, 2019

(65) Prior Publication Data
US 2021/0085758 A1    Mar. 25, 2021

Related U.S. Application Data

(60) Provisional application No. 62/721,969, filed on Aug. 23, 2018, provisional application No. 62/597,577, filed on Dec. 12, 2017.

(51) Int. Cl.
| | | |
|---|---|---|
| A61K 38/47 | (2006.01) | |
| A61K 45/06 | (2006.01) | |
| A61P 31/04 | (2006.01) | |
| C12N 9/36  | (2006.01) | |

(52) U.S. Cl.
CPC .............. *A61K 38/47* (2013.01); *A61K 45/06* (2013.01); *A61P 31/04* (2018.01); *C12N 9/2462* (2013.01); *C12Y 302/01017* (2013.01)

(58) Field of Classification Search
CPC ....... A61K 38/47; A61P 31/04; C12N 9/2462; C12Y 302/01017
See application file for complete search history.

(56) References Cited

U.S. PATENT DOCUMENTS

| | | | |
|---|---|---|---|
| 10,744,189 B2* | 8/2020 | Schuch ................ A61K 9/0019 |
| 2012/0052048 A1 | 3/2012 | Da Costa Garcia et al. | |
| 2017/0130214 A1 | 5/2017 | Fischetti et al. | |
| 2017/0298334 A1 | 10/2017 | Fischetti et al. | |
| 2019/0070269 A1 | 3/2019 | Schuch et al. | |

FOREIGN PATENT DOCUMENTS

| | | |
|---|---|---|
| CN | 103119158 A | 5/2013 |
| CN | 103201381 A | 7/2013 |
| CN | 105793420 A | 7/2016 |
| CN | 108103050 A | 6/2018 |
| JP | 2012500642 A | 1/2012 |
| WO | 2010023207 A2 | 3/2010 |
| WO | 2010023207 A3 | 3/2010 |
| WO | 2011060920 A2 | 5/2011 |
| WO | 2011060920 A3 | 5/2011 |
| WO | 2011060920 A8 | 5/2011 |
| WO | 2011134998 A1 | 11/2011 |
| WO | 2011134998 A8 | 11/2011 |
| WO | 2012059545 A1 | 5/2012 |
| WO | 2015070912 A1 | 5/2015 |
| WO | WO 2017/049233 | 3/2017 |
| WO | 2019118632 A1 | 6/2019 |
| WO | 2019191633 A2 | 10/2019 |
| WO | 2019191633 A3 | 10/2019 |
| WO | 2020046747 A1 | 3/2020 |

OTHER PUBLICATIONS

EP Communication pursuant to Rule 164 (1) EPC issued in European Patent Application No. 18889220.2 dated Jul. 26, 2021, 14 pages.
Yang, H. et al., "Antibacterial Activity of a Novel Peptide-Modified Lysin Against Acinetobacer baumannii and *Pseudomonas aeruginosa*", Frontiers in Microbiology, Dec. 22, 2015, pp. 1-9, vol. 6, No. 1471, XP055657170.
Guo, M. et al., "A Novel Antimicrobial Endolysin, LysPA26, against *Pseudomonas aeruginosa*", Frontiers in Microbiology, Feb. 27, 2017, pp. 1-9, vol. 8, No. 293, XP055810486.
Uniparc: "UPI0000F257F7", Feb. 7, 2008, XP055823900, www.uniprot.org/uniparc/UPI0000F257F7.
Extended European Search Report issued in European Patent Application No. 18889220.2 dated Nov. 2, 2021, 14 pages.
International Preliminary Report on Patentability for corresponding International Patent Application No. PCT/US2020/026681, dated Sep. 28, 2021 (13 pages).
International Preliminary Report on Patentability for PCT/US2018/065265, dated Jun. 25, 2020 (10 pages).
UnitProtKB Accession No. B0KJQ1_PSEPG, "Lysozyme, Pseudomonas putida," Mar. 18, 2008.

(Continued)

*Primary Examiner* — Ruth A Davis
(74) *Attorney, Agent, or Firm* — MH2 TECHNOLOGY LAW GROUP, LLP

(57) ABSTRACT

Disclosed are novel lysin polypeptides active against Gram-negative bacteria, particularly *P. aeruginosa*, pharmaceutical compositions containing them and methods for their use to treat Gram-negative bacterial infections and more generally to inhibit the growth, or reduce the population, or kill Gram-negative bacteria, including without limitation disrupting biofilms formed by such bacteria. Certain of the disclosed lysins have been modified in amino acid sequence compared to that of lysins by replacement of certain charged amino acids with noncharged amino acids and/or by fusion at the N- or C-terminus with antibacterial peptide sequences with or without an intervening linker.

36 Claims, No Drawings
Specification includes a Sequence Listing.

(56) References Cited

OTHER PUBLICATIONS

Diez-Martinez, R. et al., Improving the Lethal Effect of Cpl-7, a Pneumococcal Phage Lysozyme with Broad Bactericidal Activity by Inverting the Net Charge of Its Cell Wall-Binding Module, Antimicrob. Agents Chemother. 2013; 57(11):5355-5365.
Briers, Y. et al., Engineered Endolysin-Based 'Artilysins' to Combat Multidrug-Resistant Gram-Negative Pathogens, mBio 2014; 5(4):e01379-14.
Briers, Y. et al., Art-175 Is a Highly Efficient Antibacterial against Multidrug-Resistant Strains and Persisters of *Pseudomonas aeruginosa*, Antimicrob. Agents Chemother. 2014; 58(7):3774-3784.
Briers, Y. et al., Breaking barriers: expansion of the use of endolysins as novel antibacterials against Gram-negative bacteria, Future Microbiol. 2015; 19(3):377-390.
Daniels, D.S. et al., Intrinsically Cell-Permeable Miniature Proteins Based on a Minimal Cationic PPII Motif, J. Am. Chem. Soc. 2007; 129:14578-14579.
Deslouches, B. et al., Activity of the De Novo Engineered Antimicrobial Peptide WLBU2 against *Pseudomonas aeruginosa* in Human Serum and Whole Blood: Implications for Systemic Applications, Antimicrob. Agents and Chemother. 2005; 49(8):3208-3216.
Gertsmans, H. et al., From endolysins to Artilysin®s: novel enzyme-based approaches to kill drug-resistant bacteria, Biochem. Soc. Trans. 2016; 44:123-128.
Griswold, K.E., et al., Bioengineered lysozyme in combination therapies for *Pseudomonas aeruginosa* lung Infections, Bioengineered 2014; 5(2):143-147.
Lood, R. et al., A Highly Active and Negatively Charged *Streptococcus pyogenes* Lysin with Rare D-Alanyl-L-Alanine Endopeptidase Activity Protects Mice against Streptococcal Bacteremia, Antimicrob. Agents and Chemother. 2014; 58(6):3073-3084.
Lood, R. et al., Novel Phage Lysin Capable of Killing the Multidrug-Resistant Gram-Negative Bacterium Acinetobacter baumannii in a Mouse Bacteremia Model, Antimicrob. Agents and Chemother. 2015; 59(4):1983-1991.
Lv, Y. et al., Antimicrobial Properties and Membrane-Active Mechanism of a Potential alpha-Helical Antimicrobial Derived from Cathelicidin PMAP-36, Plos One 2013; 9(1):e86364.
Lyu, Y. et al., Antimicrobial activity, improved cell selectivity and mode of action of short PMAP-36-derived peptides against bacteria and Candida, Scientific Reports 2016; 6:27258.
Sanchez-Gomez, S. et al., Comparative analysis of selected methods for the assessment of antimicrobial and membrane-permeabilizing activity: a case study for lactoferricin derived peptide, BMC Microbiol. 2008; 8:196-204.
Scanlon, T.C. et al., Enhanced antimicrobial activity of engineered human lysozyme, ACS Chem. Biol. 2010; 5(9):809-818.
Silhavy, T.J. et al., The Bacterial Cell Envelope, Cold Spring Harb Perspect Biol 2010; 2:a000414.
Teneback, C.C. et al., Bioengineered Lysozyme Reduces Bacterial Burden and Inflammation in a Murine Model of Mucoid *Pseudomonas aeruginosa* Lung Infection, Antimicrob. Agents and Chemother. 2013; 57(11):5559-5564.
Thandar, M. et al., Novel Engineered Peptides of a Phage Lysin as Effective Antimicrobials against Multidrug- Resistant Acinetobacter baumannii, Antimicrob. Agents and Chemother. 2016; 60(5):2671-2679.
Vaara, M., Agents That Increase the Permeability of the Outer Membrane, Microbiol. Revs. 1992; 56(3):395-411.
Vaara, M. et al., Group of Peptides That Act Synergistically with Hydrophobic Antibiotics against Gram-Negative Enteric Bacteria, Antimicrob. Agents Chemother. 1996; 40(8):1801-1805.
Wang, J. et al., Membrane-Active Mechanism of the synthetic centrosymmetric alpha-helical peptides with Gly-Gly pairs, Scientific Reports 2015; 5:15963.
Yeaman, M.R. & Yount, N.Y., Mechanisms of Antimicrobial Peptide Action and Resistance, Pharmacological Revs. 2003; 55(1):27-55.
Zhu, X. et al., Importance of Tryptophan in Tranforming an Amphipathic Peptide into a *Pseudomonas aeruginosa*-Targeted Antimicrobial Peptide, Plos One 2014; 9(12): e114605.
International Search Report and Written Opinion for WO 2019/118632 A1, dated May 13, 2019 (13 pages).
International Search Report and Written Opinion for WO 2020/026681 A1, dated Sep. 15, 2020 (18 pages).
(National Center for Biotechnology Information) lysozyme [*Pseudomonas putida*].Genbank entry [online]. Oct. 29, 2017 [retrieved on Jun. 29, 2020]. Retrieved from the Internet: URL: https://www.ncbi.nlm.nih.gov/protein/WP_096426459.1 ; p. 1.
Suave et al., "Bacteriophage-Derived Lysins can be Engineered to Exert a Rapid and Potent Bactericidal Effect Against *Pseudomonas aeruginosa* in Serum Sunday-HMB LB14", Australian Society for Microbiology (ASM) Conference 2018, presentation, Jun. 10, 2018, XP093033750, 1 page.
Extended European Search Report dated Apr. 3, 2023 for EP Application No. 20785056.1 (8 pages).
Author Unknown, putative peptidoglycan-binding domain containing protein [*Pseudomonas aeruginosa*], Accession No. ACD38663.1, NCBI Protein [online] (retrieved on Oct. 31, 2022), Aug. 20, 2008, retrieved from the Internet <URL:https://www.ncbi.nlm.nih.gov/protein/187939515?sat=4&satkey=24935045>, 3 pages.
Author Unknown, hypothetical protein GOS_6457617 [marine metagenome], Accession No. ECJ78460.1, NCBI Protein [online] (retrieved on Oct. 31, 2022), Apr. 4, 2007, retrieved from the Internet <URL:https://www.ncbi.nlm.nih.gov/protein/140136659?sat=37&satkey=260496206>, 3 pages.
Author Unknown, P5 [Psedomonas phage phi2954], Accession No. YP_002600773.1, NCBI Protein [online] (retrieved on Oct. 31, 2022), Oct. 20, 2015, retrieved from the Internet <URL:https://www.ncbi.nlm.nih.gov/protein/223869195?sat=46&satkey=163037097>, 2 pages.
Author Unknown, phage lysozyme [*Pseudomonas aeruginosa*], Accession No. WP_016046696.1, NCBI Protein [online] (retrieved on Oct. 31, 2022), May 26, 2015, retrieved from the Internet <URL:https://www.ncbi.nlm.nih.gov/protein/506580496?sat=47&satkey=15484840>, 2 pages.
Author Unknown, putative chitinase-like endolysin [Acinetobacter phage phiAB6], Accession No. YP_009288673.1, NCBI Protein [online] (retrieved on Oct. 31, 2022), Sep. 23, 2016, retrieved from the Internet <URL: https://www.ncbi.nlm.nih.gov/protein/1070065125?sat=46&satkey=163030700>, 2 pages.
Author Unknown, hypothetical protein [Pseudomonas phage PhiPA3], Accession No. YP_009217242.1, NCBI Protein [online] (retrieved on Oct. 31, 2022), Jan. 5, 2016, retrieved from the Internet <URL:https://www.ncbi.nlm.nih.gov/protein/971764240?sat=46&satkey=163029886>, 2 pages.
Author Unknown, hypothetical protein [*Acinetobacter* sp. 1294596], Accession No. WP_034684053.1, NCBI Protein [online] (retrieved on Oct. 31, 2022), Jul. 21, 2016, retrieved from the Internet <URL:https://www.ncbi.nlm.nih.gov/protein/736677684?sat=46&satkey=146588177>, 2 pages.
Author Unknown, hypothetical protein PaP2_gp17 [Pseudonomas phage PaP2], Accession No. YP_024745.1, NCBI Protein [online] (retrieved on Oct. 31, 2022), Aug. 23, 2012, retrieved from the Internet <URL:https://www.ncbi.nlm.nih.gov/protein/48697087?sat=46&satkey=163036432>, 3 pages.
Author Unknown, lysozyme [*Pseudomonas putida*], Accession No. WP_012273008.1, NCBI Protein [online] (retrieved on Oct. 31, 2022), Oct. 29, 2017, retrieved from the Internet <URL:https://www.ncbi.nlm.nih.gov/protein/501229990?sat=47&satkey=77128334>, 2 pages.
Author Unknown, UniProt [online] Accession No. I1TQ26 (retrieved on Oct. 31, 2022), Jun. 7, 2017, retrieved from the Internet <URL:https://rest.uniprot.org/unisave/I1TQ26?format=txt&versions=8>, 1 page.
Author Unknown, putative endolysin [Pseudomonas phage PAJU2], GenBank: BAG75011.1, National Library of Medicine, https://www.ncbi.nlm.nih.gov/protein/BAG75011.1?report=genbank&log$=protalign&blast_rank=1&RID=1SAHTVDN01N, 1 page.

(56) References Cited

OTHER PUBLICATIONS

Pomares et al., Sensitization of Microcin J25-Resistant Strains by a Membrane-Permeabiliaing Peptide, Appl Environ Microbiol., 2010, 76(20), pp. 6837-6842.

* cited by examiner

SEQUENCE LISTING

<160> NUMBER OF SEQ ID NOS: 54

<210> SEQ ID NO 1
<211> LENGTH: 147
<212> TYPE: PRT
<213> ORGANISM: UNKNOWN
<220> FEATURE:
<223> OTHER INFORMATION: Marine metagenome

<400> SEQUENCE: 1

Met Lys Ile Ser Leu Glu Gly Leu Ser Leu Ile Lys Lys Phe Glu Gly
1               5                   10                  15

Cys Lys Leu Glu Ala Tyr Lys Cys Ser Ala Gly Val Trp Thr Ile Gly
                20                  25                  30

Tyr Gly His Thr Ala Gly Val Lys Gly Asp Val Cys Thr Gln Glu
            35                  40                  45

Glu Ala Glu Lys Leu Leu Arg Gly Asp Ile Phe Lys Phe Glu Glu Tyr
    50                  55                  60

Val Gln Asp Ser Val Lys Val Asp Leu Asp Gln Ser Gln Phe Asp Ala
65                  70                  75                  80

Leu Val Ala Trp Thr Phe Asn Leu Gly Pro Gly Asn Leu Arg Ser Ser
                85                  90                  95

Thr Met Leu Lys Lys Leu Asn Asn Gly Glu Tyr Glu Ser Val Pro Phe
            100                 105                 110

Glu Met Arg Arg Trp Asn Lys Ala Gly Gly Lys Thr Leu Asp Gly Leu
        115                 120                 125

Ile Arg Arg Arg Gln Ala Glu Ser Leu Leu Phe Glu Ser Lys Glu Trp
    130                 135                 140

His Gln Val
145

<210> SEQ ID NO 2
<211> LENGTH: 143
<212> TYPE: PRT
<213> ORGANISM: Pseudomonas putida

<400> SEQUENCE: 2

Met Arg Thr Ser Gln Arg Gly Leu Ser Leu Ile Lys Ser Phe Glu Gly
1               5                   10                  15

Leu Arg Leu Gln Ala Tyr Gln Asp Ser Val Gly Val Trp Thr Ile Gly
                20                  25                  30

Tyr Gly Thr Thr Arg Gly Val Lys Ala Gly Met Lys Ile Ser Lys Asp
            35                  40                  45

Gln Ala Glu Arg Met Leu Leu Asn Asp Val Gln Arg Phe Glu Pro Glu
    50                  55                  60

```
Val Glu Arg Leu Ile Lys Val Pro Leu Asn Gln Asp Gln Trp Asp Ala
 65                  70                  75                  80

Leu Met Ser Phe Thr Tyr Asn Leu Gly Ala Ala Asn Leu Glu Ser Ser
                 85                  90                  95

Thr Leu Arg Arg Leu Leu Asn Ala Gly Asn Tyr Ala Ala Ala Ala Glu
            100                 105                 110

Gln Phe Pro Arg Trp Asn Lys Ala Gly Gln Val Leu Ala Gly Leu
            115                 120                 125

Thr Arg Arg Arg Ala Ala Glu Arg Glu Leu Phe Leu Gly Ala Ala
            130                 135                 140
```

<210> SEQ ID NO 3
<211> LENGTH: 144
<212> TYPE: PRT
<213> ORGANISM: Pseudomonas phage PAJU2

<400> SEQUENCE: 3

```
Met Arg Thr Ser Gln Arg Gly Ile Asp Leu Ile Lys Ser Phe Glu Gly
  1               5                  10                  15

Leu Arg Leu Ser Ala Tyr Gln Asp Ser Val Gly Val Trp Thr Ile Gly
                 20                  25                  30

Tyr Gly Thr Thr Arg Gly Val Thr Arg Tyr Met Thr Ile Thr Val Glu
             35                  40                  45

Gln Ala Glu Arg Met Leu Ser Asn Asp Ile Gln Arg Phe Glu Pro Glu
         50                  55                  60

Leu Asp Arg Leu Ala Lys Val Pro Leu Asn Gln Asn Gln Trp Asp Ala
 65                  70                  75                  80

Leu Met Ser Phe Val Tyr Asn Leu Gly Ala Ala Asn Leu Ala Ser Ser
                 85                  90                  95

Thr Leu Leu Lys Leu Leu Asn Lys Gly Asp Tyr Gln Gly Ala Ala Asp
            100                 105                 110

Gln Phe Pro Arg Trp Val Asn Ala Gly Gly Lys Arg Leu Asp Gly Leu
            115                 120                 125

Val Lys Arg Arg Ala Ala Glu Arg Ala Leu Phe Leu Glu Pro Leu Ser
            130                 135                 140
```

<210> SEQ ID NO 4
<211> LENGTH: 144
<212> TYPE: PRT
<213> ORGANISM: Artificial Sequence
<220> FEATURE:
<223> OTHER INFORMATION: SYNTHETIC POLYPEPTIDE

<400> SEQUENCE: 4

```
Met Arg Thr Ser Gln Arg Gly Ile Asp Leu Ile Lys Ser Phe Glu Gly
  1               5                  10                  15

Leu Arg Leu Ser Ala Tyr Gln Asp Ser Val Gly Val Trp Thr Ile Gly
                 20                  25                  30

Tyr Gly Thr Thr Arg Gly Val Thr Arg Tyr Met Thr Ile Thr Val Glu
             35                  40                  45

Gln Ala Glu Arg Met Leu Ser Asn Asp Ile Gln Arg Phe Glu Pro Glu
         50                  55                  60

Leu Asp Arg Leu Ala Lys Val Pro Leu Asn Gln Asn Gln Trp Asp Ala
 65                  70                  75                  80

Leu Met Ser Phe Val Tyr Asn Leu Gly Ala Ala Asn Leu Ala Ser Ser
                 85                  90                  95
```

```
Thr Leu Leu Asp Leu Leu Asn Lys Gly Asp Tyr Gln Gly Ala Ala Asp
            100                 105                 110

Gln Phe Pro His Trp Val Asn Ala Gly Gly Lys Arg Leu Asp Gly Leu
        115                 120                 125

Val Lys Arg Arg Ala Ala Glu Arg Ala Leu Phe Leu Glu Pro Leu Ser
130                 135                 140
```

<210> SEQ ID NO 5
<211> LENGTH: 143
<212> TYPE: PRT
<213> ORGANISM: Artificial Sequence
<220> FEATURE:
<223> OTHER INFORMATION: SYNTHETIC POLYPEPTIDE

<400> SEQUENCE: 5

```
Met Arg Thr Ser Gln Arg Gly Leu Ser Leu Ile Lys Ser Phe Glu Gly
1               5                   10                  15

Leu Arg Leu Gln Ala Tyr Gln Asp Ser Val Gly Val Trp Thr Ile Gly
            20                  25                  30

Tyr Gly Thr Thr Arg Gly Val Lys Ala Gly Met Lys Ile Ser Lys Asp
        35                  40                  45

Gln Ala Glu Arg Met Leu Leu Asn Asp Val Gln Arg Phe Glu Pro Glu
    50                  55                  60

Val Glu Arg Leu Ile Lys Val Pro Leu Asn Gln Asp Gln Trp Asp Ala
65                  70                  75                  80

Leu Met Ser Phe Thr Tyr Asn Leu Gly Ala Ala Asn Leu Glu Ser Ser
                85                  90                  95

Thr Leu Arg Asp Leu Leu Asn Ala Gly Asn Tyr Ala Ala Ala Ala Glu
            100                 105                 110

Gln Phe Pro His Trp Asn Lys Ala Gly Gly Gln Val Leu Ala Gly Leu
        115                 120                 125

Thr Arg Arg Arg Ala Ala Glu Arg Glu Leu Phe Leu Gly Ala Ala
    130                 135                 140
```

<210> SEQ ID NO 6
<211> LENGTH: 158
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 6

```
Gly Pro Arg Arg Pro Arg Arg Pro Gly Arg Arg Ala Pro Val Met Arg
1               5                   10                  15

Thr Ser Gln Arg Gly Ile Asp Leu Ile Lys Ser Phe Glu Gly Leu Arg
            20                  25                  30

Leu Ser Ala Tyr Gln Asp Ser Val Gly Val Trp Thr Ile Gly Tyr Gly
        35                  40                  45

Thr Thr Arg Gly Val Thr Arg Tyr Met Thr Ile Thr Val Glu Gln Ala
    50                  55                  60

Glu Arg Met Leu Ser Asn Asp Ile Gln Arg Phe Glu Pro Glu Leu Asp
65                  70                  75                  80

Arg Leu Ala Lys Val Pro Leu Asn Gln Asn Gln Trp Asp Ala Leu Met
                85                  90                  95

Ser Phe Val Tyr Asn Leu Gly Ala Ala Asn Leu Ala Ser Ser Thr Leu
            100                 105                 110

Leu Lys Leu Leu Asn Lys Gly Asp Tyr Gln Gly Ala Ala Asp Gln Phe
        115                 120                 125
```

Pro Arg Trp Val Asn Ala Gly Gly Lys Arg Leu Asp Gly Leu Val Lys
        130                 135                 140

Arg Arg Ala Ala Glu Arg Ala Leu Phe Leu Glu Pro Leu Ser
145                 150                 155

<210> SEQ ID NO 7
<211> LENGTH: 172
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 7

Lys Phe Phe Lys Phe Phe Lys Phe Phe Lys Ala Gly Ala Gly Ala Gly
1               5                   10                  15

Ala Gly Ala Gly Ala Gly Ala Gly Ala Ser Met Arg Thr Ser
            20                  25                  30

Gln Arg Gly Ile Asp Leu Ile Lys Ser Phe Glu Gly Leu Arg Leu Ser
        35                  40                  45

Ala Tyr Gln Asp Ser Val Gly Val Trp Thr Ile Gly Tyr Gly Thr Thr
    50                  55                  60

Arg Gly Val Thr Arg Tyr Met Thr Ile Thr Val Glu Gln Ala Glu Arg
65                  70                  75                  80

Met Leu Ser Asn Asp Ile Gln Arg Phe Glu Pro Glu Leu Asp Arg Leu
                85                  90                  95

Ala Lys Val Pro Leu Asn Gln Asn Gln Trp Asp Ala Leu Met Ser Phe
            100                 105                 110

Val Tyr Asn Leu Gly Ala Ala Asn Leu Ala Ser Ser Thr Leu Leu Lys
        115                 120                 125

Leu Leu Asn Lys Gly Asp Tyr Gln Gly Ala Ala Asp Gln Phe Pro Arg
    130                 135                 140

Trp Val Asn Ala Gly Gly Lys Arg Leu Asp Gly Leu Val Lys Arg Arg
145                 150                 155                 160

Ala Ala Glu Arg Ala Leu Phe Leu Glu Pro Leu Ser
                165                 170

<210> SEQ ID NO 8
<211> LENGTH: 171
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 8

Lys Arg Lys Lys Arg Lys Lys Arg Lys Ala Gly Ala Gly Ala Gly Ala
1               5                   10                  15

Gly Ala Gly Ala Gly Ala Gly Ala Ser Met Arg Thr Ser Gln
            20                  25                  30

Arg Gly Ile Asp Leu Ile Lys Ser Phe Glu Gly Leu Arg Leu Ser Ala
        35                  40                  45

Tyr Gln Asp Ser Val Gly Val Trp Thr Ile Gly Tyr Gly Thr Thr Arg
    50                  55                  60

Gly Val Thr Arg Tyr Met Thr Ile Thr Val Glu Gln Ala Glu Arg Met
65                  70                  75                  80

Leu Ser Asn Asp Ile Gln Arg Phe Glu Pro Glu Leu Asp Arg Leu Ala
                85                  90                  95

Lys Val Pro Leu Asn Gln Asn Gln Trp Asp Ala Leu Met Ser Phe Val

```
                    100                 105                 110
Tyr Asn Leu Gly Ala Ala Asn Leu Ala Ser Ser Thr Leu Leu Lys Leu
                115                 120                 125

Leu Asn Lys Gly Asp Tyr Gln Gly Ala Ala Asp Gln Phe Pro Arg Trp
    130                 135                 140

Val Asn Ala Gly Gly Lys Arg Leu Asp Gly Leu Val Lys Arg Arg Ala
145                 150                 155                 160

Ala Glu Arg Ala Leu Phe Leu Glu Pro Leu Ser
                165                 170
```

<210> SEQ ID NO 9
<211> LENGTH: 158
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 9

```
Met Arg Thr Ser Gln Arg Gly Ile Asp Leu Ile Lys Ser Phe Glu Gly
1               5                   10                  15

Leu Arg Leu Ser Ala Tyr Gln Asp Ser Val Gly Val Trp Thr Ile Gly
                20                  25                  30

Tyr Gly Thr Thr Arg Gly Val Thr Arg Tyr Met Thr Ile Thr Val Glu
            35                  40                  45

Gln Ala Glu Arg Met Leu Ser Asn Asp Ile Gln Arg Phe Glu Pro Glu
        50                  55                  60

Leu Asp Arg Leu Ala Lys Val Pro Leu Asn Gln Asn Gln Trp Asp Ala
65                  70                  75                  80

Leu Met Ser Phe Val Tyr Asn Leu Gly Ala Ala Asn Leu Ala Ser Ser
                85                  90                  95

Thr Leu Leu Asp Leu Leu Asn Lys Gly Asp Tyr Gln Gly Ala Ala Asp
            100                 105                 110

Gln Phe Pro His Trp Val Asn Ala Gly Gly Lys Arg Leu Asp Gly Leu
        115                 120                 125

Val Lys Arg Arg Ala Ala Glu Arg Ala Leu Phe Leu Glu Pro Leu Ser
    130                 135                 140

Gly Pro Arg Arg Pro Arg Pro Gly Arg Arg Ala Pro Val
145                 150                 155
```

<210> SEQ ID NO 10
<211> LENGTH: 181
<212> TYPE: PRT
<213> ORGANISM: Pseudomonas phage Lu11

<400> SEQUENCE: 10

```
Met Asn Asn Glu Leu Pro Trp Val Ala Glu Ala Arg Lys Tyr Ile Gly
1               5                   10                  15

Leu Arg Glu Asp Thr Ser Lys Thr Ser His Asn Pro Lys Leu Leu Ala
                20                  25                  30

Met Leu Asp Arg Met Gly Glu Phe Ser Asn Glu Ser Arg Ala Trp Trp
            35                  40                  45

His Asp Asp Glu Thr Pro Trp Cys Gly Leu Phe Val Gly Tyr Cys Leu
        50                  55                  60

Gly Val Ala Gly Arg Tyr Val Val Arg Glu Trp Tyr Arg Ala Arg Ala
65                  70                  75                  80

Trp Glu Ala Pro Gln Leu Thr Lys Leu Asp Arg Pro Ala Tyr Gly Ala
                85                  90                  95
```

```
Leu Val Thr Phe Thr Arg Ser Gly Gly Gly His Val Gly Phe Ile Val
            100                 105                 110

Gly Lys Asp Ala Arg Gly Asn Leu Met Val Leu Gly Gly Asn Gln Ser
            115                 120                 125

Asn Ala Val Ser Ile Ala Pro Phe Ala Val Ser Arg Val Thr Gly Tyr
        130                 135                 140

Phe Trp Pro Ser Phe Trp Arg Asn Lys Thr Ala Val Lys Ser Val Pro
145                 150                 155                 160

Phe Glu Glu Arg Tyr Ser Leu Pro Leu Leu Lys Ser Asn Gly Glu Leu
                165                 170                 175

Ser Thr Asn Glu Ala
            180

<210> SEQ ID NO 11
<211> LENGTH: 439
<212> TYPE: PRT
<213> ORGANISM: Pseudomonas sp.

<400> SEQUENCE: 11

Met Lys Arg Thr Thr Leu Asn Leu Glu Leu Glu Ser Asn Thr Asp Arg
1               5                   10                  15

Leu Leu Gln Glu Lys Asp Asp Leu Leu Pro Gln Ser Val Thr Asn Ser
            20                  25                  30

Ser Asp Glu Gly Thr Pro Phe Ala Gln Val Glu Gly Ala Ser Asp Asp
        35                  40                  45

Asn Thr Ala Glu Gln Asp Ser Asp Lys Pro Gly Ala Ser Val Ala Asp
50                  55                  60

Ala Asp Thr Lys Pro Val Asp Pro Glu Trp Lys Thr Ile Thr Val Ala
65                  70                  75                  80

Ser Gly Asp Thr Leu Ser Thr Val Phe Thr Lys Ala Gly Leu Ser Thr
                85                  90                  95

Ser Ala Met His Asp Met Leu Thr Ser Ser Lys Asp Ala Lys Arg Phe
            100                 105                 110

Thr His Leu Lys Val Gly Gln Glu Val Lys Leu Lys Leu Asp Pro Lys
        115                 120                 125

Gly Glu Leu Gln Ala Leu Arg Val Lys Gln Ser Glu Leu Glu Thr Ile
130                 135                 140

Gly Leu Asp Lys Thr Asp Lys Gly Tyr Ser Phe Lys Arg Glu Lys Ala
145                 150                 155                 160

Gln Ile Asp Leu His Thr Ala Tyr Ala His Gly Arg Ile Thr Ser Ser
                165                 170                 175

Leu Phe Val Ala Gly Arg Asn Ala Gly Leu Pro Tyr Asn Leu Val Thr
            180                 185                 190

Ser Leu Ser Asn Ile Phe Gly Tyr Asp Ile Asp Phe Ala Leu Asp Leu
        195                 200                 205

Arg Glu Gly Asp Glu Phe Asp Val Ile Tyr Glu Gln His Lys Val Asn
210                 215                 220

Gly Lys Gln Val Ala Thr Gly Asn Ile Leu Ala Ala Arg Phe Val Asn
225                 230                 235                 240

Arg Gly Lys Thr Tyr Thr Ala Val Arg Tyr Thr Asn Lys Gln Gly Asn
                245                 250                 255

Thr Ser Tyr Tyr Arg Ala Asp Gly Ser Ser Met Arg Lys Ala Phe Ile
            260                 265                 270

Arg Thr Pro Val Asp Phe Ala Arg Ile Ser Ser Arg Phe Ser Leu Gly
```

```
                    275                 280                 285
Arg Arg His Pro Ile Leu Asn Lys Ile Arg Ala His Lys Gly Val Asp
    290                 295                 300

Tyr Ala Ala Pro Ile Gly Thr Pro Ile Lys Ala Thr Gly Asp Gly Lys
305                 310                 315                 320

Ile Leu Glu Ala Gly Arg Lys Gly Gly Tyr Gly Asn Ala Val Val Ile
                325                 330                 335

Gln His Gly Gln Arg Tyr Arg Thr Ile Tyr Gly His Met Ser Arg Phe
            340                 345                 350

Ala Lys Gly Ile Arg Ala Gly Thr Ser Val Lys Gln Gly Gln Ile Ile
        355                 360                 365

Gly Tyr Val Gly Met Thr Gly Leu Ala Thr Gly Pro His Leu His Tyr
    370                 375                 380

Glu Phe Gln Ile Asn Gly Arg His Val Asp Pro Leu Ser Ala Lys Leu
385                 390                 395                 400

Pro Met Ala Asp Pro Leu Gly Gly Ala Asp Arg Lys Arg Phe Met Ala
                405                 410                 415

Gln Thr Gln Pro Met Ile Ala Arg Met Asp Gln Glu Lys Lys Thr Leu
            420                 425                 430

Leu Ala Leu Asn Lys Gln Arg
            435

<210> SEQ ID NO 12
<211> LENGTH: 126
<212> TYPE: PRT
<213> ORGANISM: Micavibrio aeruginosavorus

<400> SEQUENCE: 12

Met Thr Tyr Thr Leu Ser Lys Arg Ser Leu Asp Asn Leu Lys Gly Val
1               5                   10                  15

His Pro Asp Leu Val Ala Val Val His Arg Ala Ile Gln Leu Thr Pro
            20                  25                  30

Val Asp Phe Ala Val Ile Glu Gly Leu Arg Ser Val Ser Arg Gln Lys
        35                  40                  45

Glu Leu Val Ala Ala Gly Ala Ser Lys Thr Met Asn Ser Arg His Leu
    50                  55                  60

Thr Gly His Ala Val Asp Leu Ala Ala Tyr Val Asn Gly Ile Arg Trp
65                  70                  75                  80

Asp Trp Pro Leu Tyr Asp Ala Ile Ala Val Ala Val Lys Ala Ala Ala
                85                  90                  95

Lys Glu Leu Gly Val Ala Ile Val Trp Gly Gly Asp Trp Thr Thr Phe
            100                 105                 110

Lys Asp Gly Pro His Phe Glu Leu Asp Arg Ser Lys Tyr Arg
        115                 120                 125

<210> SEQ ID NO 13
<211> LENGTH: 144
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 13

Met Thr Tyr Thr Leu Ser Lys Arg Ser Leu Asp Asn Leu Lys Gly Val
1               5                   10                  15

His Pro Asp Leu Val Ala Val Val His Arg Ala Ile Gln Leu Thr Pro
            20                  25                  30
```

```
Val Asp Phe Ala Val Ile Glu Gly Leu Arg Ser Val Arg Gln Lys
            35                  40                  45

Glu Leu Val Ala Ala Gly Ala Ser Lys Thr Met Asn Ser Arg His Leu
 50                  55                  60

Thr Gly His Ala Val Asp Leu Ala Ala Tyr Val Asn Gly Ile Arg Trp
 65                  70                  75                  80

Asp Trp Pro Leu Tyr Asp Ala Ile Ala Val Ala Val Lys Ala Ala Ala
                 85                  90                  95

Lys Glu Leu Gly Val Ala Ile Val Trp Gly Gly Asp Trp Thr Thr Phe
                100                 105                 110

Lys Asp Gly Pro His Phe Glu Leu Asp Arg Ser Lys Tyr Arg Arg Lys
                115                 120                 125

Lys Thr Arg Lys Arg Leu Lys Lys Ile Gly Lys Val Leu Lys Trp Ile
            130                 135                 140
```

<210> SEQ ID NO 14
<211> LENGTH: 154
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 14

```
Lys Phe Phe Lys Phe Phe Lys Phe Phe Lys Ala Gly Ala Gly Ala Gly
 1               5                  10                  15

Ala Gly Ala Gly Ala Gly Ala Gly Ala Ser Met Thr Tyr Thr
                 20                  25                  30

Leu Ser Lys Arg Ser Leu Asp Asn Leu Lys Gly Val His Pro Asp Leu
            35                  40                  45

Val Ala Val Val His Arg Ala Ile Gln Leu Thr Pro Val Asp Phe Ala
 50                  55                  60

Val Ile Glu Gly Leu Arg Ser Val Ser Arg Gln Lys Glu Leu Val Ala
 65                  70                  75                  80

Ala Gly Ala Ser Lys Thr Met Asn Ser Arg His Leu Thr Gly His Ala
                 85                  90                  95

Val Asp Leu Ala Ala Tyr Val Asn Gly Ile Arg Trp Asp Trp Pro Leu
                100                 105                 110

Tyr Asp Ala Ile Ala Val Ala Val Lys Ala Ala Ala Lys Glu Leu Gly
            115                 120                 125

Val Ala Ile Val Trp Gly Gly Asp Trp Thr Thr Phe Lys Asp Gly Pro
 130                 135                 140

His Phe Glu Leu Asp Arg Ser Lys Tyr Arg
145                 150
```

<210> SEQ ID NO 15
<211> LENGTH: 157
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 15

```
Met Arg Thr Ser Gln Arg Gly Leu Ser Leu Ile Lys Ser Phe Glu Gly
 1               5                  10                  15

Leu Arg Leu Gln Ala Tyr Gln Asp Ser Val Gly Val Trp Thr Ile Gly
            20                  25                  30

Tyr Gly Thr Thr Arg Gly Val Lys Ala Gly Met Lys Ile Ser Lys Asp
```

```
                        35                  40                  45

Gln Ala Glu Arg Met Leu Leu Asn Asp Val Gln Arg Phe Glu Pro Glu
         50                  55                  60

Val Glu Arg Leu Ile Lys Val Pro Leu Asn Gln Asp Gln Trp Asp Ala
 65                  70                  75                  80

Leu Met Ser Phe Thr Tyr Asn Leu Gly Ala Ala Asn Leu Glu Ser Ser
                 85                  90                  95

Thr Leu Arg Asp Leu Leu Asn Ala Gly Asn Tyr Ala Ala Ala Ala Glu
            100                 105                 110

Gln Phe Pro His Trp Asn Lys Ala Gly Gln Val Leu Ala Gly Leu
        115                 120                 125

Thr Arg Arg Arg Ala Ala Glu Arg Glu Leu Phe Leu Gly Ala Ala Gly
        130                 135                 140

Pro Arg Arg Pro Arg Arg Pro Gly Arg Arg Ala Pro Val
145                 150                 155

<210> SEQ ID NO 16
<211> LENGTH: 157
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 16

Gly Pro Arg Arg Pro Arg Arg Pro Gly Arg Arg Ala Pro Val Met Arg
 1               5                  10                  15

Thr Ser Gln Arg Gly Leu Ser Leu Ile Lys Ser Phe Glu Gly Leu Arg
             20                  25                  30

Leu Gln Ala Tyr Gln Asp Ser Val Gly Val Trp Thr Ile Gly Tyr Gly
         35                  40                  45

Thr Thr Arg Gly Val Lys Ala Gly Met Lys Ile Ser Lys Asp Gln Ala
     50                  55                  60

Glu Arg Met Leu Leu Asn Asp Val Gln Arg Phe Glu Pro Glu Val Glu
 65                  70                  75                  80

Arg Leu Ile Lys Val Pro Leu Asn Gln Asp Gln Trp Asp Ala Leu Met
                 85                  90                  95

Ser Phe Thr Tyr Asn Leu Gly Ala Ala Asn Leu Glu Ser Ser Thr Leu
            100                 105                 110

Arg Arg Leu Leu Asn Ala Gly Asn Tyr Ala Ala Ala Ala Glu Gln Phe
        115                 120                 125

Pro Arg Trp Asn Lys Ala Gly Gly Gln Val Leu Ala Gly Leu Thr Arg
    130                 135                 140

Arg Arg Ala Ala Glu Arg Glu Leu Phe Leu Gly Ala Ala
145                 150                 155

<210> SEQ ID NO 17
<211> LENGTH: 150
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 17

Met Ser Phe Lys Leu Gly Lys Arg Ser Leu Ser Asn Leu Glu Gly Val
 1               5                  10                  15

His Pro Asp Leu Ile Lys Val Val Lys Arg Ala Ile Glu Leu Thr Glu
             20                  25                  30
```

```
Cys Asp Phe Thr Val Thr Glu Gly Leu Arg Ser Lys Glu Arg Gln Ala
             35                  40                  45

Gln Leu Leu Lys Glu Lys Lys Thr Thr Thr Ser Asn Ser Arg His Leu
 50                      55                  60

Thr Gly His Ala Val Asp Leu Ala Ala Trp Val Asn Asn Thr Val Ser
 65                  70                  75                  80

Trp Asp Trp Lys Tyr Tyr Gln Ile Ala Asp Ala Met Lys Lys Ala
                 85                  90                  95

Ala Ser Glu Leu Asn Val Ser Ile Asp Trp Gly Asp Trp Lys Lys
            100                 105                 110

Phe Lys Asp Gly Pro His Phe Glu Leu Thr Trp Ser Lys Tyr Pro Ile
            115                 120                 125

Lys Gly Ala Ser Arg Lys Lys Thr Arg Lys Arg Leu Lys Lys Ile Gly
            130                 135                 140

Lys Val Leu Lys Trp Ile
145                 150

<210> SEQ ID NO 18
<211> LENGTH: 134
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 18

Met Lys Leu Ser Glu Lys Arg Ala Leu Phe Thr Gln Leu Leu Ala Gln
 1               5                  10                  15

Leu Ile Leu Trp Ala Gly Thr Gln Asp Arg Val Ser Val Ala Leu Asp
                20                  25                  30

Gln Val Lys Arg Thr Gln Ala Glu Ala Asp Ala Asn Ala Lys Ser Gly
            35                  40                  45

Ala Gly Ile Arg Asn Ser Leu His Leu Gly Leu Ala Gly Asp Leu
 50                  55                  60

Ile Leu Tyr Lys Asp Gly Lys Tyr Met Asp Lys Ser Glu Asp Tyr Lys
 65                  70                  75                  80

Phe Leu Gly Asp Tyr Trp Lys Ser Leu His Pro Leu Cys Arg Trp Gly
                 85                  90                  95

Gly Asp Phe Lys Ser Arg Pro Asp Gly Asn His Phe Ser Leu Glu His
            100                 105                 110

Glu Gly Val Gln Arg Lys Lys Thr Arg Lys Arg Leu Lys Lys Ile Gly
            115                 120                 125

Lys Val Leu Lys Trp Ile
        130

<210> SEQ ID NO 19
<211> LENGTH: 132
<212> TYPE: PRT
<213> ORGANISM: Acinetobacter sp.

<400> SEQUENCE: 19

Met Ser Phe Lys Leu Gly Lys Arg Ser Leu Ser Asn Leu Glu Gly Val
 1               5                  10                  15

His Pro Asp Leu Ile Lys Val Val Lys Arg Ala Ile Glu Leu Thr Glu
                20                  25                  30

Cys Asp Phe Thr Val Thr Glu Gly Leu Arg Ser Lys Glu Arg Gln Ala
            35                  40                  45

Gln Leu Leu Lys Glu Lys Lys Thr Thr Thr Ser Asn Ser Arg His Leu
```

```
                  50                  55                  60

Thr Gly His Ala Val Asp Leu Ala Ala Trp Val Asn Asn Thr Val Ser
 65                  70                  75                  80

Trp Asp Trp Lys Tyr Tyr Gln Ile Ala Asp Ala Met Lys Lys Ala
                 85                  90                  95

Ala Ser Glu Leu Asn Val Ser Ile Asp Trp Gly Asp Trp Lys Lys
                100                 105                 110

Phe Lys Asp Gly Pro His Phe Glu Leu Thr Trp Ser Lys Tyr Pro Ile
                115                 120                 125

Lys Gly Ala Ser
    130
```

<210> SEQ ID NO 20
<211> LENGTH: 116
<212> TYPE: PRT
<213> ORGANISM: Pseudomonas phage PaP2

<400> SEQUENCE: 20

```
Met Lys Leu Ser Glu Lys Arg Ala Leu Phe Thr Gln Leu Leu Ala Gln
 1               5                  10                  15

Leu Ile Leu Trp Ala Gly Thr Gln Asp Arg Val Ser Val Ala Leu Asp
                 20                  25                  30

Gln Val Lys Arg Thr Gln Ala Glu Ala Asp Ala Asn Ala Lys Ser Gly
                 35                  40                  45

Ala Gly Ile Arg Asn Ser Leu His Leu Leu Gly Leu Ala Gly Asp Leu
     50                  55                  60

Ile Leu Tyr Lys Asp Gly Lys Tyr Met Asp Lys Ser Glu Asp Tyr Lys
 65                  70                  75                  80

Phe Leu Gly Asp Tyr Trp Lys Ser Leu His Pro Leu Cys Arg Trp Gly
                 85                  90                  95

Gly Asp Phe Lys Ser Arg Pro Asp Gly Asn His Phe Ser Leu Glu His
                100                 105                 110

Glu Gly Val Gln
    115
```

<210> SEQ ID NO 21
<211> LENGTH: 157
<212> TYPE: PRT
<213> ORGANISM: UNKNOWN
<220> FEATURE:
<223> OTHER INFORMATION: Marine metagenome

<400> SEQUENCE: 21

```
Met Lys Asn Phe Asn Glu Ile Ile Glu His Val Leu Lys His Glu Gly
 1               5                  10                  15

Gly Tyr Val Asn Asp Pro Lys Asp Leu Gly Gly Glu Thr Lys Tyr Gly
                 20                  25                  30

Ile Thr Lys Arg Phe Tyr Pro Asp Leu Asp Ile Lys Asn Leu Thr Ile
                 35                  40                  45

Glu Gln Ala Thr Glu Ile Tyr Lys Lys Asp Tyr Trp Asp Lys Asn Lys
     50                  55                  60

Val Glu Ser Leu Pro Gln Asn Leu Trp His Ile Tyr Phe Asp Met Cys
 65                  70                  75                  80

Val Asn Met Gly Lys Arg Thr Ala Val Lys Val Leu Gln Arg Ala Ala
                 85                  90                  95

Val Asn Arg Gly Arg Asp Ile Glu Val Asp Gly Gly Leu Gly Pro Ala
                100                 105                 110
```

```
Thr Ile Gly Ala Leu Lys Gly Val Glu Leu Asp Arg Val Arg Ala Phe
        115                 120                 125

Arg Val Lys Tyr Tyr Val Asp Leu Ile Thr Ala Arg Pro Glu Gln Glu
130                 135                 140

Lys Phe Tyr Leu Gly Trp Phe Arg Arg Ala Thr Glu Val
145                 150                 155

<210> SEQ ID NO 22
<211> LENGTH: 231
<212> TYPE: PRT
<213> ORGANISM: Pseudomonas phage phi2954

<400> SEQUENCE: 22

Met Ser Lys Gln Gly Gly Val Lys Val Ala Gln Ala Val Ala Ala Leu
1               5                   10                  15

Ser Ser Pro Gly Leu Lys Ile Asp Gly Ile Val Gly Lys Ala Thr Arg
            20                  25                  30

Ala Ala Val Ser Ser Met Pro Ser Ser Gln Lys Ala Ala Thr Asp Lys
        35                  40                  45

Ile Leu Gln Ser Ala Gly Ile Gly Ser Leu Asp Ser Leu Leu Ala Glu
50                  55                  60

Pro Ala Ala Ala Thr Ser Asp Thr Phe Arg Glu Val Val Leu Ala Val
65                  70                  75                  80

Ala Arg Glu Ala Arg Lys Arg Gly Leu Asn Pro Ala Phe Tyr Val Ala
                85                  90                  95

His Ile Ala Leu Glu Thr Gly Trp Gly Arg Ser Val Pro Lys Leu Pro
            100                 105                 110

Asp Gly Arg Ser Ser Tyr Asn Tyr Ala Gly Leu Lys Tyr Ala Ala Val
        115                 120                 125

Lys Thr Gln Val Lys Gly Lys Thr Glu Thr Asn Thr Leu Glu Tyr Ile
130                 135                 140

Lys Ser Leu Pro Lys Thr Val Arg Asp Ser Phe Ala Val Phe Ala Ser
145                 150                 155                 160

Ala Gly Asp Phe Ser Arg Val Tyr Phe Trp Tyr Leu Leu Asp Ser Pro
                165                 170                 175

Ser Ala Tyr Arg Tyr Pro Gly Leu Lys Asn Ala Lys Thr Ala Gln Glu
            180                 185                 190

Phe Gly Asp Ile Leu Gln Lys Gly Gly Tyr Ala Thr Asp Pro Ala Tyr
        195                 200                 205

Ala Ala Lys Val Ala Ser Ile Ala Ser Thr Ala Val Ala Arg Tyr Gly
    210                 215                 220

Ser Asp Val Ser Ser Val Ala
225                 230

<210> SEQ ID NO 23
<211> LENGTH: 202
<212> TYPE: PRT
<213> ORGANISM: Pseudomonas phage Lu11

<400> SEQUENCE: 23

Met Ser Asp Lys Arg Val Glu Ile Thr Gly Asn Val Ser Gly Phe Phe
1               5                   10                  15

Glu Ser Gly Gly Arg Gly Val Lys Thr Val Ser Thr Gly Lys Gly Asp
            20                  25                  30

Asn Gly Gly Val Ser Tyr Gly Lys His Gln Leu Ala Ser Asn Asn Gly
        35                  40                  45
```

Ser Met Ala Leu Phe Leu Glu Ser Pro Phe Gly Ala Pro Tyr Arg Ala
            50                  55                  60

Gln Phe Ala Gly Leu Lys Pro Gly Thr Ala Ala Phe Thr Ser Val Tyr
 65                  70                  75                  80

Asn Lys Ile Ala Asn Glu Thr Pro Thr Ala Phe Glu Arg Asp Gln Phe
                    85                  90                  95

Gln Tyr Ile Ala Ala Ser His Tyr Asp Pro Gln Ala Ala Lys Leu Lys
                100                 105                 110

Ala Glu Gly Ile Asn Val Asp Asp Arg His Val Ala Val Arg Glu Cys
                115                 120                 125

Val Phe Ser Val Ala Val Gln Tyr Gly Arg Asn Thr Ser Ile Ile Ile
            130                 135                 140

Lys Ala Leu Gly Ser Asn Phe Arg Gly Ser Asp Lys Asp Phe Ile Glu
145                 150                 155                 160

Lys Val Gln Asp Tyr Arg Gly Ala Thr Val Asn Thr Tyr Phe Lys Ser
                165                 170                 175

Ser Ser Gln Gln Thr Arg Asp Ser Val Lys Asn Arg Ser Gln Gln Glu
                180                 185                 190

Lys Gln Met Leu Leu Lys Leu Leu Asn Ser
                195                 200

<210> SEQ ID NO 24
<211> LENGTH: 268
<212> TYPE: PRT
<213> ORGANISM: Pseudomonas aeruginosa

<400> SEQUENCE: 24

Met Thr Leu Arg Tyr Gly Asp Arg Ser Gln Glu Val Arg Gln Leu Gln
 1               5                  10                  15

Arg Arg Leu Asn Thr Trp Ala Gly Ala Asn Leu Tyr Glu Asp Gly His
                20                  25                  30

Phe Gly Ala Ala Thr Glu Asp Ala Val Arg Ala Phe Gln Arg Ser His
            35                  40                  45

Gly Leu Val Ala Asp Gly Ile Ala Gly Pro Lys Thr Leu Ala Ala Leu
 50                  55                  60

Gly Gly Ala Asp Cys Ser His Leu Leu Gln Asn Ala Asp Leu Val Ala
 65                  70                  75                  80

Ala Ala Thr Arg Leu Gly Leu Pro Leu Ala Thr Ile Tyr Ala Val Asn
                    85                  90                  95

Gln Val Glu Ser Asn Gly Gln Gly Phe Leu Gly Asn Gly Lys Pro Ala
                100                 105                 110

Ile Leu Phe Glu Arg His Ile Met Tyr Arg Arg Leu Ala Ala His Asp
                115                 120                 125

Gln Val Thr Ala Asp Gln Leu Ala Ala Gln Phe Pro Ala Leu Val Asn
            130                 135                 140

Pro Arg Pro Gly Gly Tyr Ala Gly Gly Thr Ala Glu His Gln Arg Leu
145                 150                 155                 160

Ala Asn Ala Arg Gln Ile Asp Asp Thr Ala Leu Glu Ser Ala Ser
                165                 170                 175

Trp Gly Ala Phe Gln Ile Met Gly Phe His Trp Gln Arg Leu Gly Tyr
            180                 185                 190

Ile Ser Val Gln Ala Phe Ala Glu Ala Met Gly Arg Ser Glu Ser Ala
        195                 200                 205

Gln Phe Glu Ala Phe Val Arg Phe Ile Asp Thr Asp Pro Ala Leu His

Lys Ala Leu Lys Ala Arg Lys Trp Ala Asp Phe Ala Arg Leu Tyr Asn
225                 230                 235                 240

Gly Pro Asp Tyr Lys Arg Asn Leu Tyr Asp Asn Lys Leu Ala Arg Ala
            245                 250                 255

Tyr Glu Gln His Ala Asn Cys Ala Glu Ala Ser Ala
        260                 265

<210> SEQ ID NO 25
<211> LENGTH: 160
<212> TYPE: PRT
<213> ORGANISM: Pseudomonas aeruginosa

<400> SEQUENCE: 25

Met Ala Val Val Ser Glu Lys Thr Ala Gly Gly Arg Asn Val Leu Ala
1               5                   10                  15

Phe Leu Asp Met Leu Ala Trp Ser Glu Gly Thr Ser Thr Ile Arg Gly
            20                  25                  30

Ser Asp Asn Gly Tyr Asn Val Val Gly Gly Leu Phe Asn Gly
        35                  40                  45

Tyr Ala Asp His Pro Arg Leu Lys Val Tyr Leu Pro Arg Tyr Lys Val
50                  55                  60

Tyr Ser Thr Ala Ala Gly Arg Tyr Gln Leu Leu Ser Arg Tyr Trp Asp
65                  70                  75                  80

Ala Tyr Arg Glu Ser Leu Ala Leu Lys Gly Gly Phe Thr Pro Ser Asn
                85                  90                  95

Gln Asp Leu Val Ala Leu Gln Ile Lys Glu Arg Arg Ser Leu Ala
            100                 105                 110

Asp Ile Gln Ala Gly Arg Leu Ala Asp Ala Val Gln Lys Cys Ser Asn
        115                 120                 125

Ile Trp Ala Ser Leu Pro Gly Ala Gly Tyr Gly Gln Arg Glu His Ser
130                 135                 140

Leu Asp Asp Leu Thr Ala His Tyr Leu Ala Ala Gly Gly Val Leu Ser
145                 150                 155                 160

<210> SEQ ID NO 26
<211> LENGTH: 185
<212> TYPE: PRT
<213> ORGANISM: Acinetobacter phage phiAB6

<400> SEQUENCE: 26

Met Ile Leu Thr Lys Asp Gly Phe Ser Ile Ile Arg Asn Glu Leu Phe
1               5                   10                  15

Glu Gly Lys Leu Asp Gln Thr Gln Val Asp Ala Ile Asn Phe Ile Val
            20                  25                  30

Glu Lys Ala Thr Glu Tyr Gly Leu Thr Tyr Pro Glu Ala Ala Tyr Leu
        35                  40                  45

Leu Ala Thr Ile Tyr His Glu Thr Gly Leu Pro Ser Gly Tyr Arg Thr
    50                  55                  60

Met Gln Pro Ile Lys Glu Ala Gly Ser Asp Ser Tyr Leu Arg Ser Lys
65                  70                  75                  80

Lys Tyr Tyr Pro Tyr Ile Gly Tyr Gly Tyr Val Gln Leu Thr Trp Glu
                85                  90                  95

Glu Asn Tyr Glu Arg Ile Gly Lys Leu Ile Gly Ile Asp Leu Val Lys
            100                 105                 110

Asn Pro Glu Lys Ala Leu Glu Pro Leu Ile Ala Ile Gln Ile Ala Ile

```
                115                 120                 125
Lys Gly Met Leu Asn Gly Trp Phe Thr Gly Val Gly Phe Arg Arg Lys
            130                 135                 140

Arg Pro Val Ser Lys Tyr Asn Lys Gln Gln Tyr Val Ala Ala Arg Asn
145                 150                 155                 160

Ile Ile Asn Gly Lys Asp Lys Ala Glu Leu Ile Ala Lys Tyr Ala Ile
                165                 170                 175

Ile Phe Glu Arg Ala Leu Arg Ser Leu
                180                 185

<210> SEQ ID NO 27
<211> LENGTH: 266
<212> TYPE: PRT
<213> ORGANISM: Pseudomonas phage PhiPA3

<400> SEQUENCE: 27

Met Thr Leu Leu Lys Lys Gly Asp Lys Gly Asp Ala Val Lys Gln Leu
1               5                   10                  15

Gln Gln Lys Leu Lys Asp Leu Gly Tyr Thr Leu Gly Val Asp Gly Asn
                20                  25                  30

Phe Gly Asn Gly Thr Asp Thr Val Val Arg Ser Phe Gln Thr Lys Met
            35                  40                  45

Lys Leu Ser Val Asp Gly Val Val Gly Asn Gly Thr Met Ser Thr Ile
50                  55                  60

Asp Ser Thr Leu Ala Gly Ile Lys Ala Trp Lys Thr Ser Val Pro Phe
65                  70                  75                  80

Pro Ala Thr Asn Lys Ser Arg Ala Met Ala Met Pro Thr Leu Thr Glu
                85                  90                  95

Ile Gly Arg Leu Thr Asn Val Asp Pro Lys Leu Leu Ala Thr Phe Cys
            100                 105                 110

Ser Ile Glu Ser Ala Phe Asp Tyr Thr Ala Lys Pro Tyr Lys Pro Asp
        115                 120                 125

Gly Thr Val Tyr Ser Ser Ala Glu Gly Trp Phe Gln Phe Leu Asp Ala
    130                 135                 140

Thr Trp Asp Asp Glu Val Arg Lys His Gly Lys Gln Tyr Ser Phe Pro
145                 150                 155                 160

Val Asp Pro Gly Arg Ser Leu Arg Lys Asp Pro Arg Ala Asn Gly Leu
                165                 170                 175

Met Gly Ala Glu Phe Leu Lys Gly Asn Ala Ala Ile Leu Arg Pro Val
            180                 185                 190

Leu Gly His Glu Pro Ser Asp Thr Asp Leu Tyr Leu Ala His Phe Met
        195                 200                 205

Gly Ala Gly Gly Ala Lys Gln Phe Leu Met Ala Asp Gln Asn Lys Leu
    210                 215                 220

Ala Ala Glu Leu Phe Pro Gly Pro Ala Lys Ala Asn Pro Asn Ile Phe
225                 230                 235                 240

Tyr Lys Ser Gly Asn Ile Ala Arg Thr Leu Ala Glu Val Tyr Ala Val
                245                 250                 255

Leu Asp Ala Lys Val Ala Lys His Arg Ala
            260                 265

<210> SEQ ID NO 28
<211> LENGTH: 14
<212> TYPE: PRT
<213> ORGANISM: ARTIFICIAL SEQUENCE
<220> FEATURE:
```

-continued

<223> OTHER INFORMATION: SYNTHETIC POLYPEPTIDE

<400> SEQUENCE: 28

Gly Pro Arg Arg Pro Arg Arg Pro Gly Arg Arg Ala Pro Val
1               5                   10

<210> SEQ ID NO 29
<211> LENGTH: 10
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 29

Lys Phe Phe Lys Phe Phe Lys Phe Phe Lys
1               5                   10

<210> SEQ ID NO 30
<211> LENGTH: 9
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 30

Lys Arg Lys Lys Arg Lys Lys Arg Lys
1               5

<210> SEQ ID NO 31
<211> LENGTH: 18
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 31

Ala Gly Ala Gly Ala Gly Ala Gly Ala Gly Ala Gly Ala Gly Ala Gly
1               5                   10                  15

Ala Ser

<210> SEQ ID NO 32
<211> LENGTH: 18
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 32

Arg Lys Lys Thr Arg Lys Arg Leu Lys Lys Ile Gly Lys Val Leu Lys
1               5                   10                  15

Trp Ile

<210> SEQ ID NO 33
<211> LENGTH: 432
<212> TYPE: DNA
<213> ORGANISM: pseudomonas putida

<400> SEQUENCE: 33
atgcggacat cgcaacgcgg cttgagcctc atcaagtcgt tcgagggcct gcgtctgcag      60
gcatatcaag attcagtagg cgtctggacg attggctacg ggaccactcg tggcgtgaag     120
gccggcatga aaatcagcaa ggaccaggca gagcgcatgc tgctgaacga cgtgcagcgc     180
ttcgagcctg aagttgagcg cctgatcaag gtgccgctga atcaggatca gtgggacgcc     240

```
ctgatgagct tcacctacaa cctggggcg gcaaacctcg aatcgtccac gctccgccga      300
ctgctcaatg ctggcaacta cgcagctgct gctgagcagt tcccgcgctg gaacaaggct    360
ggcgggcaag tacttgccgg cctaacccgt cggcgtgcag ctgagcggga gctgttcctg   420
ggggccgcgt ga                                                        432

<210> SEQ ID NO 34
<211> LENGTH: 609
<212> TYPE: DNA
<213> ORGANISM: Pseudomonas phage Lu11

<400> SEQUENCE: 34
atgtctgata acgcgttga aattaccgga acgtttccg gttttttcga gtccggtggc       60
cgtggtgtaa aaaccgtttc taccggcaaa ggtgacaacg gcggtgtgag ctacggcaag    120
catcagctgg cgtcgaataa cggctctatg ctctgttcc ttgaatctcc gttcggtgct    180
ccgtaccgtg cgcaattcgc aggactgaaa ccgggaaccg ctgcgtttac ttccgtgtac    240
aacaaaatcg caaatgaaac gccgaccgcg tttgaacggg accagttcca atacatcgcg   300
gcttcgcact acgatccaca agcggccaag ctgaaagccg aaggcattaa cgtcgatgac    360
cgacatgtcg cggtgcgtga atgcgtgttc agcgtagccg tgcaatatgg tcgaaatact    420
tcgatcatta tcaaagcact cggcagtaat ttccggggca gcgacaaaga cttcatcgaa   480
aaggtgcagg actatcgcgg tgccacggtt aacacctact ttaaatccag tagccagcaa   540
actcgcgaca cgtgaaaaa ccgctcgcag caagaaaagc aaatgctgct gaaactcctg    600
aatagttaa                                                           609

<210> SEQ ID NO 35
<211> LENGTH: 807
<212> TYPE: DNA
<213> ORGANISM: Pseudomonas aeruginosa

<400> SEQUENCE: 35 atgaccttc gatatggtga tcgttctcaa gaggtccgcc agcttcagcg tcgactgaac       60
acctgggccg cgccaacct ctacgaggac ggccacttcg cgccgccac tgaggacgcg      120 gtgcgcgcct tccagcgctc gcatggcctg gtcgccgatg gcatcgccgg cccgaagacc    180
ctggccgctc tcggcggagc tgactgctcg cacctgctgc agaacgccga cctcgtcgcc   240
gccgcaactc gcctcggcct gccgctggcg acgatctatg cggtcaatca ggtcgagtcg   300
aacggccagg ggttcctggg caacggcaag ccggcaatcc tgttcgaacg ccacatcatg   360
taccgccgtc tcgccgccca cgatcaggtc accgccgacc agttggccgc acagttcccc   420
gcgctggtga atcctcgccc gggcggctat gccggcggaa ccgccgagca ccagcgcctg    480
gcgaacgctc gccagatcga cgataccgcc gcactggagt cggccagttg gggagccttc    540
cagatcatgg gtttccactg gcaacgcctg ggctacatca gcgtgcaggc cttcgccgag   600
gccatggggc gcagcgagtc ggctcagttc gaagcgttcg tccgcttcat cgacaccgac   660
ccggcgctac acaaggcgct gaaggctcgc aaatgggccg acttcgcccg cctctacaat    720 ggcccccgact acaagcggaa cctctacgac aacaagctcg cgcgggccta cgagcaacac   780
gccaactgcg ccgaggccag cgcgtga                                        807

<210> SEQ ID NO 36
<211> LENGTH: 474
<212> TYPE: DNA
<213> ORGANISM: Artificial Sequence
```

<220> FEATURE:
<223> OTHER INFORMATION: SYNTHETIC NUCLEIC ACID

<400> SEQUENCE: 36

| | | |
|---|---|---|
| atgaaaaatt ttaatgaaat aattgaacat gttttaaaac atgagggtgg ttatgtaaat | 60 |
| gaccctaaag atttaggtgg tgaaaccaag tatggtatca ctaaaaggtt ttatccagat | 120 |
| cttgatatta agaatctaac aatagaacaa gcaacagaaa tctataaaaa agattattgg | 180 |
| gataaaaaca agtagaatc tcttcctcaa aatctatggc acatttattt tgatatgtgt | 240 |
| gttaatatgg gtaagagaac tgcagttaaa gttctacaaa gagcagctgt caataggggt | 300 |
| agagatatag aagttgatgg cggtttagga ccagcgacaa tcggagctct caaaggtgta | 360 |
| gaattagata gagttagagc tttcagagta agtattatg tggatttaat aacagctaga | 420 |
| ccagaacaag agaaatttta tttaggatgg tttagaagag caactgaagt ataa | 474 |

<210> SEQ ID NO 37
<211> LENGTH: 696
<212> TYPE: DNA
<213> ORGANISM: Pseudomonas phage phi2954

<400> SEQUENCE: 37

| | | |
|---|---|---|
| atgagcaaac aaggcggcgt gaaagttgca caggcagtag ccgcgctgtc ttcgcctggt | 60 |
| ctcaaaatcg acggtatcgt cggtaaagcg actcgggcgg ctgtgtcatc gatgcctagc | 120 |
| agccagaagg cggctacgga taagatactg caaagcgctg gaattggatc gcttgactcc | 180 |
| ctcttggctg agccggcagc agcgacgtcc gataccttcc gcgaagtggt gcttgccgtt | 240 |
| gcgcgtgagg caagaaaacg gggtctaaat cccgctttct atgtggctca catcgcgttg | 300 |
| gaaactgggt gggggcgttc cgtcccgaaa ctccctgacg ggcgttccag ttacaactac | 360 |
| gcagggctca aatatgcggc ggttaagacg caggttaagg gtaaaaccga aaccaatact | 420 |
| cttgaatata tcaagagcct accgaagacg gtgcgagact cttcgcagt gtttgcttcg | 480 |
| gcaggggatt tttcgagggt gtacttctgg tacctcctcg acagtccgtc tgcttatcgg | 540 |
| taccccggtc tcaagaatgc gaagacagct caggagtttg gtgacatcct ccaaaagggc | 600 |
| ggctacgcga ctgacccggc atacgccgca aaagtagcgt cgatcgcaag caccgccgtg | 660 |
| gctcgctacg gtagtgatgt gagttccgtt gcatag | 696 |

<210> SEQ ID NO 38
<211> LENGTH: 483
<212> TYPE: DNA
<213> ORGANISM: Pseudomonas aeruginosa

<400> SEQUENCE: 38

| | | |
|---|---|---|
| atggctgttg tttctgaaaa aaccgctggt ggtcgtaacg ttctggcttt cctggacatg | 60 |
| ctggcttggt ctgaaggtac ctctaccatc cgtggttctg acaacggtta caacgttgtt | 120 |
| gttggtggtg gtctgttcaa cggttacgct gaccacccgc gtctgaaagt ttacctgccg | 180 |
| cgttacaaag tttactctac cgctgctggt cgttaccagc tgctgtctcg ttactgggac | 240 |
| gcttaccgtg aatctctggc tctgaaaggt ggtttcaccc cgtctaacca ggacctggtt | 300 |
| gctctgcagc agatcaaaga acgtcgttct ctggctgaca tccaggctgg tcgtctggct | 360 |
| gacgctgttc agaaatgctc taacatctgg gcttctctgc cgggtgctgg ttacggtcag | 420 |
| cgtgaacact ctctggacga cctgaccgct cactacctgg ctgctggtgg tgttctgtct | 480 |
| taa | 483 |

<210> SEQ ID NO 39
<211> LENGTH: 558
<212> TYPE: DNA
<213> ORGANISM: Artificial Sequence
<220> FEATURE:
<223> OTHER INFORMATION: SYNTHETIC NUCLEIC ACID

<400> SEQUENCE: 39

```
atgatcctga ccaaagacgg tttctctatc atccgtaacg aactgttcga aggtaaactg      60
gaccagaccc aggttgacgc tatcaacttc atcgttgaaa aagctaccga atacggtctg     120
acctacccgg aagctgctta cctgctggct accatctacc acgaaaccgg tctgccgtct     180
ggttaccgta ccatgcagcc gatcaaagaa gctggttctg actcttacct gcgttctaaa     240
aaatactacc cgtacatcgg ttacggttac gttcagctga cctgggaaga aaactacgaa     300
cgtatcggta aactgatcgg tatcgacctg gttaaaaacc cggaaaaagc tctggaaccg     360
ctgatcgcta ccagatcgc tatcaaaggt atgctgaacg ttggttcac cggtgttggt      420
ttccgtcgta acgtccggt ttctaaatac aacaaacag agtacgttgc tgctcgtaac      480
atcatcaacg gtaaagacaa agctgaactg atcgctaaat acgctatcat cttcgaacgt    540
gctctgcgtt ctctgtaa                                                    558
```

<210> SEQ ID NO 40
<211> LENGTH: 798
<212> TYPE: DNA
<213> ORGANISM: Pseudomonas phage PhiPA3

<400> SEQUENCE: 40

```
atgacattac tgaagaaagg cgacaagggt gacgccgtaa acaactaca gcagaaactc       60
aaagaccttg ggtataccct gggtgtcgat ggcaacttcg gtaatggcac cgatactgtc     120
gttcgttctt tccaaaccaa aatgaagctt agtgttgatg gtgtggttgg taatggtact    180
atgagtacta ttgactctac tctagcaggc attaaagcgt ggaagactag tgtacctttc    240
cctgcgacga acaaatcccg agcaatggca atgccaacgt tgactgaaat aggtcgactg    300
acaaacgttg atcctaaatt gctagcgaca ttctgttcta tcgaaagcgc gtttgattac    360
acagctaaac cctacaagcc cgatggcaca gtgtacagct ccgccgaagg ttggttccag    420
ttcctggatg caacatggga tgacgaagtg cgtaaacacg gtaagcaata tagcttccct    480
gttgatcctg gtcgttcttt gcgtaaagat ccacgggcta atggcttgat gggcgctgag    540
ttcctcaaag ggaatgctgc tattctgcgg ccagtactgg gtcatgaacc gagcgacaca    600
gatcttatc tagcccatt catgggagca ggtggcgcaa acagttcct tatggccgat     660
caaaataaat tggctgccga attgttccct ggtccagcta aggctaatcc taacatcttc    720
tataaatccg gaaatattgc ccgcactta gcagaggtct atgcagtcct cgatgctaag    780
gtagccaagc atagagct                                                   798
```

<210> SEQ ID NO 41
<211> LENGTH: 399
<212> TYPE: DNA
<213> ORGANISM: Acinetobacter sp. 1294596

<400> SEQUENCE: 41

```
atgtctttca aactgggtaa acgttctctg tctaacctgg aaggtgttca cccggacctg      60
atcaaagttg ttaaacgtgc tatcgaactg accgaatgcg acttcaccgt taccgaaggt    120
ctgcgttcta agaacgtca ggctcagctg ctgaaagaaa aaaaaaccac cacctctaac     180
```

```
tctcgtcacc tgaccggtca cgctgttgac ctggctgctt gggttaacaa caccgtttct    240
tgggactgga aatactacta ccagatcgct gacgctatga aaaaagctgc ttctgaactg    300
aacgtttcta tcgactgggg tggtgactgg aaaaaattca agacggtcc gcacttcgaa     360 ctgacctggt ctaaataccc gatcaaaggt gcttcttaa                           399

<210> SEQ ID NO 42
<211> LENGTH: 351
<212> TYPE: DNA
<213> ORGANISM: Pseudomonas phage PaP2

<400> SEQUENCE: 42
atgaaactca gcgaaaaacg agcactgttc acccagctgc ttgcccagtt aattctttgg    60
gcaggaactc aggatcgagt gtcagtagcc ttggatcaag tgaaaaggac acaggctgaa   120
gctgatgcca atgctaagtc tggagcaggc attaggaact ctctccatct actgggatta   180
gccggtgatc ttatcctcta caaggatggt aaatacatgg ataagagcga ggattataag   240
ttcctgggag attactggaa gagtctccat cctctttgtc ggtggggcgg agattttaaa   300
agccgtcctg atggtaatca tttctccttg gaacacgaag gagtgcaata a            351

<210> SEQ ID NO 43
<211> LENGTH: 432
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 43
atgcggacat cgcaacgcgg cttgagcctc atcaagtcgt tcgagggcct gcgtctgcag    60
gcatatcaag attcagtagg cgtctggacg attggctacg ggaccactcg tggcgtgaag   120
gccggcatga aaatcagcaa ggaccaggca gagcgcatgc tgctgaacga cgtgcagcgc   180
ttcgagcctg aagttgagcg cctgatcaag gtgccgctga atcaggatca gtgggacgcc   240
ctgatgagct tcacctacaa cctgggggcg caaacctcg aatcgtccac gctccgcgac    300
ctgctcaatg ctggcaacta cgcagctgct gctgagcagt tcccgcattg gaacaaggct   360
ggcgggcaag tacttgccgg cctaacccgt cggcgtgcag ctgagcggga gctgttcctg   420
ggggccgcgt ga                                                        432

<210> SEQ ID NO 44
<211> LENGTH: 435
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 44
atgcgtacat cccaacgagg catcgacctc atcaaatcct tcgagggcct gcgcctgtcc    60
gcttaccagg actcggtggg tgtctggacc ataggttacg gcaccactcg ggcgtcacc    120 cgctacatga cgatcaccgt cgagcaggc gagcggatgc tgtcgaacga cattcagcgc    180
ttcgagccag agctagacag gctggcgaag gtgccactga accagaacca gtgggatgcc   240
ctgatgagct tcgtgtacaa cctgggcgcg gccaatctgg cgtcgtccac gctgctcgac   300
ctgctgaaca gggtgactta ccaggagca gcggaccagt tcccgcattg ggtgaatgcg   360
ggcggtaagc gcttggatgg tctggttaag cgtcgagcag ccgagcgtgc gctgttcctg   420
```

```
gagccactat cgtga                                                    435
```

<210> SEQ ID NO 45
<211> LENGTH: 474
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 45

```
atgcgtacat cccaacgagg catcgacctc atcaaatcct tcgagggcct gcgcctgtcc    60
gcttaccagg actcggtggg tgtctggacc ataggttacg gcaccactcg ggcgtcacc    120
cgctacatga cgatcaccgt cgagcaggcc gagcggatgc tgtcgaacga cattcagcgc   180
ttcgagccag agctagacag gctggcgaag gtgccactga accagaacca gtgggatgcc   240
ctgatgagct tcgtgtacaa cctgggcgcg gccaatctgg cgtcgtccac gctgctcaag   300
ctgctgaaca agggtgacta ccagggagca gcggaccagt tcccgcgctg ggtgaatgcg   360
ggcggtaagc gcttggatgg tctggttaag cgtcgagcag ccgagcgtgc gctgttcctg   420
gagccactat cgggcccccg ccggccacga cgacctggac gccgggcacc tgtc         474
```

<210> SEQ ID NO 46
<211> LENGTH: 519
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 46

```
aaattcttta agttctttaa gttttttaaa gccggcgcag gagctggtgc aggagctggt    60
gcaggagctg gtgcaggagc tagcatgcgt acatcccaac gaggcatcga cctcatcaaa   120
tccttcgagg gcctgcgcct gtccgcttac caggactcgg tgggtgtctg gaccataggt   180
tacggcacca ctcggggcgt cacccgctac atgacgatca ccgtcgagca ggccgagcgg   240
atgctgtcga acgacattca gcgcttcgag ccagagctag acaggctggc gaaggtgcca   300
ctgaaccaga accagtggga tgccctgatg agcttcgtgt acaacctggg cgcggccaat   360
ctggcgtcgt ccacgctgct caagctgctg aacaagggtg actaccaggg agcagcggac   420
cagttcccgc gctgggtgaa tgcgggcggt aagcgcttgg atggtctggt taagcgtcga   480
gcagccgagc gtgcgctgtt cctggagcca ctatcgtaa                          519
```

<210> SEQ ID NO 47
<211> LENGTH: 516
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 47

```
aaacgcaaga acgtaagaa acgcaaagcc ggcgcaggag ctggtgcagg agctggtgca    60
ggagctggtg caggagctag catgcgtaca tcccaacgag gcatcgacct catcaaatcc   120
ttcgagggcc tgcgcctgtc cgcttaccag gactcggtgg gtgtctggac cataggttac   180
ggcaccactc ggggcgtcac ccgctacatg acgatcaccg tcgagcaggc cgagcggatg   240
ctgtcgaacg acattcagcg cttcgagcca gagctagaca ggctggcgaa ggtgccactg   300
aaccagaacc agtgggatgc cctgatgagc ttcgtgtaca acctgggcgc ggccaatctg   360
gcgtcgtcca cgctgctcaa gctgctgaac aagggtgact accagggagc agcggaccag   420
```

```
ttcccgcgct gggtgaatgc gggcggtaag cgcttggatg gtctggttaa gcgtcgagca    480
gccgagcgtg cgctgttcct ggagccacta tcgtaa                              516

<210> SEQ ID NO 48
<211> LENGTH: 432
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 48
atgacctaca ccctgtctaa acgttctctg gacaacctga aggtgttca cccggacctg      60 gttgctgttg ttcaccgtgc tatccagctg accccggttg acttcgctgt tatcgaaggt    120
ctgcgttctt tttctcgtca gaagaactg gttgctgctg gtgcttctaa aaccatgaac    180
tctcgtcacc tgaccggtca cgctgttgac ctggctgctt acgttaacgg tatccgttgg    240
gactggccgc tgtacgacgc tatcgctgtt gctgttaaag ctgctgctaa agaactgggt    300
gttgctatcg tttggggtgg tgactggacc accttcaaag acggtccgca cttcgaactg    360
gaccgttcta ataccgtaa aaaaacccgt aaacgtctga aaaaaatcgg taaagttctg    420
aaatggatct aa                                                        432

<210> SEQ ID NO 49
<211> LENGTH: 465
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 49
aaattcttta agttctttaa gttttttaaa gccggcgcag gagctggtgc aggagctggt      60
gcaggagctg gtgcaggagc tagcatgaca tacaccctga gcaaaagaag cctggataac    120
ctaaaaggcg ttcatcccga tctggttgcc gttgtccatc gcgccatcca gcttacaccg    180
gttgatttcg cggtgatcga aggcctgcgc tccgtatccc gccaaaagga actggtggcc    240
gccggcgcca gcaagaccat gaacagccga cacctgacag gccatgcggt tgatctagcc    300
gcttacgtca atggcatccg ctgggactgg cccctgtatg acgccatcgc cgtggctgtg    360
aaagccgcag caaggaatt gggtgtggcc atcgtgtggg gcggtgactg gaccacgttt    420
aaggatggcc cgcactttga actggatcgg agcaaataca gataa                    465

<210> SEQ ID NO 50
<211> LENGTH: 453
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 50
atgtctttca aactgggtaa acgttctctg tctaacctgg aaggtgttca cccggacctg      60
atcaaagttg ttaaacgtgc tatcgaactg accgaatgcg acttcaccgt taccgaaggt    120
ctgcgttcta agaacgtca ggctcagctg ctgaaagaaa aaaaaccac acctctaac    180 tctcgtcacc tgaccggtca cgctgttgac ctggctgctt gggttaacaa caccgtttct    240
tgggactgga atactacta ccagatcgct gacgctatga aaaagctgc ttctgaactg    300 aacgtttcta tcgactgggg tggtgactgg aaaaaattca agacggtcc gcacttcgaa    360
```

```
ctgacctggt ctaaatacccc gatcaaaggt gcttctcgta aaaaaacccg taaacgtctg    420
aaaaaaatcg gtaaagttct gaaatggatc taa                                  453
```

<210> SEQ ID NO 51
<211> LENGTH: 474
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 51

```
ggtccgcgtc gtccgcgtcg tccgggtcgt cgtgctccgg ttatgcggac atcgcaacgc    60
ggcttgagcc tcatcaagtc gttcgagggc ctgcgtctgc aggcatatca agattcagta   120
ggcgtctgga cgattggcta cgggaccact cgtggcgtga aggccggcat gaaaatcagc   180
aaggaccagg cagagcgcat gctgctgaac gacgtgcagc gcttcgagcc tgaagttgag   240
cgcctgatca aggtgccgct gaatcaggat cagtgggacg ccctgatgag cttcacctac   300
aacctggggg cggcaaacct cgaatcgtcc acgctccgcg acctgctcaa tgctggcaac   360
tacgcagctg ctgctgagca gttcccgcat tggaacaagg ctggcgggca agtacttgcc   420
ggcctaaccc gtcggcgtgc agctgagcgg gagctgttcc tggggggccgc gtga        474
```

<210> SEQ ID NO 52
<211> LENGTH: 480
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 52

```
ggtccgcgtc gtccgcgtcg tccgggtcgt cgtgctccgg ttatgcgtac atcccaacga    60
ggcatcgacc tcatcaaaatc cttcgagggc ctgcgcctgt catgcgctta ccaggactcg   120
gtgggtgtct ggaccatagg ttacggcacc actcggggcg tcacccgcta catgacgatc   180
accgtcgagc aggccgagcg gatgctgtcg aacgacattc agcgcttcga gccagagcta   240
gacaggctgg cgaaggtgcc actgaaccag aaccagtggg atgccctgat gagcttcgtg   300
tacaacctgg gcgcggccaa tctggcgtcg tccacgctgc tcgacctgct gaacaagggt   360
gactaccagg gagcagcgga ccagttcccg cattgggtga atgcgggcgg taagcgcttg   420
gatggtctgg ttaagcgtcg agcagccgag cgtgcgctgt tcctggagcc actatcgtga   480
```

<210> SEQ ID NO 53
<211> LENGTH: 405
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 53

```
atgaaactca gcgaaaaacg agcactgttc acccagctgc ttgcccagtt aattctttgg    60
gcaggaactc aggatcgagt gtcagtagcc ttggatcaag tgaaaaggac acaggctgaa   120
gctgatgcca atgctaagtc tggagcaggc attaggaact ctctccatct actgggatta   180
gccggtgatc ttatcctcta caaggatggt aaatacatgg ataagagcga ggattataag   240
ttcctgggag attactggaa gagtctccat cctctttgtc ggtggggcgg agattttaaa   300
agccgtcctg atggtaatca tttctccttg gaacacgaag gagtgcaacg taaaaaaacc   360
cgtaaacgtc tgaaaaaaat cggtaaagtt ctgaaatgga tctaa                  405
```

<210> SEQ ID NO 54
<211> LENGTH: 432
<212> TYPE: DNA
<213> ORGANISM: ARTIFICIAL SEQUENCE
<220> FEATURE:
<223> OTHER INFORMATION: SYNTHETIC NUCLEIC ACID

<400> SEQUENCE: 54

```
atgcggacat cgcaacgcgg cttgagcctc atcaagtcgt tcgagggcct gcgtctgcag      60
gcatatcaag attcagtagg cgtctggacg attggctacg ggaccactcg tggcgtgaag     120
gccggcatga aaatcagcaa ggaccaggca gagcgcatgc tgctgaacga cgtgcagcgc     180
ttcgagcctg aagttgagcg cctgatcaag gtgccgctga atcaggatca gtgggacgcc     240
ctgatgagct tcacctacaa cctgggggcg gcaaacctcg aatcgtccac gctccgcgac     300
ctgctcaatg ctggcaacta cgcagctgct gctgagcagt tcccgcactg gaacaaggct     360
ggcgggcaag tacttgccgg cctaacccgt cggcgtgcag ctgagcggga gctgttcctg     420
ggggccgcgt ga                                                         432
```

IDENTIFICATION OF LYSINS AND DERIVATIVES THEREOF WITH BACTERICIDAL ACTIVITY AGAINST PSEUDOMONAS AERUGINOSA

CROSS-REFERENCE TO RELATED APPLICATIONS

This application is a U.S. National Stage Application of International Application No. PCT/US2018/065265, filed on 12 Dec. 2018, which claims priority to U.S. Provisional Patent Application No. 62/597,577, filed on 12 Dec. 2017, and U.S. Provisional Patent Application No. 62/721,969, filed on 23 Aug. 2018, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 27 May 2020 is named 0341.0015_ST25.txt and is 62,180 bytes in size.

BACKGROUND OF THE INVENTION

Gram-negative bacteria, in particular members of the genus *Pseudomonas*, are an important cause of serious and potentially life-threatening invasive infections. *Pseudomonas* infection presents a major problem in burn wounds, chronic wounds, chronic obstructive pulmonary disorder (COPD) and other structural lung diseases, cystic fibrosis, surface growth on implanted biomaterials, and within hospital surface and water supplies where it poses a host of threats to vulnerable patients, such as immunosuppressed patients and patients in intensive care (ICU).

Once established in the patient, *P. aeruginosa* can be especially difficult to treat. The genome encodes a host of resistance genes, including multidrug efflux pumps and enzymes conferring resistance to beta-lactam and aminoglycoside antibiotics, making therapy against this Gram-negative pathogen particularly challenging due to the lack of novel antimicrobial therapeutics. This challenge is compounded by the ability of *P. aeruginosa* to grow in a biofilm, which may enhance its ability to cause infections by protecting bacteria from host defenses and conventional antimicrobial chemotherapy.

In the healthcare setting, the incidence of drug resistant strains of *Pseudomonas aeruginosa* is increasing. A multi-state point-prevalence survey estimated that *P. aeruginosa* caused 7% of all healthcare-acquired infections (HAIs) (1). More than 6,000 (13%) of the 51,000 HAIs caused by *P. aeruginosa* annually are multi-drug resistant (MDR), with roughly 400 deaths per year (2). Extensively drug resistant (XDR) and pan-drug-resistant (PDR) strains represent emerging threats for which there are limited or no available treatments (3). Invasive *P. aeruginosa* infections including bloodstream infections (BSIs), which are among the most lethal HAIs—for example, *P. aeruginosa* accounts for 3 to 7% of all BSIs, with mortality rates between 27 and 48% (4). The incidence of invasive bloodstream infections including those caused by *P. aeruginosa* may be underestimated since the majority of healthcare in the USA is performed in smaller, non-teaching community hospitals. In an observational study of BSIs in community hospitals *P. aeruginosa* was one of the top 4 MDR pathogens (5) and overall hospital mortality was 18%. Additionally, outbreaks of MDR *P. aeruginosa* are well described (6). Poor outcomes are associated with MDR stains of *P. aeruginosa* that frequently require treatment with drugs of last resort such as colistin (7). There is clearly an unmet medical need for different antimicrobials with novel mechanisms to target MDR *P. aeruginosa* for the treatment of invasive infections including but not limited to BSIs.

An innovative approach to treating bacterial infections focuses on a family of bacteriophage-encoded cell wall peptidoglycan (PG) hydrolases called lysins (8). Lysin technology is currently based on the use of purified recombinant lysin proteins that act externally on a range of Gram-positive (GP) pathogens, resulting in lysis of the bacterial cell on contact with multi-log-fold killing. Lysins act as "molecular scissors" to degrade the peptidoglycan (PG) meshwork responsible for maintaining cell shape and for withstanding the internal osmotic pressure. Degradation of PG results in osmotic lysis. In addition to rapid kill and a novel mode of action compared to antibiotics, other hallmarks of lysin activity include anti-biofilm activity, absence of pre-existing resistance, potent synergy with antibiotics (in sub-minimum inhibitory concentrations (MIC)), and the suppression of resistance to antibiotics when antibiotics are used in addition to lysins. Importantly, multiple researcher groups have demonstrated the ability of topical, intra-nasal, and parenteral dosing with lysins to control antibiotic resistant GP bacterial pathogens in multiple animal models (9-11).

Lysin technology was originally developed to treat GP pathogens. The development of lysins to target Gram-negative (GN) bacteria has heretofore been limited. The outer membrane (OM) of Gram-negative bacteria plays a critical role as a barrier to extracellular macromolecules and limits access to subjacent peptidoglycan (12-14).

The OM is the distinguishing feature of GN bacteria and comprises a lipid bilayer with an internal leaflet of phospholipids and an external amphiphilic leaflet largely consisting of lipopolysaccharide (LPS) (15). The LPS has three main sections: a hexa-acylated glucosamine-based phospholipid called lipid A, a polysaccharide core and an extended, external polysaccharide chain called 0-antigen. The OM presents a non-fluid continuum stabilized by three major interactions, including: i) the avid binding of LPS molecules to each other, especially if cations are present to neutralize phosphate groups; ii) the tight packing of largely saturated acyl chains; and iii) hydrophobic stacking of the lipid A moiety. The resulting structure is a barrier for both hydrophobic and hydrophilic molecules. Below the OM, the PG forms a thin layer that is very sensitive to hydrolytic cleavage—unlike the PG of GP bacteria which is 30-100 nm thick and consists of up to 40 layers, the PG of GN bacteria is only 2-3 nm thick and consists of only 1-3 layers. Potent antimicrobial activity could be achieved if lysins targeting GN bacteria are engineered to penetrate the OM either alone or in combination with OM-destabilizing agents and/or antibiotics.

Accordingly, the discovery and development of GN lysins that penetrate the OM is an important goal and would fulfill an important yet unmet need to devise effective therapies for treating or preventing Gram-negative bacterial infections. Multiple agents with OM-permeabilizing and OM-disrupting activities have been previously described. For example, poly-cationic compounds, including polymyxin antibiotics and aminoglycosides, compete with stabilizing divalent cations in the OM for interactions with phospholipids in LPS, leading to disorganization of the OM (16). Similarly, EDTA and weak acids chelate the divalent cations leading to OM disorganization (17). A large group of naturally occurring antimicrobial peptides and synthetic peptidomimetics thereof (herein referred to as AMPs) are also known to penetrate the OM based on a self-promoted uptake pathway (18-20). Translocation of both poly-cationic and amphipathic AMPs is driven by a primary electrostatic interaction with the LPS, followed by cation displacement, membrane disorganization and transient openings, and in some cases internalization of the AMP. The membrane-interacting antimicrobial activity of many AMPs, can be "activated" in blood by strategically engineering the amphipathic domains either by altering hydrophobicity, total charge, and the positioning of polar residues in the hydrophobic face or by incorporating D, L residues in place of all-L counterparts (18, 19, 21, 22).

The inventors have advanced lysin technology to address GN pathogens using a variety of techniques to enable OM penetration, as outlined herein. Indeed, the inventors have previously filed an International patent Application, PCT/US2016/052338 filed Sep. 16, 2016 and published as WO/2017/049233. This prior PCT application is fully incorporated by reference herein for all purposes. For example. Lysins GN2, GN4, GN14, GN43, and GN37 were first disclosed in the foregoing PCT Application.

Recent studies identified lysins with intrinsic antimicrobial activity against GN bacteria (12, 13, 17). The antimicrobial effect in several cases is attributed to N- or C-terminal amphipathic or poly-cationic α-helical domains that drive penetration of the LPS and translocation across the OM, resulting in PG degradation and osmotic lysis. Interestingly, access of such lysins to the PG can be facilitated by OM-destabilizing compounds including EDTA and mild organic acids. Although combinations with EDTA and mild organic acids are not practical as drugs, the findings illustrate the concept of facilitating GN lysin activity.

A more recent approach uses GN lysins fused to specific α-helical domains with polycationic, amphipathic, and hydrophobic features to promote translocation across the OM. These findings have resulted in GN lysins called "artilysins", which are highly active in vitro and are envisioned for topical applications (17). However, low activity has been reported for artilysins in vivo. Consistently, artilysin GN126 listed as a control in the present disclosure (see Table 4) also exhibited low activity.

Despite the in vitro potency of artilysins and lysins, including GN lysins, with intrinsic antimicrobial activity, a major limitation remains with respect to a distinct lack of activity in human blood matrices, making systemic therapy a challenge (13, 14). It is believed that physiologic salt and divalent cations compete for LPS binding sites and interfere with the α-helical translocation domains of lysins, including GN lysins, thereby restricting activity in blood and more specifically in the presence of serum, therefore limiting the possibility to use lysins for treating invasive infections (23). A similar lack of activity in blood has been reported for multiple different OM-penetrating and destabilizing AMPs (18-20, 22).

SUMMARY OF THE INVENTION

A major design challenge facing GN lysin development for the treatment of invasive infections via systemic administration is the need to alleviate the inactivation in blood (or for example in human serum).

Native GN lysins with intrinsic activity (i.e., high-level activity in HEPES buffer and low-level activity in human serum) were first identified and then modified by replacement of charged amino acids with non-charged ones and/or fusion with an alpha-helical antimicrobial peptide for improved activity and improved activity in serum.

Based on this work, putative native lysins were identified and were evaluated for activity. The lysins are listed in Table 3 and described by their sequences. The unmodified lysins exhibit varying levels of activity in the presence of human serum.

Modifications of the lysin proteins were based on the following: i) incorporation of amino acid substitutions into the lysin protein to change the overall pI of the molecule to facilitate OM penetration or reduce sensitivity to human serum or both; and/or ii) the fusion of an antimicrobial peptide sequence (preferably, one known to be active in serum) to the N- or C-terminus of the lysin to form a fusion polypeptide to facilitate outer membrane penetration and translocation.

Modified GN-lysins were obtained by modifying lysin proteins as described herein. The modified GN-lysins are demonstrated to exhibit improved activity in human serum compared to that of the parent (unmodified) lysins. Charged amino acid residues of native lysin proteins were mutagenized randomly by noncharged amino acid residues and the resulting polypeptides were tested for activity, including activity in the presence of human serum. The active modified polypeptides typically differed from the parent polypeptides in 1 to 3 amino acid residues. Alternatively, or additionally, antimicrobial peptide (AMP) sequences were fused onto the native or modified GN lysin sequences with or without a linker. The antimicrobial peptides are characterized by an alpha-helical domain to mediate outer membrane disruption and translocation of the lysin. The linkers are short peptide sequences 5 to 20 amino acids in length which are flexible (for example are rich in serine and/or glycine residues) and are designed not to perturb the structure of either the AMP or the lysin portion of the fusion polypeptide and to allow each to move freely.

Each of the putative lysins and modified GN-lysins described herein, have been or can be purified to >90% homogeneity and examined in a series of assays to assess in vitro activity.

The present disclosure encompasses lysin polypeptides and modified lysin polypeptides which are synthetically and/or recombinantly produced. The present invention encompasses novel lysin polypeptides and modified lysin polypeptides, as well as the use of said polypeptides for the treatment of infections with Gram-negative bacteria and, especially in the presence of blood matrices, e.g., human serum.

What is more, the present invention encompasses the use of lysin polypeptides and modified lysin polypeptides for disrupting biofilms comprising Gram-negative microorganisms, for example in prosthetic or in other medical devices, in vivo, ex vivo or in vitro. The Gram-negative microorganisms of biofilms include *Pseudomonas* species, for example, *Pseudomonas aeruginosa*.

In one aspect, the present disclosure is directed to a pharmaceutical composition or drug formulation comprising an effective amount of an isolated lysin polypeptide having an amino acid sequence selected from the group consisting of SEQ ID NO: 2, 4, 5-9 and SEQ ID NO: 13-27 or a peptide having at least 80% sequence identity therewith, said peptide having lytic activity, wherein the lysin polypeptide inhibits the growth, or reduces the population, or kills at least one species of Gram-negative bacteria; and a pharmaceutically acceptable carrier.

In an embodiment the pharmaceutical composition comprises an effective amount of at least one lysin polypeptide selected from the group consisting of peptides GN3, CN147, GN146, GN156, GN54, GN92, GN121, GN94, GN9, GN10, GN13, GN17, GN105, GN108, GN123, GN150, GN200, GN201, GN203, GN204 and GN205 or a fragment thereof maintaining lytic activity, wherein the lysin polypeptide or fragment inhibits the growth, or reduces the population, or at least one species of Gram-negative bacteria; and a pharmaceutically acceptable carrier.

The present pharmaceutical compositions/drug formulations, in one embodiment, comprise an effective amount of at least one lysin polypeptide and at least one antibiotic suitable for the treatment of Gram-negative bacteria. In some embodiments, the composition is a combination of two components to be administered combinedly or separately, one containing a lysin in accordance with the present disclosure and one containing an antibiotic. In some embodiments, the antibiotic is provided in a suboptimal dose. In some embodiments the antibiotic may be one to which the Gram-negative bacteria have developed resistance, the use of the lysin serving to overcome this resistance).

In some embodiments, the present compositions (with or without antibiotic) or combinations (with lysin and antibiotic) are adapted for oral, topical, parenteral or inhalable administration. In some embodiments, one component of the combination may be adapted to be administered by a different route than the other component. For example, in the experiments detailed below, antibiotics are administered subcutaneously (SC) whereas the lysins are administered intravenously (IV).

In an embodiment, the antibiotic may be selected from the list of GN suitable antibiotics provided below and combinations thereof. In a more specific embodiment, the antibiotic may be selected from amikacin, azithromycin, aztreonam, ciprofloxacin, colistin, rifampicin, carbapenems and tobramycin and combinations of two or more of the foregoing.

Certain embodiments of the present disclosure contemplate a sterile container that contains one of the above-mentioned pharmaceutical compositions comprising a lysin polypeptide and optionally one or more additional components. By way of example, but not limitation, the sterile container is one component of a kit; the kit may also contain, for example, a second sterile container that contains at least one additional therapeutic agent. Thus, one of the combinations of GN antibiotic and GN lysin disclosed herein may optionally be provided in such a kit.

In an aspect, the invention encompasses a vector comprising a nucleic acid molecule which encodes a lysin peptide having an amino acid sequence selected from the group consisting of SEQ ID NO: 2, 4, 5-9 and SEQ ID NO: 13-27, or a peptide having at least 80% sequence identity therewith, said peptide having lytic activity, wherein the encoded lysin polypeptide inhibits the growth, or reduces the population, or kills at least one species of Gram-negative bacteria in the absence or presence of human serum.

In another embodiment, the vector is a recombinant expression vector comprising a nucleic acid encoding one of the foregoing lysin polypeptides including the at least 80% sequence identity variants thereof, wherein the encoded lysin peptide has the property of inhibiting the growth, or reducing the population, or at least one species of Gram-negative bacteria in the absence and/or presence of human serum, the nucleic acid being operatively linked to a heterologous promoter.

A host cell comprising the foregoing vectors are also contemplated. In some embodiments the nucleic acid sequence is a cDNA sequence.

In yet another aspect, the disclosure is directed to isolated, purified nucleic acid encoding a lysin polypeptide comprising a sequence selected from the group consisting of SEQ ID NO: 2, 4, 5-9 and SEQ ID NO: 13-27. In an alternative embodiment, the isolated, purified nucleic acid comprises a nucleotide sequence selected from the group consisting of SEQ ID NO: 33 through SEQ ID NO:54, degenerate code thereof, and transcripts thereof. In accordance with the embodiments presented herein, a defined nucleic acid includes not only the identical nucleic acid but also any minor base variations including, in particular, substitutions resulting in a synonymous codon (a different codon specifying the same amino acid residue). The claims drawn to nucleic acid will thus be deemed to encompass the complementary sequence to any recited single-stranded sequence. Optionally, the nucleic acid is cDNA.

In other aspects, the present disclosure is directed to various methods/uses. One such is a method/use for inhibiting the growth, or reducing the population, or killing of at least one species of Gram-negative bacteria, the method comprising contacting the bacteria with a composition comprising an effective amount of a GN lysin polypeptide comprising a sequence selected from the group consisting of SEQ ID NO: 2, 4, 5-9 and SEQ ID NO: 13-27, or a peptide having at least 80% sequence identity therewith, said peptide having lytic activity for a period of time sufficient to inhibit said growth or reduce said population or kill said at least one species of Gram-negative bacteria in the absence and/or presence of human serum.

Another such method/use is for inhibiting the growth, or reducing the population, or killing of at least one species of Gram-negative bacteria, the method comprising contacting the bacteria with a composition comprising an effective amount of at least one GN lysin polypeptide selected from the group consisting of the GN lysins as described in SEQ ID NO: 2, 4, 5-9 and SEQ ID NO: 13-27, or active fragments thereof, wherein the polypeptide or active fragment has the property of inhibiting the growth, or reducing the population, or killing *P. aeruginosa* and optionally at least one other species of Gram-negative bacteria in the absence and/or presence of human serum.

Another method/medical use is for treating a bacterial infection caused by a Gram-negative bacterium, such as *P. aeruginosa* or *A. baumannii*, comprising administering to a subject diagnosed with, at risk for, or exhibiting symptoms of a bacterial infection, one or more of the foregoing compositions.

In any of the foregoing methods/medical uses the Gram-negative bacterium is at least one selected from the group consisting of *Acinetobacter baumannii, Pseudomonas aeruginosa, E. coli, Klebsiella pneumoniae, Enterobacter cloacae, Salmonella* spp., *N. gonorrhoeae*, and *Shigella* spp. Alternatively, the Gram-negative bacteria is *Pseudomonas aeruginosa*.

Another method/medical use is for treating or preventing a topical or systemic pathogenic bacterial infection caused by a Gram-negative bacteria comprising administering to a subject in need of treatment one of the foregoing compositions. Topical infections include infections that can be treated by local or topical application of an antibacterial agent. Examples of topical infections include those confined to a particular location, such as an organ or tissue or an implanted prosthesis or other medical device. Examples are infections of the skin, gums, infected wounds, infections of the ear etc., infections in the area where a catheter is installed etc.

Another such method/medical use is for preventing or treating a bacterial infection comprising co-administering to a subject diagnosed with, at risk for, or exhibiting symptoms of a bacterial infection, a combination of a first effective amount of one of the foregoing compositions and a second effective amount of an antibiotic suitable for the treatment of Gram-negative bacterial infection.

DETAILED DESCRIPTION OF THE INVENTION

Definitions

As used herein, the following terms and cognates thereof shall have the meanings ascribed to them below unless the context clearly indicates otherwise.

"Carrier," applied to pharmaceutical compositions, refers to a diluent, excipient, additive or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Other examples include dispersion media, solubilizing agents, coatings, preservatives, isotonic and absorption delaying agents, surfactants, propellants and the like. Suitable pharmaceutical carriers are described in "Remington's Pharmaceutical Sciences" by E. W. Martin, 18th Edition.

"Pharmaceutically acceptable carrier" includes any of the foregoing carriers that are physiologically compatible. The carrier(s) must be "acceptable" in the sense of not being deleterious to the subject to be treated in amounts typically used in medicaments. Pharmaceutically acceptable carriers are compatible with the other ingredients of the composition without rendering the composition unsuitable for its intended purpose. Furthermore, pharmaceutically acceptable carriers are suitable for use with subjects as provided herein without undue adverse side effects (such as toxicity, irritation, and allergic response). Side effects are "undue" when their risk outweighs the benefit provided by the composition.

"Bactericidal," in the context of an agent, conventionally means having the property of causing the death of bacteria or capable of killing bacteria to an extent of at least a 3-log10 (99.9%) or better reduction among an initial population of bacteria over an 18-24-hour period.

"Bacteriostatic" conventionally means having the property of inhibiting bacterial growth, including inhibiting growing bacterial cells, thus causing a 2-log10 (99%) or better and up to just under a 3-log reduction among an initial population of bacteria over an 18-24-hour period.

"Antibacterial" in a context of an agent is used generically to include both bacteriostatic and bactericidal agents.

"Antibiotic" refers to an antibiotic compound that can be either one affecting cell wall peptidoglycan biosynthesis, one affecting cell membrane integrity or one affecting DNA or protein synthesis in bacteria. Nonlimiting examples of antibiotics active against Gram-negative bacteria include cephalosporins, such as ceftriaxone-cefotaxime, ceftazidime, cefepime, cefoperazone, ceftobiprole, fluoroquinolones such as ciprofloxacin, levofloxacin, aminoglycosides such as gentamicin, tobramycin, amikacin, piperacillin, ticarcillin, carbapenems, such as imipenem, meropenem, doripenem other beta lactam antibiotics active against GN bacteria, such as broad spectrum penicillins with or without beta-lactamase inhibitors, ansamycins such as rifampicin, and bactericidal polypeptides such as polymyxin B and colistin.

"Drug resistant" in a context of a pathogen and more specifically a bacterium, generally refers to a bacterium that is resistant to the antibacterial activity of a drug. When used in a more particular way, drug resistance specifically refers to antibiotic resistance. In some cases, a bacterium that is generally susceptible to a particular antibiotic can develop resistance to the antibiotic, thereby becoming a drug resistant microbe or strain. A "multi-drug resistant" ("MDR") pathogen is one that has developed resistance to at least two classes of antimicrobial drugs, each used as monotherapy. For example, certain strains of *P. aeruginosa* have been found to be resistant to several antibiotics including among others ceftolozane-tazobactam, ceftazidime, cefepime, piperacillin-tazobactam, aztreonam, imipenem, meropenem, ciprofloxacin, ticarcillin, tobramycin, amikacin, and colistin. One skilled in the art can readily determine if a bacterium is drug resistant using routine laboratory techniques that determine the susceptibility or resistance of a bacterium to a drug or antibiotic. See, for example, Cabot, G. et al, 2016, Antimicrob. Agents and Chemother. 60(3):1767, DOI: 10.1128/AAC.02676-15; and (Antibiotic Resistant Threats in the United States, 2013, U.S. Department of Health and Services, Centers for Disease Control and Prevention).

"Effective amount" refers to an amount which, when applied or administered in an appropriate frequency or dosing regimen, is sufficient to prevent, reduce, inhibit or eliminate bacterial growth or bacterial burden or prevent, reduce or ameliorate the onset, severity, duration or progression of the disorder being treated (here Gram-negative bacterial pathogen growth or infection), prevent the advancement of the disorder being treated, cause the regression of the disorder being treated, or enhance or improve the prophylactic or therapeutic effect(s) of another therapy, such as antibiotic or bacteriostatic therapy. A useful effective amount range for the present polypeptides will be from about 0.01 mg/kg to about 50 mg/kg, with a typical range being from about 0.01 to 25 mg/kg, and a common range being from about 0.01 to about 10 mg/kg. Upward adjustments to the lower limit are contemplated depending on the potency of a particular lysin; downward adjustments to the upper limit are also contemplated depending primarily on toxicity of a particular lysin. Such adjustments are within the skill in the art. Furthermore, if the lysin is administered concomitantly with an antibiotic, the amount of lysin may be adjusted based on the amount needed to resensitize the target bacteria to the concomitantly administered antibiotic.

"Co-administer" is intended to embrace separate administration of a lysin polypeptide and an antibiotic or any other antibacterial agent in a sequential manner as well as administration of these agents in a substantially simultaneous manner, such as in a single mixture/composition or in doses given separately, but nonetheless administered substantially simultaneously to the subject, for example at different times in the same day or 24-hour period. Such co-administration of lysin polypeptides with one or more additional antibacterial agents can be provided as a continuous treatment lasting up to days, weeks, or months. Additionally, depending on the use, the co-administration need not be continuous or coextensive. For example, if the use were as a topical antibacterial agent to treat, e.g., a bacterial ulcer or an infected diabetic ulcer, the lysin could be administered only initially within 24 hours of the first antibiotic use and then the antibiotic use may continue without further administration of lysin.

"Subject" refers to a subject to be treated and includes inter alia a mammal, a plant, a lower animal, a single cell organism or a cell culture. For example, the term "subject" is intended to include organisms, e.g., prokaryotes and eukaryotes, which are susceptible to or afflicted with bacterial infections, for example Gram-negative bacterial infections. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or susceptible to infection by Gram-negative bacteria against which the wild type (parent) lysin is effective, whether such infection be systemic, topical or otherwise concentrated or confined to a particular organ or tissue.

"Polypeptide" is used herein interchangeably with the term "protein" and "peptide" and refers to a polymer made from amino acid residues and generally having at least about 30 amino acid residues. The term includes not only polypeptides in isolated form, but also active fragments and derivatives thereof. The term "polypeptide" also encompasses fusion proteins or fusion polypeptides comprising a lysin polypeptide as described below and maintaining the lysin function. Depending on context, a polypeptide or protein or peptide can be a naturally occurring polypeptide or a recombinant, engineered or synthetically produced polypeptide. A particular lysin polypeptide can be, for example, derived or removed from a native protein (i.e., a protein with an amino acid sequence identical to that isolated for this protein from natural sources) by enzymatic or chemical cleavage, or can be prepared using conventional peptide synthesis techniques (e.g., solid phase synthesis) or molecular biology techniques (such as those disclosed in Sambrook, J. et al., Molecular Cloning: A Laboratory Manual, Cold Spring Harbor Press, Cold Spring Harbor, N.Y. (1989)) or can be strategically truncated or segmented yielding active fragments, maintaining lysin activity against the same or at least one common target bacterium.

"Fusion polypeptide" refers to an expression product resulting from the fusion of two or more nucleic acid segments, resulting in a fused expression product typically having two domains or segments with different properties or functionality. In a more particular sense, the term "fusion polypeptide" also refers to a polypeptide or peptide comprising two or more heterologous polypeptides or peptides covalently linked, either directly or via an amino acid or peptide linker. The polypeptides forming the fusion polypeptide are typically linked C-terminus to N-terminus, although they can also be linked C-terminus to C-terminus, N-terminus to N-terminus, or N-terminus to C-terminus. The term "fusion polypeptide" can be used interchangeably with the term "fusion protein." Thus, the open-ended expression "a polypeptide comprising" a certain structure includes larger molecules than the recited structure such as fusion polypeptides.

"Heterologous" refers to nucleotide, peptide, or polypeptide sequences that are not naturally contiguous. For example, in the context of the present disclosure, the term "heterologous" can be used to describe a combination or fusion of two or more peptides and/or polypeptides wherein the fusion peptide or polypeptide is not normally found in nature, such as for example a lysin polypeptide or active fragment thereof and a cationic and/or a polycationic peptide, an amphipathic peptide, a sushi peptide (Ding et al. Cell Mol Life Sci., 65(7-8):1202-19 (2008)), a defensin peptide (Ganz, T. Nature Reviews Immunology 3, 710-720 (2003)), a hydrophobic peptide and/or an antimicrobial peptide which may have enhanced lysin activity. Included in this definition are two or more lysin polypeptides or active fragments thereof. These can be used to make a fusion polypeptide with lysin activity.

"Active fragment" refers to a portion of a full-length polypeptide disclosed herein which retains one or more functions or biological activities of the isolated polypeptide from which the fragment was taken, for example bactericidal activity against one or more Gram-negative bacteria, or more specifically lytic activity, whether or not it retains the ability to bind to the outer membrane.

"Amphipathic peptide" refers to a peptide having both hydrophilic and hydrophobic functional groups. Preferably, secondary structure places hydrophobic and hydrophilic amino acid residues at opposite sides (e.g., inner side vs outer side) of an amphipathic peptide. These peptides often adopt a helical secondary structure.

"Cationic peptide" refers to a peptide having a high percentage of positively charged amino acid residues. Preferably, a cationic peptide has a pKa-value of 8.0 or greater. The term "cationic peptide" in the context of the present disclosure also encompasses polycationic peptides which are synthetically produced peptides composed of mostly positively charged amino acid residues, in particular lysine and/or arginine residues. The amino acid residues that are not positively charged can be neutrally charged amino acid residues and/or negatively charged amino acid residues and/or hydrophobic amino acid residues.

"Hydrophobic group" refers to a chemical group such as an amino acid side chain which has low or no affinity for water molecules but higher affinity for oil molecules. Hydrophobic substances tend to have low or no solubility in water or aqueous phases and are typically apolar but tend to have higher solubility in oil phases. Examples of hydrophobic amino acids include glycine (Gly), alanine (Ala), valine (Val), Leucine (Leu), isoleucine (Ile), proline (Pro), phenylalanine (Phe), methionine (Met), and tryptophan (Trp).

"Augmenting" within the context of the present disclosure means that a degree of antimicrobial activity is higher than it would be otherwise. "Augmenting" encompasses additive as well as synergistic (superadditive) effects. For example, structural modifications of native lysins in accordance with the present disclosure serve to augment the activity of the lysin in the presence of serum.

"Synergistic" or "superadditive" in relation to an effect means a beneficial effect brought about by two active substances in combination that exceeds, preferably significantly, the sum of the effects of the two agents working independently. One or both active ingredients may be employed at a subthreshold level, i.e., a level at which if the active substance is employed individually produces no or a very limited effect, (or at the very least a suboptimal level, i.e., a level at which the active substance produces an effect substantially below its maximum effect). Alternatively, the effect can be measured by assays such as the checkerboard assay, described here.

"Treatment" refers to any process, action, application, therapy, or the like, wherein a subject, including a human being, is subjected to medical aid with the object of curing a disorder, or eradicating a pathogen, or improving the subject's condition, directly or indirectly. Treatment also refers to reducing incidence, or alleviating symptoms, eliminating recurrence, preventing recurrence, preventing incidence, or reducing the risk of incidence, improving symptoms, improving prognosis or combinations thereof. "Treatment" further encompasses reducing the population, growth rate or virulence of the bacteria in the subject and thereby controlling or reducing a bacterial infection in a subject or bacterial contamination of an organ or tissue or environment. Thus "treatment" that reduces incidence is effective to inhibit growth of at least one Gram-positive bacterium in a particular milieu, whether it be a subject or an environment. On the other hand, "treatment" of an already established infection refers to reducing the population or killing, inhibiting the growth including even eradicating the Gram-positive bacteria responsible for an infection or contamination.

The term "preventing" includes the prevention of the incidence, recurrence, spread, onset or establishment of a disorder such as a bacterial infection. It is not intended that the present disclosure be limited to complete prevention or to prevention of establishment of an infection. In some embodiments, the onset is delayed, or the severity of a subsequently contracted disease or the chance of contracting it is reduced, and such constitute examples of prevention.

Contracted diseases in the context of the present disclosure encompass both those manifesting with clinical or subclinical symptoms, such as the detection of fever, sepsis or bacteremia (BSI), as well as the detection of growth of a bacterial pathogen (e.g., in culture) when symptoms associated with such pathology are not yet manifest.

The term "derivative" in the context of a peptide or polypeptide (which as stated herein includes an active fragment) is intended to encompass for example, a polypeptide modified to contain one or more-chemical moieties other than an amino acid that do not substantially adversely impact or destroy the lysin activity. The chemical moiety can be linked covalently to the peptide, e.g., via an amino terminal amino acid residue, a carboxy terminal amino acid residue, or at an internal amino acid residue. Such modifications include the addition of a protective or capping group on a reactive moiety, addition of a detectable label, such as antibody and/or fluorescent label, addition or modification of glycosylation, or addition of a bulking group such as PEG (pegylation) and other changes that do not substantially adversely impact or destroy the activity of the lysin polypeptide. Commonly used protective groups that may be added to lysin polypeptides include, but are not limited to t-Boc and Fmoc. Commonly used fluorescent label proteins such as, but not limited to, green fluorescent protein (GFP), red fluorescent protein (RFP), cyan fluorescent protein (CFP), yellow fluorescent protein (YFP) and mCherry, are compact proteins that can be bound covalently or noncovalently to a lysin polypeptide or fused to a lysin polypeptide without interfering with normal functions of cellular proteins. Typically, a polynucleotide encoding a fluorescent protein is inserted upstream or downstream of the lysin polynucleotide sequence. This will produce a fusion protein (e.g., Lysin Polypeptide::GFP) that does not interfere with cellular function or function of a lysin polypeptide to which it is attached. Polyethylene glycol (PEG) conjugation to proteins has been used as a method for extending the circulating half-life of many pharmaceutical proteins. Thus, in the context of lysin polypeptide derivatives, the term "derivative" encompasses lysin polypeptides chemically modified by covalent attachment of one or more PEG molecules. It is anticipated that pegylated lysin polypeptides will exhibit prolonged circulation half-life compared to the unpegylated lysin polypeptides, while retaining biological and therapeutic activity. Another example is the use of "artilysins", whereby a short polycationic and amphipathic alpha helices are appended to the N- or C-termini of a streptococcal lysin to improve in vitro anti-streptococcal activity (Rodriguez-Rubio et al., 2016).

"Percent amino acid sequence identity" with respect to the lysin polypeptide sequences is defined herein as the percentage of amino acid residues in a candidate sequence that are identical with the amino acid residues in the specific lysin polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publicly available software such as BLAST or software available commercially for example from DNASTAR. Two or more polypeptide sequences can be anywhere from 0-100% identical, or any integer value there between. In the context of the present disclosure, two polypeptides are "substantially identical" when at least 80% of the amino acid residues (preferably at least about 85%, at least about 90%, and preferably at least about 95%) are identical.

The term "percent (%) amino acid sequence identity" as described herein applies to lysin peptides as well. Thus, the term "substantially identical" will encompass mutated, truncated, fused, or otherwise sequence-modified variants of isolated lysin polypeptides and peptides described herein, and active fragments thereof, as well as polypeptides with substantial sequence identity (e.g., at least 80%, at least 85%, at least 90%, or at least 95% identity as measured for example by one or more methods referenced above) as compared to the reference (wild type or other intact) polypeptide. Two amino acid sequences are "substantially homologous" when at least about 80% of the amino acid residues (preferably at least about 85%, at least about 90%, and preferably at least about 95% or 98%) are identical, or represent conservative substitutions. The sequences of lysin polypeptides of the present disclosure, are substantially homologous when one or more, or several, or up to 10%, or up to 15%, or up to 20% of the amino acids of the lysin polypeptide are substituted with a similar or conservative amino acid substitution, and wherein the resulting lysin have the profile of activities, antibacterial effects, and/or bacterial specificities of lysin polypeptides disclosed herein. The meaning of "substantially homologous" described herein applies to lysin peptides as well.

"Inhalable composition" refers to pharmaceutical compositions of the present disclosure that are formulated for direct delivery to the respiratory tract during or in conjunction with routine or assisted respiration (e.g., by intratracheobronchial, pulmonary, and/or nasal administration), including, but not limited to, atomized, nebulized, dry powder and/or aerosolized formulations.

"Biofilm" refers to bacteria that attach to surfaces and aggregate in a hydrated polymeric matrix that may be comprised of bacterial- and/or host-derived components. A biofilm is an aggregate of microorganisms in which cells adhere to each other on a biotic or abiotic surface. These adherent cells are frequently embedded within a matrix comprised of, but not limited to, extracellular polymeric substance (EPS). Biofilm EPS, which is also referred to as slime (although not everything described as slime is a biofilm) or plaque, is a polymeric conglomeration generally composed of extracellular DNA, proteins, and polysaccharides.

"Suitable" in the context of an antibiotic being suitable for use against certain bacteria refers to an antibiotic that was found to be effective against those bacteria even if resistance subsequently developed.

Identification of Lysins with Bactericidal Activity Against *P. aeruginosa* in Human Serum. The present disclosure is based on identification of five lysins with potent antibacterial activity against exponential phase *Pseudomonas aeruginosa* strain PAOI (Examples 1 and 2). This strain is representative of *P. aeruginosa* strains. To identify the lysin polypeptides of the present disclosure, the inventors used a bioinformatics-based approach coupled with an antibacterial screen. Putative lysins and lysin-like molecules (see Table 1) were identified from the GenBank database. The GenBank sequences were annotated as either hypothetical or predicted proteins, and in some cases were listed as putative phage proteins and/or putative lysins). The inventors were not aware of any reports of activity for these polypeptides. Nor could their activity be predicted from their sequence, much less their activity in the presence of human serum.

TABLE 1

| Lysin | pI | GenBank Acsession No. |
|---|---|---|
| GN3 | 9.98 | WP_012273008.1 |
| GN13 | 9.47 | YP_00638255.1 |
| GN17 | 7.85 | ACD38663.1 |
| GN9 | 8.85 | ECJ78460.1 |
| GN10 | 9.70 | YP_002600773.1 |
| GN105 | 9.01 | WP_016046696.1 |

TABLE 1-continued

| Lysin | pI | GenBank Acsession No. |
|---|---|---|
| GN108 | 9.28 | YP_009288673.1 |
| GN123 | 9.30 | YP_009217242.1 |
| GN150 | 9.30 | WP_034684053.1 |
| GN203 | 7.87 | YP_024745.1 |

Identification of Modified Lysins with Improved Bactericidal Activity Against *P. aeruginosa* in Human Serum. Five lysins, GN3, GN150, GN203, GN4 and GN37, were used to generate 12 novel GN-lysin derivatives. See Table 2. It is contemplated that the modifications (amino acid substitutions or N- or C-terminal peptide fusion with or without linker) could be individually or simultaneously applied to a native lysin or to a modified lysin. Thus, for example, the addition of an N- and/or C-terminal peptide disclosed in Table 2 is contemplated for modifying lysin polypeptides. As a more specific example, the peptide that is part of GN156 or GN92 is contemplated for GN147 even though such a construct has not been exemplified in Table 2. And such a peptide can be added for example to either GN4 or GN146. In other words, an antimicrobial peptide can be fused to the N- or the C-terminus of a native lysin or a lysin modified by noncharged amino acid substitutions in place of charged amino acid residues. Furthermore, the N-terminal and/or C-terminal peptides and/or antimicrobial peptides may be connected to a lysin polypeptide via a linker domain, for example, a linker domain defined in Table 2 or another appropriate linker, as described in this section above.

TABLE 2

| Lysin | pI | Native Lysin (Accession number/Class)* | Modification |
|---|---|---|---|
| GN147 | 9.39 | GN3 (WP_012273008.1/Lysozyme) | Amino acid substitutions (R100D, R116H) |
| GN146 | 8.01 | GN4 (YP_002284361.1/Lysozyme) | Amino acid substitutions (K100D, R116H) |
| GN156 | 10.51 | GN4 (YP_002284361.1/Lysozyme) | Addition of N-terminal peptide (GPRRPRRPGRRAPV; SEQ ID NO: 28) |
| GN92 | 9.93 | GN4 (YP_002284361.1/Lysozyme) | Addition of N-terminal peptide (KFFKFFKFFK; SEQ ID NO: 29) with linker (AGAGAGAGAGAGAGAS; SEQ ID NO: 31) |
| GN54 | 10.34 | GN4 (YP_002284361.1/Lysozyme) | Addition of N-terminal peptide (KRKKRKKRK; SEQ ID NO: 30) with linker (AGAGAGAGAGAGAGAS; SEQ ID NO: 31) |
| GN201 | 10.47 | GN3 (WP_012273008.1/Lysozyme) | Addition of C-terminal peptide (GPRRPRRPGRRAPV; SEQ ID NO: 28); Amino acid substitutions (R100D, R116H) |
| GN202 | 10.13 | GN4 (YP_002284361.1/Lysozyme) | Addition of C-terminal peptide (GPRRPRRPGRRAPV; SEQ ID NO: 28); Amino acid substitutions (K100D, R116H) |
| GN121 | 10.13 | GN37 (WP_014102102.1/VanY) | Addition of C-terminal peptide (RKKTRKRLKKIGKVLKWI; SEQ ID NO: 32) |

TABLE 2-continued

| Lysin | pI | Native Lysin (Accession number/Class)* | Modification |
|---|---|---|---|
| GN94 | 9.77 | GN37 (WP_014102102.1/VanY) | Addition of N-terminal peptide (KFFKFFKFFK; SEQ ID NO: 29) with linker (AGAGAGAGAGAGAGAS; SEQ ID NO: 31) |
| GN200 | 9.97 | GN150 (WP_034684053.1/VanY) | Addition of C-terminal peptide (RKKTRKRLKKIGKVLKWI; SEQ ID NO: 32) |
| GN204 | 9.88 | GN203 (YP_024745.1/VanY) | Addition of C-terminal peptide (RKKTRKRLKKIGKVLKWI; SEQ ID NO: 32) |
| GN205 | 11.02 | GN3 (WP_012273008.1/Lysozyme) | Addition of N-terminal peptide (GPRRPRRPGRRAPV; SEQ ID NO:28) |

The present lysins and modified GN-lysins and their amino acid sequences are summarized in Table 3. Also included in Table 3 are unmodified lysins disclosed in WO/2017/049233, as stated above.

TABLE 3

| Lysin | Amino Acid Sequence |
|---|---|
| GN2 | MKISLEGLSLIKKFEGCKLEAYKCSAGVWTIGYGHTAGVKEGDVCTQEEA EKLLRGDIFKFEEYVQDSVKVDLDQSQFDALVAWTFNLGPGNLRSSTMLK KLNNGEYESVPFEMRRWNKAGGKTLDGLIRRRQAESLLFESKEWHQV (SEQ ID NO: 1) |
| GN3 | MRTSQRGLSLIKSFEGLRLQAYQDSVGVWTIGYGTTRGVKAGMKISKDQ AERMLLNDVQRFEPEVERLIKVPLNQDQWDALMSFTYNLGAANLESSTLR RLLNAGNYAAAAEQFPRWNKAGGQVLAGLTRRRAAERELFLGAA (SEQ ID NO: 2) |
| GN4 | MRTSQRGIDLIKSFEGLRLSAYQDSVGVWTIGYGTTRGVTRYMTITVEQA ERMLSNDIQRFEPELDRLAKVPLNQNQWDALMSFVYNLGAANLASSTLLK LLNKGDYQGAADQFPRWVNAGGKRLDGLVKRRAAERALFLEPLS (SEQ ID NO: 3) |
| GN146 | MRTSQRGIDLIKSFEGLRLSAYQDSVGVWTIGYGTTRGVTRYMTITVEQA ERMLSNDIQRFEPELDRLAKVPLNQNQWDALMSFVYNLGAANLASSTLLD LLNKGDYQGAADQFPHWVNAGGKRLDGLVKRRAAERALFLEPLS (SEQ ID NO: 4) |
| GN147 | MRTSQRGLSLIKSFEGLRLQAYQDSVGVWTIGYGTTRGVKAGMKISKDQ AERMLLNDVQRFEPEVERLIKVPLNQDQWDALMSFTYNLGAANLESSTLR DLLNAGNYAAAAEQFPHWNKAGGQVLAGLTRRRAAERELFLGAA (SEQ ID NO: 5) |
| GN156 | GPRRPRRPGRRAPVMRTSQRGIDLIKSFEGLRLSAYQDSVGVWTIGYGT TRGVTRYMTITVEQAERMLSNDIQRFEPELDRLAKVPLNQNQWDALMSF VYNLGAANLASSTLLKLLNKGDYQGAADQFPRWVNAGGKRLDGLVKRRA AERALFLEPLS (SEQ ID NO: 6) |
| GN92 | KFFKFFKFFKAGAGAGAGAGAGAGAGASMRTSQRGIDLIKSFEGLRLSAY QDSVGVWTIGYGTTRGVTRYMTITVEQAERMLSNDIQRFEPELDRLAKVP LNQNQWDALMSFVYNLGAANLASSTLLKLLNKGDYQGAADQFPRWVNA GGKRLDGLVKRRAAERALFLEPLS (SEQ ID NO: 7) |
| GN54 | KRKKRKKRKAGAGAGAGAGAGAGAGASMRTSQRGIDLIKSFEGLRLSAY QDSVGVWTIGYGTTRGVTRYMTITVEQAERMLSNDIQRFEPELDRLAKVP LNQNQWDALMSFVYNLGAANLASSTLLKLLNKGDYQGAADQFPRWVNA GGKRLDGLVKRRAAERALFLEPLS (SEQ ID NO: 8) |
| GN202 | MRTSQRGIDLIKSFEGLRLSAYQDSVGVWTIGYGTTRGVTRYMTITVEQA ERMLSNDIQRFEPELDRLAKVPLNQNQWDALMSFVYNLGAANLASSTLLD LLNKGDYQGAADQFPHWVNAGGKRLDGLVKRRAAERALFLEPLSGPRR PRRPGRRAPV (SEQ ID NO: 9) |
| GN14 | MNNELPWVAEARKYIGLREDTSKTSHNPKLLAMLDRMGEFSNESRAWW HDDETPWCGLFVGYCLGVAGRYVVREWYRARAWEAPQLTKLDRPAYGA LVTFTRSGGGHVGFIVGKDARGNLMVLGGNQSNAVSIAPFAVSRVTGYF WPSFWRNKTAVKSVPFEERYSLPLLKSNGELSTNEA (SEQ ID NO: 10) |

TABLE 3-continued

| Lysin | Amino Acid Sequence |
|---|---|
| GN43 | MKRTTLNLELESNTDRLLQEKDDLLPQSVTNSSDEGTPFAQVEGASDDNT AEQDSDKPGASVADADTKPVDPEWKTITVASGDTLSTVFTKAGLSTSAMH DMLTSSKDAKRFTHLKVGQEVKLKLDPKGELQALRVKQSELETIGLDKTD KGYSFKREKAQIDLHTAYAHGRITSSLFVAGRNAGLPYNLVTSLSNIFGYDI DFALDLREGDEFDVIYEQHKVNGKQVATGNILAARFVNRGKTYTAVRYTN KQGNTSYYRADGSSMRKAFIRTPVDFARISSRFSLGRRHPILNKIRAHKGV DYAAPIGTPIKATGDGKILEAGRKGGYGNAVVIQHGQRYRTIYGHMSRFA KGIRAGTSVKQGQIIGYVGMTGLATGPHLHYEFQINGRHVDPLSAKLPMA DPLGGADRKRFMAQTQPMIARMDQEKKTLLALNKQR (SEQ ID NO: 11) |
| GN37 | MTYTLSKRSLDNLKGVHPDLVAVVHRAIQLTPVDFAVIEGLRSVSRQKELV AAGASKTMNSRHLTGHAVDLAAYVNGIRWDWPLYDAIAVAVKAAAKELG VAIVWGGDWTTFKDGPHFELDRSKYR (SEQ ID NO: 12) |
| GN121 | MTYTLSKRSLDNLKGVHPDLVAVVHRAIQLTPVDFAVIEGLRSVSRQKEL VAAGASKTMNSRHLTGHAVDLAAYVNGIRWDWPLYDAIAVAVKAAAKEL GVAIVWGGDWTTFKDGPHFELDRSKYRRKKTRKRLKKIGKVLKWI (SEQ ID NO: 13) |
| GN94 | KFFKFFKFFKAGAGAGAGAGAGAGAGASMTYTLSKRSLDNLKGVHPDL VAVVHRAIQLTPVDFAVIEGLRSVSRQKELVAAGASKTMNSRHLTGHAVD LAAYVNGIRWDWPLYDAIAVAVKAAAKELGVAIVWGGDWTTFKDGPHFEL DRSKYR (SEQ ID NO: 14) |
| GN201 | MRTSQRGLSLIKSFEGLRLQAYQDSVGVWTIGYGTTRGVKAGMKISKDQ AERMLLNDVQRFEPEVERLIKVPLNQDQWDALMSFTYNLGAANLESSTLR DLLNAGNYAAAAEQFPHWNKAGGQVLAGLTRRRAAERELFLGAAGPRR PRRPGRRAPV (SEQ ID NO: 15) |
| GN205 | GPRRPRRPGRRAPVMRTSQRGLSLIKSFEGLRLQAYQDSVGVWTIGYGT RGVKAGMKISKDQAERMLLNDVQRFEPEVERLIKVPLNQDQWDALMSFT YNLGAANLESSTLRRLLNAGNYAAAAEQFPRWNKAGGQVLAGLTRRRAA ERELFLGAA (SEQ ID NO: 16) |
| GN200 | MSFKLGKRSLSNLEGVHPDLIKVVKRAIELTECDFTVTEGLRSKERQAQL LKEKKTTTSNSRHLTGHAVDLAAWVNNTVSWDWKYYYQIADAMKKAASE LNVSIDWGGDWKKFKDGPHFELTWSKYPIKGASRKKTRKRLKKIGKVLK WI (SEQ ID NO: 17) |
| GN204 | MKLSEKRALFTQLLAQLILWAGTQDRVSVALDQVKRTQAEADANAKSGA GIRNSLHLLGLAGDLILYKDGKYMDKSEDYKFLGDYWKSLHPLCRWGGD FKSRPDGNHFSLEHEGVQRKKTRKRLKKIGKVLKWI (SEQ ID NO: 18) |
| GN150 | MSFKLGKRSLSNLEGVHPDLIKVVKRAIELTECDFTVTEGLRSKERQAQLL KEKKTTTSNSRHLTGHAVDLAAWVNNTVSWDWKYYYQIADAMKKAASEL NVSIDWGGDWKKFKDGPHFELTWSKYPIKGAS (SEQ ID NO: 19) |
| GN203 | MKLSEKRALFTQLLAQLILWAGTQDRVSVALDQVKRTQAEADANAKSGA GIRNSLHLLGLAGDLILYKDGKYMDKSEDYKFLGDYWKSLHPLCRWGGD FKSRPDGNHFSLEHEGVQ (SEQ ID NO: 20) |
| GN9 | MKNFNEIIEHVLKHEGGYVNDPKDLGGETKYGITKRFYPDLDIKNLTIEQAT EIYKKDYWDKNKVESLPQNLWHIYFDMCVNMGKRTAVKVLQRAAVNRGR DIEVDGGLGPATIGALKGVELDRVRAFRVKYYVDLITARPEQEKFYLGW FRRATEV (SEQ ID NO: 21) |
| GN10 | MSKQGGVKVAQAVAALSSPGLKIDGIVGKATRAAVSSMPSSQKAATDKIL QSAGIGSLDSLLAEPAAATSDTFREVVLAVAREARKRGLNPAFYVAHIAL ETGWGRSVPKLPDGRSSYNYAGLKYAAVKTQVKGKTETNTLEYIKSLPKT VRDSFAVFASAGDFSRVYFWYLLDSPSAYRYPGLKNAKTAQEFGDILQKG GYATDPAYAAKVASIASTAVARYGSDVSSVA (SEQ ID NO: 22) |
| GN13 | MSDKRVEITGNVSGFFESGGRGVKTVSTGKGDNGGVSYGKHQLASNNG SMALFLESPFGAPYRAQFAGLKPGTAAFTSVYNKIANETPTAFERDQFQYI AASHYDPQAAKLKAEGINVDDRHVAVRECVFSVAVQYGRNTSIIIKALGSN FRGSDKDFIEKVQDYRGATVNTYFKSSSQQTRDSVKNRSQQEKQMLLKL LNS (SEQ ID NO: 23) |
| GN17 | MTLRYGDRSQEVRQLQRRLNTWAGANLYEDGHFGAATEDAVRAFQRSH GLVADGIAGPKTLAALGGADCSHLLQNADLVAAATRLGLPLATIYAVNQVE SNGQGFLGNGKPAILFERHIMYRRLAAHDQVTADQLAAQFPALVNPRPG GYAGGTAEHQRLANARQIDDTAALESASWGAFQIMGFHWQRLGYISVQA FAEAMGRSESAQFEAFVRFIDTDPALHKALKARKWADFARLYNGPDYKR NLYDNKLARAYEQHANCAEASA (SEQ ID NO: 24) |

TABLE 3-continued

| Lysin | Amino Acid Sequence |
|---|---|
| GN105 | MAVVSEKTAGGRNVLAFLDMLAWSEGTSTIRGSDNGYNVVVGGGLFNG<br>YADHPRLKVYLPRYKVYSTAAGRYQLLSRYWDAYRESLALKGGFTPSNQ<br>DLVALQQIKERRSLADIQAGRLADAVQKCSNIWASLPGAGYGOREHSLDD<br>LTAHYLAAGGVLS (SEQ ID NO: 25) |
| GN108 | MILTKDGFSIIRNELFEGKLDQTQVDAINFIVEKATEYGLTYPEAAYLLATIY<br>HETGLPSGYRTMQPIKEAGSDSYLRSKKYYPYIGYGYVQLTWEENYERIG<br>KLIGIDLVKNPEKALEPLIAIQIAIKGMLNGWFTGVGFRRKRPVSKYNKQQY<br>VAARNIINGKDKAELIAKYAIIFERALRSL (SEQ ID NO: 26) |
| GN123 | MTLLKKGDKGDAVKQLQQKLKDLGYTLGVDGNFGNGTDTVVRSFQTKM<br>KLSVDGVVGNGTMSTIDSTLAGIKAWKTSVPFPATNKSRAMAMPTLTEIG<br>RLTNVDPKLLATFCSIESAFDYTAKPYKPDGTVYSSAEGWFQFLDATWDD<br>EVRKHGKQYSFPVDPGRSLRKDPRANGLMGAEFLKGNAAILRPVLGHEP<br>SDTDLYLAHFMGAGGAKQFLMADQNKLAAELFPGPAKANPNIFYKSGNIA<br>RTLAEVYAVLDAKVAKHRA (SEQ ID NO: 27) |

For GN3 and GN4 (each a member of the lysozyme-like superfamily), the modified derivatives GN147 and GN146, respectively, were generated based on the introduction of two amino acid substitutions at positions equivalent to that shown (31-33) in human lysozyme to improve both in vitro (in buffer and/or media) and in vivo antibacterial activity (in an animal infection model).

The GN3 lysin polypeptide was modified to include amino acid substitutions, in particular, R100D and R116H amino acid substitutions. This resulted in the modified polypeptide, GN147. These amino acid substitutions resulted in a reduction in pI from 9.98 in the GN3 polypeptide to 9.39 in the GN147 polypeptide.

The GN4 lysin was modified to include amino acid substitutions, in particular, K100D, R116H. This resulted in the modified lysin polypeptide, GN146. These amino acid substitutions resulted in reduction in pI from 9.58 in the GN4 polypeptide to 8.01 in the GN146 polypeptide.

The positions for each mutation in GN3 and GN4 were gauged based on a rough comparison with mutations in human lysozyme (HuLYZ), as HuLYZ bears no significant homology to either GN3 or GN4 at the amino acid sequence level.

While lysins GN3 and GN4 are not similar to T4 lysozyme at the amino acid level, they are of a similar size. A line up of their structures revealed charged residues. Equivalence was therefore judged solely by the presence of a charged residue in GN3 and GN4 at roughly the same location in the primary sequence of T4 lysozyme. Again, as described above, in general, charged amino acids were substituted by ones having no charge and the mutants screened for activity.

Additional modifications of both GN3 and GN4 polypeptides were also introduced, including the addition of an N-terminal peptide sequence (GPRRPRRPGRRAPV-SEQ ID NO:28), derived from a much larger antimicrobial peptide (AMP) described by Daniels and Schepartz, 2007 (34), to generate GN205 and GN156, respectively.

The GN lysin polypeptides may be further modified by the addition of pI modifying mutations. In an embodiment, the amino acid substitutions (R100D) and (R116H) were introduced into the GN3 lysin to generate the GN147 lysin. In another embodiment, the amino acid substitutions (K100D) and (R116H) were introduced into the GN4 lysin to generate the GN146 lysin.

The GN4 polypeptide was also modified by the addition of two different previously described N-terminal cationic AMPs, either KFFKFFKFFK (SEQ ID NO:29) or KRKKRKKRK (SEQ ID NO:30) (35, 36) connected to GN4 via a linker domain AGAGAGAGAGAGAGAGAS (SEQ ID NO:31) previously described by Briers et al. 2014 (36), to generate the modified lysins GN92 and GN54, respectively.

Modifications of the lysins GN37, GN150 and GN203 (each a member of the VanY superfamily) were generated by the addition of a C-terminal AMP, RKKTRKRLK-KIGKVLKWI (SEQ ID NO:32) previously developed as a derivative of the porcine myeloid antimicrobial peptide-36 (PMAP-36) (22). The modification of GN37, GN150 and GN203 by addition of the C-terminal RI18 peptide sequence resulted in the modified derivatives GN121, GN200, and GN204, respectively. An additional modification was also included whereby the AMP (KFFKFFKFFK-SEQ ID NO:29) (35) and linker domain (AGAGAGAGAGAGAGA-GAS-SEQ ID NO:31) (36) described above were appended to the N-terminus of GN37 to generate modified lysin GN94.

The peptides used to make GN121, GN156, GN200, GN201, GN202, GN204 and GN205 are not believed to have been used previously to modify lysins. The rationale for using them was as follows: 1) when added to the indicated lysin, the predicted secondary structure of both the AMP and lysin does not appreciably change or does not change at all (as determined using a known protein structure predicting program) 2) these peptides have been previously described in the literature as having potent activity; and 3) the present inventors tested these AMPs in serum and found potent activity. The same applies for the peptide used in GN92 and GN9. However, a linker sequence was also used in these constructs, to join the AMP and the lysin, to obtain an appropriate secondary structure of the AMP (closely resembling that of free AMP) when the AMP is fused to the lysin.

For GN54, both the AMP and the linker have been previously used to modify lysins but no reports of activity in serum have been seen in the literature. GN54, does have activity in serum.

Lysins GN3, GN9, GN10, GN13, GN17, GN105, GN108, GN123 and GN150 have been synthesized and/or produced recombinantly, and purified to (>90%) homogeneity and examined in a series of activity assays. The MIC assay was performed using *Pseudomonas aeruginosa* cultured in two media types, CAA and CAA supplemented with 25% human serum ("CAA/HuS"). The activity of many GN lysins (including the control T4 lysozyme in Table 4) is repressed in both CAA and CAA/HuS.

For the set of 9 novel GN lysins examined here (i.e., GN3, GN9, GN10, GN13, GN17, GN105, GN108, GN123, and GN150), we observed an MIC range of 2→128 in both CAA and CAA/HuS.

Modified lysins GN54, GN92, GN94, GN121, GN146 and GN147 were each purified to (>90%) homogeneity and examined in a series of in vitro activity assays. The MIC value (in µg/mL) for each of the GN lysins in CAA/HuS is as follows: GN54, 2; GN92, 4; GN94, 2; GN121, 0.5; GN146, 2; GN147, 4, as shown in Table 4.

TABLE 4

Minimal Inhibitory Concentration (MIC) analysis of Purified GN Lysins.

| Lysin | Lysin Type | MIC (µg/mL) in CAA | MIC (µg/mL in CAA/HuS |
|---|---|---|---|
| GN3 | Native | 16 | 16 |
| GN147 | Modified GN3 | 2 | 4 |
| GN4 | Native | 64 | 16 |
| GN146 | Modified GN4 | 2 | 2 |
| GN156 | Modified GN4 | 32 | 2 |
| GN54 | Modified GN4 | 64 | 2 |
| GN92 | Modified GN4 | 32 | 4 |
| GN37 | Native | >128 | 32 |
| GN121 | Modified GN37 | 0.5 | 0.5 |
| GN94 | Modified GN37 | 16 | 2 |
| GN9 | Native | 8 | 2 |
| GN10 | Native | 8 | 16 |
| GN13 | Native | 8 | >128 |
| GN17 | Native | 32 | 16 |
| GN105 | Native | >128 | 32 |
| GN108 | Native | 8 | 8 |
| GN123 | Native | 2 | 128 |
| GN150 | Native | 2 | 32 |
| GN126 | Native (control) | 2 | 128 |
| T4 LYZ | Native (control) | >128 | >128 |

Significantly, the MIC values (in µg/mL) determined using CAA/HuS for each of the parental lysin molecules GN3, GN4, and GN37 are 16, 16 and 32, respectively; therefore, the modification of each agent resulted in an improvement of activity in human serum. T4 lysozyme (MIC=>128 µg/mL) was included as a control standard for GN lysins that are inactive in human serum. GN126 (MIC=128 µg/mL) was also included as a control, and corresponds to Art-175 (37); Art-175 is an artilysin, described in the literature, consisting of a fusion of the AMP SMAP-29 to GN lysin KZ144.

In addition to the MIC analysis, the modified GN lysins (GN54, GN92, GN94, GN121, GN146 and GN147) were also shown to have potent anti-biofilm activity, wherein the Minimal Biofilm Eradicating Concentration (MBEC) values range from 0.25-2 µg/mL, see Table 5.

Each of the GN3, GN9, GN10, GN13, GN17, GN105, GN108 and GN123 were shown to have potent antibiofilm activity with MBEC values ranging from 0.125-4 µg/mL (Table 5) and have no hemolytic activity whatsoever (Table 6). It is anticipated that the remaining modified lysins will exhibit improved activity against biofilm compared to the parent lysins and will also have reduced or eliminated hemolytic properties as well as increased activity in the presence of blood matrices including human serum.

TABLE 5

Minimal Biofilm Eradicating Concentration (MBEC) Analysis of Purified GN Lysins

| Lysin | Lysin Type | MBEC (µg/mL) |
|---|---|---|
| GN3 | Native | 0.25 |
| GN147 | Modified GN3 | 0.25 |
| GN4 | Native | 1 |
| GN146 | Modified GN4 | 2 |
| GN156 | Modified GN4 | 0.5 |
| GN54 | Modified GN4 | n.d. |
| GN92 | Modified GN4 | 0.5 |
| GN37 | Native | 0.25 |
| GN121 | Modified GN37 | 0.25 |
| GN94 | Modified GN37 | 2 |
| GN9 | Native | 0.125 |
| GN10 | Native | 0.5 |
| GN13 | Native | 0.125 |
| GN17 | Native | 0.125 |
| GN105 | Native | 4 |
| GN108 | Native | 0.125 |
| GN123 | Native | 4 |
| GN150 | Native | 0.25 |

The modified GN lysins (GN54, GN92, GN94, GN121, GN146 and GN147) were also shown to have no hemolytic activity (MHC values of >128 µg/mL), see Table 6.

TABLE 6

Minimal Hemolytic Concentration (MHC) Analysis of Purified GN Lysins

| Lysin | Lysin Type | MHC (µg/mL) |
|---|---|---|
| GN3 | Native | >128 |
| GN147 | Modified GN3 | >128 |
| GN4 | Native | >128 |
| GN146 | Modified GN4 | >128 |
| GN156 | Modified GN4 | >128 |
| GN54 | Modified GN4 | >128 |
| GN92 | Modified GN4 | >128 |
| GN37 | Native | >128 |
| GN121 | Modified GN37 | >128 |
| GN94 | Modified GN37 | >128 |
| GN9 | Native | >128 |
| GN10 | Native | >128 |
| GN13 | Native | >128 |
| GN17 | Native | >128 |
| GN105 | Native | >128 |
| GN108 | Native | >128 |
| GN123 | Native | >128 |
| GN150 | Native | >128 |

The modified GN lysins (GN54, GN92, GN94, GN121, GN146 and GN147) were also shown to have bactericidal activity in the time-kill format, as defined by CFU decreases of ≥3–$Log_{10}$ by 3 hours after the addition of lysin. See Table 7 and Table 8.

In the time-kill assay format, GN3, GN17, GN108, GN123, and GN150 each demonstrated bactericidal activity at a 3-hour timepoint after addition at a concentration of 10 μg/mL in either CAA/HuS or HEPES buffer (Tables 7 and 8, respectively).

TABLE 7

Time-Kill Analysis of Purified GN Lysin Activity in CAA/HuS

| Lysin | Lysin Type | $Log_{10}$ CFU/mL | | |
|---|---|---|---|---|
| | | T = 0 | T = 1 hr | T = 3 hr* |
| no | Buffer control | 7.8 | 7.7 | 7.2 |
| GN3 | Native | 7.8 | 5.8 | <3.7‡ |
| GN147 | Modified GN3 | 7.8 | 6.5 | 4.2‡ |
| GN4 | Native | 7.8 | 6.0 | <3.7‡ |
| GN146 | Modified GN4 | 7.8 | 5.9 | 4.0‡ |
| GN156 | Modified GN4 | 7.8 | 5.7 | <3.7‡ |
| GN54 | Modified GN4 | 7.8 | n.d. | n.d. |
| GN92 | Modified GN4 | 7.8 | 6.2 | <3.7‡ |
| GN37 | Native | 7.8 | 6.2 | <3.7‡ |
| GN121 | Modified GN37 | 7.8 | 7.4 | <3.7‡ |
| GN94 | Modified GN37 | 7.8 | 6.4 | <3.7‡ |
| GN9 | Native | 7.8 | 6.8 | 7.3 |
| GN10 | Native | 7.8 | 7.4 | 7.4 |
| GN13 | Native | 7.8 | n.d. | n.d. |
| GN17 | Native | 7.8 | 6.4 | 4.2‡ |
| GN105 | Native | 7.8 | 7.0 | 6.3 |
| GN108 | Native | 7.8 | 5.7 | <3.7‡ |
| GN123 | Native | 7.8 | 6.7 | <3.7‡ |
| GN150 | Native | 7.8 | 6.0 | <3.7‡ |

*The limit of detection is 3.7 Log10 CFU/mL.
‡indicates bactericidal activity.

TABLE 8

Time-Kill Analysis of Purified GN Lysin Activity in HEPES Buffer

| Lysin | Lysin Type | $Log_{10}$ CFU/mL | | |
|---|---|---|---|---|
| | | T = 0 | T = 1 hr | T = 3 hr* |
| no | Buffer control | 7.8 | 7.7 | 7.2 |
| GN3 | Native | 7.8 | <3.7‡ | <3.7‡ |

TABLE 8-continued

Time-Kill Analysis of Purified GN Lysin Activity in HEPES Buffer

| Lysin | Lysin Type | $Log_{10}$ CFU/mL | | |
|---|---|---|---|---|
| | | T = 0 | T = 1 hr | T = 3 hr* |
| GN147 | Modified GN3 | 7.8 | <3.7‡ | <3.7‡ |
| GN4 | Native | 7.8 | 5.7 | <3.7‡ |
| GN146 | Modified GN4 | 7.8 | 6.7 | <3.7‡ |
| GN156 | Modified GN4 | 7.8 | 5.7 | <3.7‡ |
| GN54 | Modified GN4 | 7.8 | n.d. | n.d. |
| GN92 | Modified GN4 | 7.8 | 5.7 | <3.7‡ |
| GN37 | Native | 7.8 | 6.3 | <3.7‡ |
| GN121 | Modified GN37 | 7.8 | <3.7‡ | <3.7‡ |
| GN94 | Modified GN37 | 7.8 | 6.0 | <3.7‡ |
| GN9 | Native | 7.8 | 6.7 | 5.7 |
| GN10 | Native | 7.8 | 5.7 | <3.7‡ |
| GN13 | Native | 7.8 | n.d. | n.d. |
| GN17 | Native | 7.8 | 5.4 | <3.7‡ |
| GN105 | Native | 7.8 | 6.6 | <3.7 |
| GN108 | Native | 7.8 | 6.4 | <3.7‡ |
| GN123 | Native | 7.8 | 5.6 | <3.7‡ |
| GN150 | Native | 7.8 | 5.7 | <3.7‡ |

*The limit of detection is 3.7 Log10 CFU/mL.
‡indicates bactericidal activity.

A subset of the GN lysins (GN4, GN37, GN108, and GN150) were examined in the checkerboard assay using CAA/HuS, and shown to synergize with a range of antibiotics including amikacin, azithromycin, aztreonam, ciprofloxacin, colistin, rifampicin, and tobramycin (Table 9).

Importantly, the modified lysins GN92, GN121, and GN147 were each shown to synergize with a range of antibiotics having activity against gram negative bacteria (amikacin, azithromycin, aztreonam, ciprofloxacin, colistin, rifampicin, and tobramycin) in CAA/HuS, as shown in Table 9. These data indicate that the synergy will persist in vivo in the presence of human serum.

TABLE 9

Checkerboard Analysis of Purified GN Lysins with Antibiotics

| | Amikacin | Azithromycin | Aztreonam | Ciprofloxacin | Colistin | Rifampicin | Tobramycin |
|---|---|---|---|---|---|---|---|
| GN4 | 0.531 | 0.094 | 0.156 | 0.250 | 0.156 | 0.156 | 0.375 |
| GN92 | 0.375 | 0.063 | 0.188 | 0.281 | 0.094 | 0.094 | 0.500 |
| GN147 | 0.375 | 0.250 | 0.188 | 0.281 | 0.188 | 0.281 | 0.5 |
| GN37 | 0.125 | 0.188 | 0.531 | 0.281 | 0.156 | 0.281 | 0.156 |
| GN121 | 0.375 | 0.188 | 0.625 | 0.313 | 0.375 | 0.313 | 0.188 |
| GN108 | 0.156 | 0.060 | 0.250 | 0.281 | 0.133 | 0.125 | 0.188 |
| GN150 | 0.313 | 0.125 | 0.188 | 0.250 | 0.094 | 0.094 | 0.500 |

Based on the activity of specific GN lysins in the presence of human serum (and on the nature of their amino acid sequence and homology to other lysins as well as protein expression and purification profiles), it is anticipated that lysins GN3, GN9, GN10, GN13, GN17, GN105, GN108, GN123, GN150 and 203 are superior candidates for further development in either their native lysin form or after further modification in the manner described herein, i.e., with substitution of typically 1 to 3 charged amino acid residues with non-charged residues (and maintenance of activity in the absence and presence of human serum) and/or fusion at the N- or C-terminal to an AMP peptide having an alpha helical structure.

The modified lysins corresponding to GN200-GN205 are still under analysis and may have activities similar to GN54, GN92, GN94, GN121, GN146 and GN147.

The inventors identified GN-lysins with varying levels of activity in the presence of human serum. Additionally, modified GN-lysins were obtained and are demonstrated to exhibit improved activity in the presence of human serum compared to that of the parental lysins or a known lysozyme (T4) or a known artilysin (GN126).

Specific embodiments disclosed herein may be further limited in the claims using "consisting of" and/or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein. The applicants reserve the right to disclaim any embodiment or feature described herein.

EXAMPLES

Example 1. Bacterial strains and growth conditions. Antibacterial screening was performed using a *P. aeruginosa* clinical isolate (CFS-1292) from human blood obtained from the Hospital for Special Surgery in New York (provided by Dr. Lars Westblade, Professor of Pathology and Laboratory Medicine). Strain CFS-1292 was cultured in either lysogeny broth (LB; Sigma-Aldrich), casamino acid (CAA) media (5 g/L casamino acids, Ameresco/VWR; 5.2 mM $K_2HPO_4$, Sigma-Aldrich; 1 mM $MgSO_4$, Sigma-Aldrich) or CAA supplemented with 25% human serum (Type Aft male, pooled; Sigma-Aldrich). For purposes of the present disclosure the particular isolate of *P. aeruginosa* is not important and a commercially available isolate could have been used in the present experiments.

Example 2. Gene synthesis and cloning. All lysins and modified lysins were synthesized as gBlocks (IDT Technologies) and cloned into the arabinose-inducible expression vector pBAD24 (24) by overlap extension PCR or through the ligation of compatible cohesive ends. All constructs were transformed into the *E. coli* strain TOP10 (Thermo Fisher Scientific). Other commercially available expression vectors and systems could have been employed.

Example 3. Identification of lysins with intrinsic activity. A set of up to 250 putative lysins and lysin-like enzymes were identified in the GenBank database of *P. aeruginosa* genomic sequences. Three search methods were used: i) a targeted BLASTp screen of all *P. aeruginosa* genomes using query sequences of known lysins, ii) a keyword-based search of all annotated *P. aeruginosa* genomes, focused on all Superfamily designations associated with lysin (and cell wall hydrolase) catalytic and binding domains; and iii) a visual search among phage sequences of non-annotated genomes for lysin-like genes. Once identified, the lysin sequences were synthesized as gBlocks, cloned into pBAD24 and transformed into *E. coli* TOP10 cells. The *E. coli* clones were then examined in a primary antibacterial activity screen (against live *P. aeruginosa*) using an agar overlay plate-based method (11, 13) with a modification to allow detection of GN lysin activity in overlays comprised of soft agar suspended in 50 mM Tris buffer pH7.5. A set of 109 lytic clones were identified and selected for expression and purification.

Example 4. Expression and Purification of Lysins and Modified Lysins

A wide variety of host/expression vector combinations may be employed in expressing the polynucleotide sequences encoding lysin polypeptides of the present disclosure. Large numbers of suitable vectors are known to those of skill in the art, and are commercially available. Examples of suitable vectors are provided in Sambrook et al, eds., Molecular Cloning: A Laboratory Manual (3rd Ed.), Vols. 1-3, Cold Spring Harbor Laboratory (2001). Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, *papaya* viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Furthermore, said vectors may provide for the constitutive or inducible expression of lysin polypeptides of the present disclosure. More specifically, suitable vectors include but are not limited to derivatives of SV40 and known bacterial plasmids, e.g., *E. coli* plasmids colEI, pCRI, pBR322, pMB9 and their derivatives, plasmids such as RP4, pBAD24 and pBAD-TOPO; phage DNAS, e.g., the numerous derivatives of phage λ, e.g., NM989, and other phage DNA, e.g., M13 and filamentous single stranded phage DNA; yeast plasmids such as the 2 D plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. Many of the vectors mentioned above are commercially available from vendors such as New England Biolabs, Addgene, Clontech, life Technologies etc. many of which also provide suitable host cells).

Additionally, vectors may comprise various regulatory elements (including promoter, ribosome binding site, terminator, enhancer, various cis-elements for controlling the expression level) wherein the vector is constructed in accordance with the host cell. Any of a wide variety of expression control sequences (sequences that control the expression of a polynucleotide sequence operatively linked to it) may be used in these vectors to express the polynucleotide sequences encoding lysin polypeptides. Useful control sequences include, but are not limited to: the early or late promoters of SV40, CMV, vaccinia, polyoma or adenovirus, the lac system, the trp system, the TAO system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, *E. coli* promoter for expression in bacteria, and other promoter sequences known to control the expression of genes of prokaryotic or eukaryotic cells or theft viruses, and various combinations thereof.

A wide variety of host cells are useful in expressing the lysin polypeptides of the present disclosure. Nonlimiting examples of host cells suitable for expression of lysin polypeptides of the present disclosure include well known eukaryotic and prokaryotic hosts, such as strains of *E. coli, Pseudomonas, Bacillus, Streptomyces*, fungi such as yeasts, and animal cells, such as CHO, RH, B-W and L-M cells, African Green Monkey kidney cells (e.g., COS 1, COS 7, BSC1, BSC40, and BMT10), insect cells (e.g., Sf9), and human cells and plant cells in tissue culture. While the expression host may be any known expression host cell, in a preferred embodiment the expression host is one of the strains of *E. coli*. These include, but are not limited to commercially available *E. coli* strains such as Top 10 (Thermo Fisher Scientific), DH5α (Thermo Asher Scientific), XLI-Blue (Agilent Technologies), SCS110 (Stratagene), JM109 (Promega), LMG194 (ATCC), and BL21 (Thermo Fisher Scientific), There are several advantages of using *E. coli* as a host system including: fast growth kinetics, where under the optimal environmental conditions, its doubling time is about 20 min (Sezonov et al., J. Bacterial. 189 8746-8749 (2007)), easily achieved high density cultures, easy and fast transformation with exogenous DNA, etc. Details regarding protein expression in *E. coli*, including plasmid selection as well as strain selection are discussed in details by Rosano, G. and Ceccarelli, E., Front Microbial., 5: 172 (2014).

Efficient expression of lysin polypeptides and vectors thereof depends on a variety of factors such as optimal expression signals (both at the level of transcription and translation), correct protein folding, and cell growth characteristics. Regarding methods for constructing the vector and methods for transducing the constructed recombinant vector into the host cell, conventional methods known in the art can be utilized. While it is understood that not all vectors, expression control sequences, and hosts will function equally well to express the polynucleotide sequences encoding lysin peptides of the present disclosure, one skilled in the art will be able to select the proper vectors, expression control sequences, and hosts without undue experimentation to accomplish the desired expression without departing from the scope of this disclosure. In some embodiments, the present inventors have found a correlation between level of expression and activity of the expressed polypeptide; in *E. coli* expression systems in particular, moderate levels of expression (for example between about 1 and 10 mg/liter) have produced lysin polypeptides with higher levels of activity than those that were expressed at higher levels in in *E. coli* (for example between about 20 and about 100 mg/liter), the latter having sometimes produced wholly inactive polypeptides.

Lysin polypeptides of the present disclosure can be recovered and purified from recombinant cell cultures by well-known methods including without limitation ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography can also employed for lysin polypeptide purification.

Alternatively, the vector system used for the production of lysin polypeptides of the present disclosure may be a cell free expression system. Various cell free expression systems are commercially available, including, but not limited to those available from Promega, LifeTechnologies, Clonetech, etc.

Protein solubilization and purification (using one or more chromatographic techniques) are performed in a well-buffered solution containing a suitable ionic strength of a monovalent salt, e.g., an ionic strength equivalent to 300-500 mM of NaCl.

Immobilized metal affinity chromatography (IMAC) is preferably used as the initial purification step. If additional purification is required, size-exclusion chromatography (gel filtration) can be used in a further step. If necessary, ion exchange chromatography can be used as a final step.

A range of induction times and temperatures were used to identify optimal conditions for protein expression and purification. The main methodologies are described in previous studies (11, 13, 25). Briefly, replicates of each expression clone were induced in both LB and RM media (Thermo Fisher Scientific) over at 2-24 hour period at 24° C.-37° C. The induced cultures were then pelleted and disrupted using BugBuster (Millipore Sigma) before an assessment of soluble protein expression was made by SDS-PAGE and Coomassie staining. The optimal condition for expression of each lysin was then used to scale up production. The purifications were performed using either anion exchange (HiTrap DEAE FF), cation exchange (HiTrap Capto MMC), hydrophobic interaction columns (HiTrap Phenyl FF), and/or size exclusion columns (HiLoad 16/600 SuperDex) with the Akta™ Pure FPLC system running Unicorn 6.3 software. The addition of $Mg^{2+}$ was sometimes used to improve solubility and increase binding capacity to the chromatographic resins. During purification, the target GN lysin was identified by molecular weight using a reducing SDS Page gel. After the last purification step, fractions containing the GN lysin of interest were pooled, buffer exchanged to 25 mM Tris 150 mM sodium chloride with pH value ranging from 7.2 to 9.0 (depending on the pI of the protein) and concentrated to about 2 mg/mL. Concentration was measured by NanoDrop and protein was stored at −80° C. in 500 μL aliquots.

Example 5. Determination of Minimal Inhibitory Concentration (MIC)

The minimal inhibitory concentration of each GN lysin against *P. aeruginosa* was determined using a modification of the standard broth microdilution reference method defined by the Clinical and Laboratory Standards Institute (CLSI)(26). The modification was based on the replacement of Mueller Hinton Broth with either CAA media or CAA supplemented with 25% human serum.

Example 6. Determination of Minimal Biofilm Eradicating Concentration (MBEC). The MBEC of CF-301 was determined using a variation of the broth microdilution MIC method with modifications (27, 28). Here, fresh colonies of *P. aeruginosa* strain ATCC 17647 were suspended in PBS (0.5 McFarland units), diluted 1:100 in TSBg (tryptic soy broth supplemented with 0.2% glucose), added as 0.15 ml aliquots to a Calgary Biofilm Device (96-well plate with a lid bearing 96 polycarbonate pegs; Innovotech) and incubated 24 hours at 37° C. Biofilms were washed and treated with a 2-fold dilution series of CF-301 in TSBg at 37° C. for 24 hours. All samples were examined in triplicate. After treatment, wells were washed, air-dried at 37° C., and stained with 0.05% crystal violet for 10 minutes. After staining, the biofilms were destained in 33% acetic acid and the $OD_{600}$ of extracted crystal violet was determined. The MBEC of each sample was the minimum drug concentration required to remove >95% of the biofilm biomass assessed by crystal violet quantitation.

Example 7. Checkerboard Assay to Examine Synergy with Antibiotics. The checkerboard assays is based on a modification of the CLSI method for MIC determination by broth microdilution (26, 29). Checkerboards were constructed by first preparing columns of a 96-well polypropylene microtiter plate, in which each well had the same amount of antibiotic diluted 2-fold along the horizontal axis. In a separate plate, comparable rows were prepared in which each well had the same amount of GN lysin diluted 2-fold along the vertical axis. The GN lysin and antibiotic dilutions were then combined, so that each column had a constant amount of antibiotic and doubling dilutions of GN lysin, while each row had a constant amount of GN lysin and doubling dilutions of antibiotic. Each well thus had a unique combination of GN lysin and antibiotic. Bacteria were added to the drug combinations at concentrations of $1\times10^5$ CFU/mL in CAA with 25% human serum. The MIC of each drug, alone and in combination, was then recorded after 16 hours at 37° C. in ambient air. Summation fractional inhibitory concentrations ($\Sigma$FICs) were calculated for each drug and the minimum $\Sigma$FIC value ($\Sigma$FICmin) was used to determine synergy. $\Sigma$FICs were calculated as follows: $\Sigma$FIC=FIC A+FIC B, where FIC A is the MIC of each antibiotic in the combination/MIC of each antibiotic alone, and FIC B is the MIC of each GN lysin in the combination/MIC of each GN lysin alone. The combination is considered synergistic when the $\Sigma$FIC is 13.5, strongly additive when the $\Sigma$FIC is >0.5 to <1, additive with the $\Sigma$FIC is 1-<2, and antagonistic when the $\Sigma$FIC is 2.

Example 8. Assay of GN Lysin Hemolytic Activity. The hemolytic activity of the GN lysins was measured as the amount of hemoglobin released by the lysis of human erythrocytes (30). Briefly, 3 ml of fresh human blood cells (hRBCs) obtained from pooled healthy donors (BioreclamationIVT) in a polycarbonate tube containing heparin was centrifuged at 1,000×g for 5 min at 4° C. The erythrocytes obtained were washed three times with phosphate-buffered saline (PBS) solution (pH 7.2) and resuspended in 30 PBS. A 50 pl volume of the erythrocyte solution was incubated with 50 pl of each GN lysin (in PBS) in a 2-fold dilution range (from 128 µg/mL to 0.25 µg/mL) for 1 h at 37° C. Intact erythrocytes were pelleted by centrifugation at 1,000×g for 5 min at 4° C., and the supernatant was transferred to a new 96-well plate. The release of hemoglobin was monitored by measuring the absorbance at 570 nm. As a negative control, hRBCs in PBS were treated as above with 0.1% Triton X-100.

Example 9. Time-Kill Assay of GN Lysin Activity. An overnight culture of *P. aeruginosa* was diluted 1:50 into fresh CAA media and grown for 2.5 hours at 37° C. with agitation. Exponential phase bacteria were then pelleted and resuspended in ⅕ culture volume of 25 mM HEPES, pH7.4 before a final adjustment to an optical density corresponding to a McFarland value of 0.5. The adjusted culture was then diluted 1:50 into either 25 mM HEPES pH7.4 or CAA/HuS and the GN lysins were added at a final concentration of 10 µg/mL. Control cultures were included with the addition of no lysin (i.e., buffer control). All treatments were incubated at 37° C. with aeration. At time points before the addition of lysin (or buffer control) and at 1 hour and 3 hours intervals thereafter, culture samples were removed for quantitative plating on CAA agar plates.

Planned Experiments In Vivo

One or more experiments to test in vivo activity of the present polypeptides are currently in progress as follows:

A. Pilot PK Screening and Efficacy in the Mouse Model for Acute Lethal Bacteremia To identify GN lysins that have systemic exposure, PK screening will be performed in CD1 mice treated with a GN lysin administered as a single IV injection. Blood PK profiles will be analyzed for up to 10 GN lysins using a research grade bioanalytical assay qualified in mouse serum. It is anticipated that multiple GN lysins will be identified that have an appropriate PK profile. Candidates that demonstrate blood exposure that achieves an AUC/MIC concentration greater than 1 will be tested in a systemic infection model. For the model, *P. aeruginosa* strains (PAO1 and other clinical isolates) will be re-suspended in hog gastric mucin and administered by intraperitoneal administration into CD1 mice at an inoculum that produces over 24-48 hours complete morbidity and mortality in control mice. Mice will be dosed with vehicle or a GN lysin by intravenous (IV) injection in the lateral tail vein 2 hours post lethal challenge. Morbidity and mortality will be assessed over 72 hours. It is anticipated that at appropriate dose concentrations, GN lysin treated mice will display reduced morbidity and mortality compared to vehicle controls. Studies may involve co-administration of antibiotics. A. Survival data will be analyzed by Kaplan Meyer Survival analysis using GraphPad prism and an effective concentration of 50% (EC50) calculated for each molecule. It is anticipated that multiple GN lysins with in vivo activity will be identified.

B. GN Lysin Efficacy in an Established Murine Models of Invasive Infection

The goal of this experiment and other mouse models of infection, such as lung and kidney, is to generate efficacy data in these models. The efficacy models proposed in this sub aim generally utilize mouse infections in tissues (thigh, lungs or kidneys) with bacteria. Following treatment with the lysin the bacterial burden in the tissues will be quantitated (CFU/gram of tissue) at the end of the experiment to assess robustness of treatment. In addition, each of these models can be used to define the PK/PD indices and magnitude for efficacy, e.g., AUC/MIC. These models will thus be used to evaluate the efficacy of representative GN anti-*pseudomonas* lysins in a murine model of pulmonary infection alone or in combination with an antibiotic to determine the best GN lysin candidates for further in vivo testing and development. Similar models can be established using *Acinetobacter baumannii* and used to test the efficacy of the present lysins.

B.1 Murine Neutropenic Thigh Infection and Lung Infection Models Thigh Infection Model To establish the first model, CD-1 mice (n=12) are rendered neutropenic by the administration of cyclophosphamide 20 mg/mL administered intraperitoneally following a dosing regimen that provides greater than 99% reduction in neutrophil counts (150 mg/kg on day −4 and 100 mg/kg on day −1). A thigh infection is established by intramuscular (IM) injection into both lateral thigh muscles of an appropriate inoculum of *P. aeruginosa* ($3\times10^4$ or $1\times10^5$ or $3\times10^5$ or $1\times10^6$ cfu/thigh) 24 hours after the second dose of immunosuppressive agent. Mice are infected while under inhaled anesthesia by intramuscular injection into both lateral thigh muscles. Each thigh can receive approximately $1.4\times10^5$ CFU *A. baumannii* NCTC 13301 (and/or an equivalent amount of a *P. aeruginosa* strain). But adjustments to the amount of inoculum can be made if testing indicates this is appropriate.

Groups of 4 mice (6, vehicle only (end group)) are administered test GN lysin or vehicle or control lysin by intravenous (iv) injection at 2, 6 and 10 h post-infection. At 2 h post-infection a control group of 4 animals are humanely euthanized using pentobarbitone overdose to provide a pre-treatment control group (start). 16 hours post infection all remaining groups are humanely euthanized by pentobarbitone. Both thighs from each animal are removed and weighed individually (regarded as two independent evaluations). The lysins that will be tested would include native and modified lysins that have promising properties, i.e., substantial lytic activity and maintenance of substantial activity in the presence of blood matrices. The dosage range tested in this and other experiments detailed herein will be within the broad range of 0.01 to 500 mg/kg, but the upper limit may depend on toxicity and the lower limit maybe higher depending on intrinsic activity. Examples of lysins to be tested include GN108, GN121, GN123, and GN156.

Individual thigh tissue samples are homogenized in ice cold sterile phosphate buffered saline. Thigh homogenates are then quantitatively cultured onto CLED agar and incubated at 37° C. for 24 hours before colonies are enumerated. It is anticipated that lysins will result in a substantial reduction or elimination of bacterial colonies.

Mouse Lung Infection Model

Groups of up to 8 anaesthetized (IP injection of 100 mg/kg ketamine/6 mg/kg xylazine mixture) mice per treatment are infected by intranasal instillation of 20 µl inoculum into each nostril (5 min between nostrils) and kept in an upright position for ~10 minutes post-infection. The strength and amount of an appropriate inoculum is previously determined as described above.

The inoculum concentration is ~$2.5\times10^6$ cfu/ml ($1.0\times10^5$ cfu/lung) for $P.$ $aeruginosa$ ATCC 27853 or ~$8.8\times10^8$ cfu/ml ($3.5\times10^7$ cfu/lung) for $A.$ $baumannii$ NCTC 13301. Lysins (for example the lysins identified in the preceding experiment) are dosed using the same route of administration and dosing guidelines and lungs removed and prepared for counting as per the thigh model. Colonies are enumerated following incubation at 37° C. for 24 h. Efficacy will be assessed in terms of weight of mice and bacterial burden of the lung homogenates. It is anticipated that the lysins will perform satisfactorily in abating infection as measured by substantially reduced or eliminated bacterial colonies.

B.2 Neutropenic Murine Lung Infection Model

Neutropenic BALB/c mice will be inoculated with $P.$ $aeruginosa$ bacteria containing an inoculum sufficient to establish a lung infection via intranasal instillation under anesthesia. Groups of 4 mice (6, vehicle only (end group)) are administered GN lysin, vehicle or control lysin by subcutaneous (SC) injection at 2, 6 and 10 h post-infection. At 2 h post-infection a control group of 4 animals are humanely euthanized using pentabarbitone overdose to provide a pre-treatment control group (start). 16 hours post infection all remaining groups are humanely euthanized by pentabarbitone. The animals are weighed and both lungs from each animal are removed and weighed individually. The lysins and dosing may be the same as described above.

Individual lung tissue samples are homogenized in ice cold sterile phosphate buffered saline. Thigh homogenates are then quantitatively cultured onto CLED agar and incubated at 37° C. for 24 hours before colonies are enumerated. The efficacy of the treatment is assessed in terms of weight and bacterial burden.

Groups of up to 8 anaesthetized (IP injection of 100 mg/kg ketamine/6 mg/kg xylazine mixture) mice per treatment are infected by intranasal instillation of $P.$ $aeruginosa$ inoculum into each nostril (5 min between nostrils) and kept in an upright position for ~10 minutes post-infection. The mice are previously immunosuppressed with cyclophosphamide administered subcutaneously at 200 mg/kg on day −4 and 150 mg/kg on day −1. Infection takes place 24 hrs after the second immunosuppression dose.

The starting inoculum concentration may be ~$2.5\times10^6$ cfu/ml ($1.0\times10^5$ cfu/lung) for $P.$ $aeruginosa$ ATCC 27853. Adjustments to the inoculum may be made, aiming to produce an increase in untreated mouse bacterial burden of about 1 log 10 cfu/g lung. For the survival studies described below, an inoculum will be selected that will lead to death in 24 to 72 hours.

Lysins are then dosed intranasally, mice are euthanized, weighed, the lungs extracted and weighed, and lungs removed and prepared for counting as per the thigh model. Colonies are enumerated following incubation at 37° C. for 24 h. The same lysins and dosing may be used as above. Lysins will be administered intravenously at ml/kg.

In a related experiment, a suboptimal dose of an antibiotic having activity against Gram-negative bacteria, will be selected and used at a subthreshold level together with lysin. An appropriate subthreshold level can be established by treating infected mice with various doses of the antibiotic which doses are below, at and above the minimum efficacious dose. Control mice will be treated with various doses of vehicle alone. There will be one vehicle as a stand-in for the lysin treatment and another vehicle as a stand-in for the antibiotic. 40 mice will be used (5 per group) for each lysin being tested.

If imipenem is the antibiotic, a suitable subthreshold dose is likely to be between 10 and 100 mg/kg (more generally, the subthreshold or suboptimal dose may be one that effects a 1 or 2 log reduction of bacterial burden) and will be administered for example at 5 ml/kg subcutaneously or intravenously for this and the combination (antibiotic+lysin) experiments.

For the combination experiment, it is contemplated that the dose of antibiotic (for example imipenem) will be the maximum subthreshold dose tested. An appropriate dose of lysin will be determined by testing different doses of lysin in the combination treatment to see where a synergistic effect occurs. An optimum set of amounts of lysin and antibiotic will them be selected. The lysin and first treatment of antibiotic will be administered 2 hours post-infection; the second antibiotic treatment will be administered 6 hours post-infection. Tissue will be harvested 9 hours post-infection.

A similar study will be conducted using the same mouse pulmonary infection model but only mouse survival will be assessed. Infected mice will be administered lysin (or vehicle or control lysin) at 24 hours post-infection. It is contemplated that three different doses of each lysin will be used. Imipenem (or vehicle) will be administered 6 hours after the lysin dosing. The experiment will end 72 hours after infection. It is contemplated that the survival experiment will use 7 mice per group, i.e., 63 mice for each lysin tested. It is anticipated that the percentage survival will be superior when the combination is administered.

C. PK/PD Analysis in a Murine Infection Model

Animal experiments with anti-infectives that delineate the PK/PD variables (e.g., Cmax/MIC, AUC/MIC or % Time/MIC) most closely linked to efficacy are highly predictive of clinical success (31). Dose fractionation is employed to determine the PK/PD parameter associated with efficacy. By fractionating a single total dose into once a day (q24 h), twice a day (q12 h), or four times a day (q6h) dosing multiple values for Cmax and free drug Time>MIC (fT>MIC) can be attained while maintaining a constant AUC. Fractionation of multiple doses generates unique exposure profiles that, when compared to efficacy endpoints, enables differentiation of Cmax/MIC, fT>MIC and AUC/MIC as the PK index and magnitude required for efficacy.

GN lysins with robust activity in one or more murine infection models identified above will undergo PK/PD analysis. PK studies will be conducted to generate multiple PK profiles and modeled to cover ranges of Cmax/MIC, AUC/MIC and fT>MIC. Dose fractionation studies will be conducted in a pulmonary efficacy model as described above (mouse rat or rabbit). The tissue bacterial burden will be utilized as the PD endpoint and data will be analyzed by plotting the CFU/g tissue as a function of different PK/PD parameters. Nonlinear regression analysis will determine which PK/PD parameter is important for efficacy. These data will be used to inform doses for non-clinical activities.

One way of conducting the PK study is the following:

TABLE 10

| Dose Level (mg/kg) | Route of administration | Time point of sample collection (h) | Number of animals/ time point | Total number of mice |
|---|---|---|---|---|
| 10 | IV | 0.083, 0.25, 0.5, 1, 2, 4, 8, 24 | 3 | 24 |
| 30 | IV | 0.083, 0.25, 0.5, 1, 2, 4, 8, 24 | 3 | 24 |
| 100 | IV | 0.083, 0.25, 0.5, 1, 2, 4, 8, 24 | 3 | 24 |

At the times indicated in Table 10, mice will be euthanized and groups of three mice per time point will have blood samples collected by cardiac puncture. Separated plasma samples will be divided into two aliquots. Following blood collection, 3× bronchoalveolar lavage samples (PBS) will be collected from a narrow transverse opening made in the trachea. The three BAL samples will be combined and centrifuged to remove cellular debris. BAL supernatant will be divided into two aliquots. One sample of plasma and BAL will be further tested for lysin content and bacterial burden. The second sample will be analyzed for urea content to calculate the dilution of epithelial lining fluid (ELF) during collection of BAL.

D. Monitoring for Development of Resistance In Vivo

To identify a potential for development of resistance, in vivo homogenates from the mouse efficacy studies will be subjected to MIC analysis. If a greater than 2-fold increase in MIC is observed, the bacteria will be plated, and colonies isolated for whole genome sequencing.

EMBODIMENTS

A. A pharmaceutical composition comprising: an isolated lysin polypeptide selected from the group consisting of one or more of GN147, GN146, GN156, GN92, GN54, GN201, GN202, GN121, GN94, GN200, GN204, GN205 or a fragment thereof having lysin activity, or a variant thereof having lytic activity and having at least 80% sequence identity with said lysin polypeptide, and a pharmaceutically acceptable carrier, wherein the lysin polypeptide or fragment or variant is in an amount effective to inhibit the growth, or reduce the population, or kill *P. aeruginosa* and optionally at least one other species of Gram-negative bacteria.

B. A pharmaceutical composition comprising an effective amount of an isolated lysin polypeptide selected from the group consisting of one or more of GN3, GN13, GN17, GN9, GN10, GN105, GN108, GN123, GN150, GN203, or a fragment thereof having lysin activity, or a variant thereof having lytic activity and having at least 80% sequence identity with said lysin polypeptide, and a pharmaceutically acceptable carrier, wherein the lysin polypeptide is in an amount effective to inhibit the growth, or reduce the population, or kill *P. aeruginosa* and optionally at least one other species of Gram-negative bacteria; and a pharmaceutically acceptable carrier.

C. The pharmaceutical composition of embodiment A or B, which is a solution, a suspension, an emulsion, an inhalable powder, an aerosol, or a spray.

D. The pharmaceutical composition of embodiment B further comprising one or more antibiotics suitable for the treatment of Gram-negative bacteria.

E. A vector comprising an isolated polynucleotide comprising a nucleic acid molecule that encodes a lysin polypeptide of embodiment A or B, wherein the encoded lysin polypeptide inhibits the growth, or reduces the population, or kills *P. aeruginosa* and optionally at least one other species of Gram-negative bacteria or a complementary sequence of said polynucleotide.

F. A recombinant expression vector comprising a nucleic acid encoding a lysin polypeptide comprising an amino acid sequence of a polypeptide according to embodiment A or B wherein the encoded lysin polypeptide has the property of inhibiting the growth, or reducing the population, or killing *P. aeruginosa* and optionally at least one other species of Gram-negative bacteria, the nucleic acid being operatively linked to a heterologous promoter.

G. A host cell comprising the vector of embodiment E or F.

H. The recombinant vector of embodiment E or F, wherein the nucleic acid sequence is a cDNA sequence.

I. An isolated polynucleotide comprising a nucleic acid molecule that encodes a lysin polypeptide selected from the group consisting of GN147, GN146, GN156, GN92, GN54, GN201, GN202, GN121, GN94, GN200, GN204, GN205, or a fragment thereof having lysin activity, or a variant thereof having lytic activity and having at least 80% sequence identity with said lysin polypeptide, wherein the lysin polypeptide inhibits the growth, or reduces the population, or kills *P. aeruginosa* and optionally at least one other species of Gram-negative bacteria.

J. The polynucleotide of embodiment I which is cDNA.

K. A method of inhibiting the growth, or reducing the population, or killing of at least one species of Gram-negative bacteria, the method comprising contacting the bacteria with a pharmaceutical composition containing a lysin polypeptide selected from the group consisting of one or more of GN147, GN146, GN156, GN92, GN54, GN201, GN202, GN121, GN94, GN200, GN204, GN205, GN3, GN13, GN17, GN9, GN10, GN105, GN108, GN123, GN150, GN203 or a fragment thereof having lytic activity or a variant thereof having lytic activity and having at least 80% sequence identity with said lysin polypeptide, in an amount effective to inhibit the growth, or reduce the population, or kill *P. aeruginosa* and optionally at least one other species of Gram-negative bacteria.

L. A method of treating a bacterial infection caused by a Gram-negative bacteria selected from the group consisting of *P. aeruginosa* and optionally one or more additional species of Gram-negative bacteria, comprising administering to a subject diagnosed with, at risk for, or exhibiting symptoms of a bacterial infection, a composition containing a lysin polypeptide selected from the group consisting of one or more of GN147, GN146, GN156, GN92, GN54, GN201, GN202, GN121, GN94, GN200, GN204, GN 205, GN3, GN13, GN17, GN9, GN10, GN105, GN108, GN123, GN150, GN203 or a fragment thereof having lysin activity, or a variant thereof having lytic activity and having at least 80% sequence identity with said lysin polypeptide, in an amount effective to inhibit the growth, or reduce the population, or kill *P. aeruginosa* and optionally at least one other species of Gram-negative bacteria.

M. The method of embodiment L, wherein at least one species of Gram-negative bacteria is selected from the group consisting of *Pseudomonas aeruginosa, Klebsiella* spp., *Enterobacter* spp., *Escherichia coli, Citrobacter freundii, Salmonella typhimurium, Yersinia pestis*, and *Franciscella tulerensis*.

N. The method of embodiment L, wherein the Gram-negative bacterial infection is an infection caused by *Pseudomonas aeruginosa*.

O. A method of treating a topical or systemic pathogenic bacterial infection caused by a Gram-negative bacteria selected from the group consisting of *P. aeruginosa* and optionally one or more additional species of Gram-negative bacteria in a subject, comprising administering to a subject composition containing a lysin polypeptide selected from the group consisting of one or more of GN147, GN146, GN156, GN92, GN54, GN201, GN202, GN121, GN94, GN200, GN204, GN 205, GN3, GN13, GN17, GN9, GN10, GN105, GN108, GN123, GN150, GN203 or fragments thereof having lysin activity, or variants thereof having lytic activity and having at least 80% sequence identity with said lysin polypeptide, in an amount effective to inhibit the growth, or reduce the population, or kill *P. aeruginosa* and optionally at least one other Gram-negative bacteria.

P. A method of preventing or treating a bacterial infection comprising co-administering to a subject diagnosed with, at risk for, or exhibiting symptoms of a bacterial infection, a combination of a first effective amount of the composition containing an effective amount of selected from the group consisting of one or more of GN147, GN146, GN156, GN92, GN54, GN201, GN202, GN121, GN94, GN200, GN204, GN 205, GN3, GN13, GN17, GN9, GN10, GN105, GN108, GN123, GN150, GN203, or a fragment thereof having lytic activity, or a variant thereof having lytic activity and having at least 80% sequence identity with said lysin polypeptide, and a second effective amount of an antibiotic suitable for the treatment of Gram-negative bacterial infection.

Q. The method of embodiment P, wherein the antibiotic is selected from one or more of ceftazidime, cefepime, cefoperazone, ceftobiprole, ciprofloxacin, levofloxacin, aminoglycosides, imipenem, meropenem, doripenem, gentamicin, tobramycin, amikacin, piperacillin, ticarcillin, penicillin, rifampicin, polymyxin B, and colistin.

R. A method for augmenting the efficacy of an antibiotic suitable for the treatment of Gram-negative bacterial infection, comprising co-administering the antibiotic in combination with one or more lysin polypeptides selected from the group consisting of one or more of GN147, GN146, GN156, GN92, GN54, GN201, GN202, GN121, GN94, GN200, GN204, GN205, GN3, GN13, GN17, GN9, GN10, GN105, GN108, GN123, GN150, GN203 or a fragment thereof having lytic activity, or a variant thereof having lytic activity and having at least 80% sequence identity with said lysin polypeptide, wherein administration of the combination is more effective in inhibiting the growth, or reducing the population, or killing the Gram-negative bacteria than administration of either the antibiotic or the lysin polypeptide or active fragment thereof individually.

S. An isolated lysin polypeptide, selected from the group consisting of GN147, GN146, GN156, GN92, GN54, GN201, GN202, GN121, GN94, GN200, GN204, GN205, or a fragment thereof having lysin activity, or a variant thereof having lytic activity and having at least 80% sequence identity with said lysin polypeptide, wherein the lysin polypeptide inhibits the growth, or reduces the population, or kills *P. aeruginosa* and, optionally, at least one other species of Gram-negative bacteria.

T. A lysin polypeptide comprising a Gram-negative native lysin selected from the group consisting of GN3, GN9, GN10, GN13, GN17, GN105, GN108, GN123, GN150 AND GN203, or a fragment thereof having lytic activity, or a variant thereof having lytic activity and having at least 80% sequence identity with said lysin polypeptide, wherein the native lysin or fragment has been optionally modified by substitution of 1 to 3 charged amino acid residues with noncharged amino acid residues, the modified native lysin or fragment retaining lytic activity.

U. A lysin polypeptide comprising a Gram-negative native lysin selected from the group consisting of GN2, GN4, GN14, GN43 and GN37, or a fragment thereof having lytic activity, or a variant thereof having lytic activity and having at least 80% sequence identity with said lysin polypeptide, wherein the native lysin or variant or fragment has been modified by substitution of 1 to 3 charged amino acid residues with noncharged amino acid residues, the modified native lysin or fragment retaining lytic activity.

V. A pharmaceutical composition according to embodiment A or B wherein the lysin polypeptide is selected from the group consisting of one or more of GN156, GN121, GN108 and GN123 or active fragments thereof or variants thereof having lytic activity and having at least 80% sequence identity with said lysin polypeptide.

W. A method according to embodiment K wherein said bacteria are in a biofilm, the method effecting disruption of the biofilm.

REFERENCES

1. Magill S S, Edwards J R, Bamberg W, Beldays Z G, Dumyati G, Kainer M A, Lynfield R, Maloney M, McAllister-Hollod L, Nadle J, Ray S M, Thompson D L, Wilson L E, Fridkin S K, Emerging Infections Program Healthcare-Associated I, Antimicrobial Use Prevalence Survey T. 2014. Multistate point-prevalence survey of health care-associated infections. N Engl J Med 370:1198-1208.
2. Rossolini G M, Arena F, Pecile P, Pollini S. 2014. Update on the antibiotic resistance crisis. Curr Opin Pharmacol 18:56-60.
3. Potron A, Poirel L, Nordmann P. 2015. Emerging broad-spectrum resistance in *Pseudomonas aeruginosa* and *Acinetobacter baumannii*: Mechanisms and epidemiology. Int J Antimicrob Agents 45:568-585.
4. Hattemer A, Hauser A, Diaz M, Scheetz M, Shah N, Allen J P, Porhomayon J, El-Solh A A. 2013. Bacterial and clinical characteristics of health care- and community-acquired bloodstream infections due to *Pseudomonas aeruginosa*. Antimicrob Agents Chemother 57:3969-3975.
5. Anderson D J, Moehring R W, Sloane R, Schmader K E, Weber D J, Fowler V G, Jr., Smathers E, Sexton D J. 2014. Bloodstream infections in community hospitals in the 21st century: a multicenter cohort study. PLoS One 9:e91713.
6. Willmann M, Bezdan D, Zapata L, Susak H, Vogel W, Schroppel K, Liese J, Weidenmaier C, Autenrieth I B, Ossowski S, Peter S. 2015. Analysis of a long-term outbreak of XDR *Pseudomonas aeruginosa*: a molecular epidemiological study. J Antimicrob Chemother 70:1322-1330.
7. Bassetti M, Righi E. 2015. New antibiotics and antimicrobial combination therapy for the treatment of gram-negative bacterial infections. Curr Opin Crit Care 21:402-411.
8. Wittekind M, Schuch R. 2016. Cell wall hydrolases and antibiotics: exploiting synergy to create efficacious new antimicrobial treatments. Curr Opin Microbiol 33:18-24.
9. Schmelcher M, Donovan D M, Loessner M J. 2012. Bacteriophage endolysins as novel antimicrobials. Future Microbiol 7:1147-1171.
10. Schuch R, Lee H M, Schneider B C, Sauve K L, Law C, Khan B K, Rotolo J A, Horiuchi Y, Couto D E, Raz A, Fischetti V A, Huang D B, Nowinski R C, Wittekind M. 2014. Combination therapy with lysin CF-301 and antibiotic is superior to antibiotic alone for treating methicillin-resistant *Staphylococcus aureus*-induced murine bacteremia. J Infect Dis 209:1469-1478.
11. Schuch R, Nelson D, Fischetti V A. 2002. A bacteriolytic agent that detects and kills *Bacillus anthracis*. Nature 418:884-889.
12. Briers Y, Lavigne R. 2015. Breaking barriers: expansion of the use of endolysins as novel antibacterials against Gram-negative bacteria. Future Microbiol 10:377-390.
13. Lood R. 2015. Novel phage lysin capable of killing the multidrug-resistant gram-negative bacterium *Acinetobacter baumannii* in a mouse bacteremia model. 59:1983-1991.
14. Thandar M, Lood R, Winer B Y, Deutsch D R, Euler C W, Fischetti V A. 2016. Novel Engineered Peptides of a Phage Lysin as Effective Antimicrobials against Multidrug-Resistant *Acinetobacter baumannii*. Antimicrob Agents Chemother 60:2671-2679.
15. Silhavy T J, Kahne D, Walker S. 2010. The bacterial cell envelope. Cold Spring Harb Perspect Biol 2:a000414.
16. Vaara M. 1992. Agents that increase the permeability of the outer membrane. Microbiol Rev 56:395-411.
17. Gerstmans H, Rodriguez-Rubio L, Lavigne R, Briers Y. 2016. From endolysins to Artilysin(R)s: novel enzyme-based approaches to kill drug-resistant bacteria. Biochem Soc Trans 44:123-128.
18. Zhu X, Ma Z, Wang J, Chou S, Shan A. 2014. Importance of Tryptophan in Transforming an Amphipathic Peptide into a *Pseudomonas aeruginosa*-Targeted Antimicrobial Peptide. PLoS One 9:e114605.
19. Deslouches B, Islam K, Craigo J K, Paranjape S M, Montelaro R C, Mietzner T A. 2005. Activity of the de novo engineered antimicrobial peptide WLBU2 against *Pseudomonas aeruginosa* in human serum and whole blood: implications for systemic applications. Antimicrob Agents Chemother 49:3208-3216.
20. Yeaman M R, Yount N Y. 2003. Mechanisms of antimicrobial peptide action and resistance. Pharmacol Rev 55:27-55.
21. Wang J, Chou S, Xu L, Zhu X, Dong N, Shan A, Chen Z. 2015. High specific selectivity and Membrane-Active Mechanism of the synthetic centrosymmetric alpha-helical peptides with Gly-Gly pairs. Sci Rep 5:15963.
22. Lyu Y, Yang Y, Lyu X, Dong N, Shan A. 2016. Antimicrobial activity, improved cell selectivity and mode of action of short PMAP-36-derived peptides against bacteria and *Candida*. Sci Rep 6:27258.
23. Sanchez-Gomez S, Lamata M, Leiva J, Blondelle S E, Jerala R, Andra J, Brandenburg K, Lohner K, Moriyon I, Martinez-de-Tejada G. 2008. Comparative analysis of selected methods for the assessment of antimicrobial and membrane-permeabilizing activity: a case study for lactoferricin derived peptides. BMC Microbiol 8:196.
24. Guzman L M, Belin D, Carson M J, Beckwith J. 1995. Tight regulation, modulation, and high-level expression by vectors containing the arabinose PBAD promoter. J Bacteriol 177:4121-4130.
25. Lood R, Raz A, Molina H, Euler C W, Fischetti V A. 2014. A highly active and negatively charged *Streptococcus pyogenes* lysin with a rare D-alanyl-L-alanine endopeptidase activity protects mice against streptococcal bacteremia. Antimicrob Agents Chemother 58:3073-3084.
26. CLSI. 2015. Methods for Dilution Antimicrobial Susceptibility Tests for Bacteria That Grow Aerobically; Approved Standard-10th Edition. Clinical and Laboratory Standards Institute, Wayne, PA.
27. Ceri H, Olson M E, Stremick C, Read R R, Morck D, Buret A. 1999. The Calgary Biofilm Device: new technology for rapid determination of antibiotic susceptibilities of bacterial biofilms. J Clin Microbiol 37:1771-1776.
28. Schuch R, Khan B K, Raz A, Rotolo J A, Wittekind M. 2017. Bacteriophage Lysin CF-301, a Potent Antistaphylococcal Biofilm Agent. Antimicrob Agents Chemother 61.
29. Moody J. 2010. Synergy testing: broth microdilution checkerboard and broth macrodilution methods, p 5.12.11-15.12.23. In Garcia L S (ed), Clinical Microbiology Procedures Handbook, vol 2. ASM Press, Washington, D.C.
30. Lv Y, Wang J, Gao H, Wang Z, Dong N, Ma Q, Shan A. 2014. Antimicrobial properties and membrane-active mechanism of a potential alpha-helical antimicrobial derived from cathelicidin PMAP-36. PLoS One 9:e86364.
31. Scanlon T C, Teneback C C, Gill A, Bement J L, Weiner J A, Lamppa J W, Leclair L W, Griswold K E. 2010. Enhanced antimicrobial activity of engineered human lysozyme. ACS Chem Biol 5:809-818.
32. Teneback C C, Scanlon T C, Wargo M J, Bement J L, Griswold K E, Leclair L W. 2013. Bioengineered lysozyme reduces bacterial burden and inflammation in a murine model of mucoid *Pseudomonas aeruginosa* lung infection. Antimicrob Agents Chemother 57:5559-5564.
33. Griswold K E, Bement J L, Teneback C C, Scanlon T C, Wargo M J, Leclair L W. 2014. Bioengineered lysozyme in combination therapies for *Pseudomonas aeruginosa* lung infections. Bioengineered 5:143-147.
34. Daniels D S, Schepartz A. 2007. Intrinsically cell-permeable miniature proteins based on a minimal cationic PPII motif. J Am Chem Soc 129:14578-14579.
35. Vaara M, Porro M. 1996. Group of peptides that act synergistically with hydrophobic antibiotics against gram-negative enteric bacteria. Antimicrob Agents Chemother 40:1801-1805.
36. Briers Y, Walmagh M, Van Puyenbroeck V, Cornelissen A, Cenens W, Aertsen A, Oliveira H, Azeredo J, Verween G, Pirnay J P, Miller S, Volckaert G, Lavigne R. 2014. Engineered endolysin-based "Artilysins" to combat multidrug-resistant gram-negative pathogens. MBio 5:e01379-01314.
37. Briers Y, Walmagh M, Grymonprez B, Biebl M, Pirnay J P, Defraine V, Michiels J, Cenens W, Aertsen A, Miller S, Lavigne R. 2014. Art-175 is a highly efficient antibacterial against multidrug-resistant strains and persisters of *Pseudomonas aeruginosa*. Antimicrob Agents Chemother 58:3774-3784.

The invention claimed is:

1. A pharmaceutical composition comprising: (1) one or more isolated modified lysin polypeptides comprising an amino acid sequence selected from the group consisting of GN146 (SEQ ID NO: 4), GN156 (SEQ ID NO: 6), GN92 (SEQ ID NO: 7), GN54 (SEQ ID NO: 8), GN202 (SEQ ID NO: 9), fragments thereof having lytic activity, and variants thereof having lytic activity, wherein said fragments and variants have at least 80% sequence identity with a lysin polypeptide of GN4 (SEQ ID NO: 3) and comprise amino acid substitutions K100D and R116H relative to SEQ ID NO: 3, and (2) a pharmaceutically acceptable carrier.

2. The pharmaceutical composition of claim 1, which is a solution, a suspension, an emulsion, an inhalable powder, an aerosol, or a spray.

3. The pharmaceutical composition of claim 1 further comprising one or more antibiotics suitable for the treatment of a Gram-negative bacterial infection.

4. The pharmaceutical composition according to claim 1, wherein the modified lysin polypeptide comprises an amino acid sequence selected from the group consisting of one or more of GN146 (SEQ ID NO: 4), fragments thereof having lytic activity, and variants thereof having lytic activity, wherein said fragments and variants have at least 90% sequence identity with a lysin polypeptide of GN4 (SEQ ID NO: 3) and comprise amino acid substitutions K100D and R116H relative to SEQ ID NO: 3.

5. The pharmaceutical composition according to claim 4, wherein the modified lysin polypeptide further comprises an antimicrobial peptide sequence of SEQ ID NO: 28 at the N-terminus of the modified lysin polypeptide.

6. The pharmaceutical composition according to claim 1, wherein the one or more isolated modified lysin polypeptides further comprise an antimicrobial peptide sequence of SEQ ID NO: 28, SEQ ID NO: 29, or SEQ ID NO: 30 at the N- or C-terminus of the modified lysin polypeptide.

7. The pharmaceutical composition of claim 1, wherein the isolated modified lysin polypeptide comprises GN146 (SEQ ID NO: 4), fragments thereof having lytic activity, and variants thereof having lytic activity, wherein said fragments and variants have at least 95% sequence identity with a lysin polypeptide of GN4 (SEQ ID NO: 3) and comprise amino acid substitutions K100D and R116H relative to SEQ ID NO: 3.

8. The pharmaceutical composition of claim 7, wherein the isolated modified lysin polypeptide further comprises an antimicrobial peptide sequence of SEQ ID NO: 28 at the N-terminus of the modified lysin polypeptide.

9. The pharmaceutical composition of claim 8, wherein the isolated modified lysin polypeptide comprises GN146 (SEQ ID NO: 4).

10. A method of inhibiting the growth, or reducing the population, or killing of at least one species of Gram-negative bacteria, the method comprising contacting the bacteria with a pharmaceutical composition of claim 1 in an amount effective to inhibit the growth, or reduce the population, or kill the at least one species of Gram-negative bacteria.

11. The method according to claim 10, wherein said bacteria are in a biofilm, the method effecting disruption of the biofilm.

12. The method of claim 10, wherein the modified lysin polypeptide comprises an amino acid sequence selected from the group consisting of GN146 (SEQ ID NO: 4), fragments thereof having lytic activity, and variants thereof having lytic activity, wherein said fragments and variants have at least 90% sequence identity with a lysin polypeptide of GN4 (SEQ ID NO: 3) and comprise amino acid substitutions K100D and R116H relative to SEQ ID NO: 3 and further comprises an antimicrobial peptide sequence of SEQ ID NO: 28 at the N-terminus of the modified lysin polypeptide.

13. A method of treating a bacterial infection caused by a Gram-negative bacteria comprising administering to a subject diagnosed with, or exhibiting symptoms of a bacterial infection, the pharmaceutical composition of claim 1 in an amount effective to inhibit the growth, or reduce the population, or kill at least one species of Gram-negative bacteria.

14. The method of claim 13, wherein the at least one species of Gram-negative bacteria is selected from the group consisting of *Pseudomonas aeruginosa, Klebsiella* spp.,

*Enterobacter* spp., *Escherichia coli*, *Citrobacter freundii*, *Salmonella typhimurium*, *Yersinia pestis*, and *Franciscella tulerensis*.

15. The method of claim 13, wherein the Gram-negative bacterial infection is an infection caused by *Pseudomonas aeruginosa*.

16. The method of claim 13, wherein the bacterial infection is a topical or systemic pathogenic bacterial infection.

17. The method of claim 13, further comprising co-administering to the subject an effective amount of an antibiotic suitable for the treatment of a Gram-negative bacterial infection.

18. The method of claim 17, wherein the antibiotic is selected from one or more of ceftazidime, cefepime, cefoperazone, ceftobiprole, ciprofloxacin, levofloxacin, aminoglycosides, imipenem, meropenem, doripenem, gentamicin, tobramycin, amikacin, piperacillin, ticarcillin, penicillin, rifampicin, polymyxin B, and colistin.

19. The method of claim 13, wherein the modified lysin polypeptide comprises an amino acid sequence selected from the group consisting of GN146 (SEQ ID NO: 4), fragments thereof having lytic activity, and variants thereof having lytic activity, wherein said fragments and variants have at least 90% sequence identity with a lysin polypeptide of GN4 (SEQ ID NO: 3) and comprise amino acid substitutions K100D and R116H relative to SEQ ID NO: 3 and further comprises an antimicrobial peptide sequence of SEQ ID NO: 28 at the N-terminus of the modified lysin polypeptide.

20. A method for augmenting the efficacy of an antibiotic suitable for the treatment of Gram-negative bacterial infection, comprising co-administering the antibiotic in combination with the pharmaceutical composition of claim 1.

21. The method of claim 20, wherein the modified lysin polypeptide comprises an amino acid sequence selected from the group consisting of GN146 (SEQ ID NO: 4), fragments thereof having lytic activity, and variants thereof having lytic activity, wherein said fragments and variants have at least 90% sequence identity with a lysin polypeptide of GN4 (SEQ ID NO: 3) and comprise amino acid substitutions K100D and R116H relative to SEQ ID NO: 3 and further comprises an antimicrobial peptide sequence of SEQ ID NO: 28 at the N-terminus of the modified lysin polypeptide.

22. A vector comprising an isolated polynucleotide comprising a nucleic acid molecule that encodes a modified lysin polypeptide comprising an amino acid sequence selected from the group consisting of GN146 (SEQ ID NO: 4), GN156 (SEQ ID NO: 6), GN92 (SEQ ID NO: 7), GN54 (SEQ ID NO: 8), GN202 (SEQ ID NO: 9), fragments thereof having lytic activity, and variants thereof having lytic activity, wherein said fragments and variants have at least 80% sequence identity with a lysin polypeptide of GN4 (SEQ ID NO: 3) and comprise amino acid substitutions K100D and R116H relative to SEQ ID NO: 3.

23. The vector of claim 22, wherein the nucleic acid sequence is a cDNA sequence.

24. A host cell comprising the vector of claim 22.

25. A recombinant expression vector comprising a nucleic acid encoding a lysin polypeptide comprising an amino acid sequence of a modified lysin polypeptide comprising an amino acid sequence selected from the group consisting of GN146 (SEQ ID NO: 4), GN156 (SEQ ID NO: 6), GN92 (SEQ ID NO: 7), GN54 (SEQ ID NO: 8), GN202 (SEQ ID NO: 9), fragments thereof having lytic activity, and variants thereof having lytic activity, wherein said fragments and variants have at least 80% sequence identity with a lysin polypeptide of GN4 (SEQ ID NO: 3) and comprise amino acid substitutions K100D and R116H relative to SEQ ID NO: 3, the nucleic acid being operatively linked to a heterologous promoter.

26. An isolated polynucleotide comprising a nucleic acid molecule that encodes a modified lysin polypeptide comprising an amino acid sequence selected from the group consisting of GN146 (SEQ ID NO: 4), GN156 (SEQ ID NO: 6), GN92 (SEQ ID NO: 7), GN54 (SEQ ID NO: 8), GN202 (SEQ ID NO: 9), fragments thereof having lytic activity, and variants thereof having lytic activity, wherein said fragments and variants have at least 80% sequence identity with a lysin polypeptide of GN4 (SEQ ID NO: 3) and comprise amino acid substitutions K100D and R116H relative to SEQ ID NO: 3.

27. The polynucleotide of claim 26 which is cDNA.

28. The isolated polynucleotide according to claim 26, wherein the modified lysin polypeptide comprises an amino acid sequence selected from the group consisting of GN146 (SEQ ID NO: 4), fragments thereof having lytic activity, and variants thereof having lytic activity, wherein said fragments and variants have at least 90% sequence identity with a lysin polypeptide of GN4 (SEQ ID NO: 3) and comprise amino acid substitutions $K_{100}D$ and R116H relative to SEQ ID NO: 3 and further comprises an antimicrobial peptide sequence of SEQ ID NO: 28 at the N-terminus of the modified lysin polypeptide.

29. The isolated polynucleotide of claim 26, wherein the isolated modified lysin polypeptide comprises GN146 (SEQ ID NO: 4), fragments thereof having lytic activity, and variants thereof having lytic activity, wherein said fragments and variants have at least 95% sequence identity with a lysin polypeptide of GN4 (SEQ ID NO: 3) and comprise amino acid substitutions K100D and R116H relative to SEQ ID NO: 3.

30. The isolated polynucleotide of claim 29, wherein the isolated modified lysin polypeptide further comprises an antimicrobial peptide sequence of SEQ ID NO: 28 at the N-terminus of the modified lysin polypeptide.

31. The isolated polynucleotide of claim 30, wherein the isolated modified lysin polypeptide comprises GN146 (SEQ ID NO: 4).

32. An isolated modified lysin polypeptide comprising an amino acid sequence selected from the group consisting of GN146 (SEQ ID NO: 4), GN156 (SEQ ID NO: 6), GN92 (SEQ ID NO: 7), GN54 (SEQ ID NO: 8), GN202 (SEQ ID NO: 9), fragments thereof having lytic activity, and variants thereof having lytic activity, wherein said fragments and variants have at least 80% sequence identity with a lysin polypeptide of GN4 (SEQ ID NO: 3) and comprise amino acid substitutions K100D and R116H relative to SEQ ID NO: 3.

33. The isolated polypeptide according to claim 32, wherein the modified lysin polypeptide comprises an amino acid sequence selected from the group consisting of GN146 (SEQ ID NO: 4), fragments thereof having lytic activity, and variants thereof having lytic activity, wherein said fragments and variants have at least 90% sequence identity with a lysin polypeptide of GN4 (SEQ ID NO: 3) and comprise amino acid substitutions K100D and R116H relative to SEQ ID NO: 3 and further comprises an antimicrobial peptide sequence of SEQ ID NO: 28, SEQ ID NO: 29, or SEQ ID NO: 30 at the N- or C-terminus of the modified lysin polypeptide.

34. The isolated modified lysin polypeptide of claim 32, wherein the modified lysin polypeptide comprises GN146 (SEQ ID NO: 4), fragments thereof having lytic activity, and variants thereof having lytic activity, wherein said fragments and variants have at least 95% sequence identity with a lysin polypeptide of GN4 (SEQ ID NO: 3) and comprise amino acid substitutions K100D and R116H relative to SEQ ID NO: 3.

35. The isolated modified lysin polypeptide of claim 34, wherein the modified lysin polypeptide further comprises an antimicrobial peptide sequence of SEQ ID NO: 28 at the N-terminus of the modified lysin polypeptide.

36. The isolated modified lysin polypeptide of claim 35, wherein the modified lysin polypeptide comprises GN146 (SEQ ID NO: 4).

* * * * *